(12) United States Patent
Gu et al.

(10) Patent No.: US 12,415,869 B2
(45) Date of Patent: Sep. 16, 2025

(54) CHEMICALLY INDUCED PROTEIN DIMERIZATION SYSTEMS

(71) Applicant: UNIVERSITY OF WASHINGTON, Seattle, WA (US)

(72) Inventors: Liangcai Gu, Seattle, WA (US); Shoukai Kang, Seattle, WA (US); Luis Gomez-Castillo, Seattle, WA (US); Huayi Jiang, Seattle, WA (US)

(73) Assignee: University of Washington, Seattle, WA (US)

( * ) Notice: Subject to any disclaimer, the term of this patent is extended or adjusted under 35 U.S.C. 154(b) by 951 days.

(21) Appl. No.: 17/604,928

(22) PCT Filed: Apr. 21, 2020

(86) PCT No.: PCT/US2020/029052
§ 371 (c)(1),
(2) Date: Oct. 19, 2021

(87) PCT Pub. No.: WO2020/219407
PCT Pub. Date: Oct. 29, 2020

(65) Prior Publication Data
US 2022/0177605 A1    Jun. 9, 2022

Related U.S. Application Data

(60) Provisional application No. 62/837,058, filed on Apr. 22, 2019.

(51) Int. Cl.
*C07K 16/44* (2006.01)
*G01N 33/68* (2006.01)

(52) U.S. Cl.
CPC .......... *C07K 16/44* (2013.01); *G01N 33/6845* (2013.01); *G01N 33/6854* (2013.01); *C07K 2317/565* (2013.01); *C07K 2317/622* (2013.01)

(58) Field of Classification Search
CPC ............................ C07K 16/44; G01N 33/6845
See application file for complete search history.

(56) References Cited

U.S. PATENT DOCUMENTS

| | | |
|---|---|---|
| 9,976,122 B2 | 5/2018 | Spencer et al. |
| 2004/0220388 A1 | 11/2004 | Mertens et al. |
| 2016/0361436 A1 | 12/2016 | Davis et al. |
| 2018/0022794 A1 | 1/2018 | Olichon et al. |
| 2018/0319870 A1 | 11/2018 | Amin et al. |
| 2019/0083665 A1 | 3/2019 | Garcia-Martinez et al. |

FOREIGN PATENT DOCUMENTS

WO    2018/213848    11/2018

OTHER PUBLICATIONS

Di Palma, F. "The Draft Genome of Lepisosteus oculatus," European Nucleotide Archive Accession #: AHAT01000000. Submitted Dec. 2, 2011. (Year: 2011).*
Benchimol. "A0A1J4JYV5_9EUKA," Submitted EMBL/GenBank/DDBJ databases Oct. 2016. (Year: 2016).*
Arbabi-Ghahroudi, M. Camelid Single-Domain Antibodies: Historical Perspective and Future Outlook, Front. Immunol., 2017 vol. 8, Nov. 19, 2017. https://doi.org/10.3389/fimmu.2017.01589. (Year: 2017).*
Zavrtanik, U. Structural Basis of Epitope Recognition by Heavy-Chain Camelid Antibodies, Journal of Molecular Biology, vol. 430, Issue 21, 2018, pp. 4369-4386, https://doi.org/10.1016/j.jmb.2018.09.002. (Year: 2018).*
Parks. "A standardized bacterial taxonomy based on genome phylogeny substantially revises the tree of life," A0A354TL79 9GAMM, Submitted EMBL/GenBank/DDBJ databases Nov. 7, 2018. (Year: 2018).*
Al Qaraghuli, et al., J. Mol. Recognit. 2017, 30.
Ballister, et al., Nat. Commun. 2014, 5.
Banaszynski, et al., J. Am. Chem. Soc. 2005, 127, 4715.
Beckett, et al., Protein Sci. 1999, 8, 921.
Belshaw, et al., Proc. Natl. Acad. Sci. U. S. A. 1996, 93, 4604.
Bradbury, et al., J. Nat. Biotechnol. 2011, 29, 245.
Chen, et al., Nat. Biotechnol. 2001, 19, 537.
Crooks, et al., Genome Res. 2004, 14, 1188.
Daley, T., et al., Nat. Methods 2013, 10, 325.
Derose, et al., Pflugers Arch. 2013, 465, 409.
Di Stasi, et al., N. Engl. J. Med. 2011, 365, 1673.
Douglass, et al., J. Am. Chem. Soc. 2013, 135, 6092.
Erhart, et al., Chemistry & Biology 2013, 20, 549.
Fanning, et al., Protein Sci. 2011, 20, 1196.
Farrar, et al., Nature 1996, 383, 178.
Fegan, et al., Chem. Rev. 2010, 110, 3315.
Gomez-Castillo, et al., "Creating highly chemically induced dimerization systems by stepwise phase selection of a combinatorial single-domain antibody library," Jounral of Visualized Experiments 2020, 155, e60738.
Gormley, et al., Biochemistry 1996, 35, 5083.
Hill, et al., Nat. Chem. Biol. 2018, 14, 112.
Ho, et al., Nature 1996, 382, 822.
Hunter, et al., J. Immunol. 1982, 129, 1165.
Izzo, et al., Trends Pharmacol. Sci. 2009, 30, 515.
Jester, et al., ACS Synthetic Biology Year, 10, 2457.
Kang, et al., "COMBINES-CID: An efficient method for de novo engineering og highly specific chemically induced protain dimerization systems," J. Am. Chem. Soc. 2019, 141(28): 10948-10952.
Lemmer, Nat. Rev. Immunol. 2016, 16, 498.
Li, et al., Angewandte Chemie Year 32, 10226.
Liang, et al., Acta Crystallogr. D Biol. Crystallogr. 1999, 55, 736.
Luo, et al., Nature 2019, 567, 123.
McMahon, et al., Nat. Struct. Mol. Biol. 2018, 25, 289.
Miyamoto, et al., Nat. Chem. Biol. 2012, 8, 465.
Moutel, S.; et al., eLife 2016, 5.

(Continued)

*Primary Examiner* — Daniel E Kolker
*Assistant Examiner* — Julia A Rossi
(74) *Attorney, Agent, or Firm* — McDonnell Boehnen Hulbert & Berghoff

(57) ABSTRACT

The disclosure provides polypeptides, fusion proteins, kits, dimers, nucleic acids, expression vectors, or host cells for use hi chemically induced dimerization systems, exemplified by a chemically induced dimerization system in which two recombinant antibodies dimerize only in the presence of cannabidiol.

18 Claims, 14 Drawing Sheets

Specification includes a Sequence Listing.

(56) References Cited

OTHER PUBLICATIONS

Murase, et al., Nature 2008, 456, 459.
Muyldermans, Annu. Rev. Biochem. 2013, 82, 775.
O'Boyle, et al., J. Cheminform. 2011, 3.
Park, et al., J. Chem. Theory. Comput. 2016, 12, 6201.
Qi, et al., J. Med. Chem. 2005, 48, 7389.
Rivera, et al., Nat. Med. 1996, 2, 1028.
Roehr, et al., Bioinformatics 2017, 33, 2941.
Schuck, Methods. Mol. Biol. 2010, 627, 15.
Schwope, et al., Clin. Chem. 2010, 56, 1007.
Song, et al., Structure 2013, 21, 1735.
Spencer, et al., Science 1993, 262, 1019.
Stanton, et al., Science 2018, 359.
Tinberg, et al., Nature 2013, 501, 212.
Virnekas, et al., Nucleic Acids Res. 1994, 22, 5600.
Wang, et al., J. Mol. Graph. Model. 2006, 25, 247.
Wu, et al., Science 2015, 350.
Zavrtanik, et al., J. Mol. Biol. 2018, 430, 4369.
Zhao, et al., Methods 2013, 59, 328.

\* cited by examiner a b c

US 12,415,869 B2

CHEMICALLY INDUCED PROTEIN DIMERIZATION SYSTEMS

CROSS REFERENCE

This application is a U.S. National Phase of International Application No. PCT/US2020/029052, filed Apr. 21, 2020, which claims priority to U.S. Provisional Application No. 62/837,058, filed Apr. 22, 2019, both of which are incorporated by reference herein it their entirety

FEDERAL FUNDING STATEMENT

This invention was made with government support under Grant No. 1R35GM128918, awarded by the National Institutes of Health. The government has certain rights in the invention.

REFERENCE TO SEQUENCE LISTING

This application contains a Sequence Listing submitted as an electronic text file named "19-685-PCT_Sequence-Listing_ST25.txt", having a size in bytes of 19 kb, and created on Apr. 6, 2020. The information contained in this electronic file is hereby incorporated by reference in its entirety pursuant to 37 CFR § 1.52(e)(5).

BACKGROUND

Chemically induced dimerization (CID) systems, in which two proteins dimerize only in the presence of a small molecule ligand, offer versatile tools for small molecule sensing and actuation. However, only a handful of CID systems exist and creating one with the desired sensitivity and specificity for any given ligand is an unsolved problem.

SUMMARY

In one aspect, the disclosure provides recombinant antibodies, comprising a set of complementarity-determining regions (CDRs) selected from the group consisting of a CDR1, CDR2, and CDR3 combination in any one of rows (a)-(aa) in Table 1. In one embodiment, the antibody is a single-chain antibody. In another embodiment, the antibody comprises a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence of SEQ ID NO:82

(SEQ ID NO: 82)
EVQLQASGGGFVQPGGSLRLSCAASG-(CDR1)-MGWFRQAPGKEREFVS

AIS-(CDR2)-YYADSVKGRFTISRDNSKNTVYLQMNSLRAEDTATYYC

A-(CDR3)-YWGQGTQVTVSS, wherein CDR1, CDR2, and CDR3 comprise a CDR1, CDR2, and CDR3 combination in any one of rows (a)-(aa) in Table 1.

In another embodiment, the antibody comprises a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6PX7

KEREFVSAIS-(CDR2)-YYX8DX9VKGRFTISRDNX10KNTX11YLQM

X12SLX13X14EDTAX15YYCX16-(CDR3)-YWGQGTQVTVSS;

wherein
  X1 is K, Q, N, R, D, or E;
  X2 is D, G, E, A, V, L, or I;
  X3 is L, F, W, G, A, V, L, or I;
  X4 is K, R, D, E, N, or Q;
  X5 is V, P, G, A, L, I, or M;
  X6 is T, A, S, G, V, L, or I;
  X7 is E, G, D, A, V, L, or I;
  X8 is P, A, M, G, V, L, or I;
  X9 is T, or S;
  X10 is A, S, M, G, V, L, or I;
  X11 is L, V, G, A, or I;
  X12 is S, N, Q, or T;
  X13 is K, R, D, or E;
  X14 is S, A, T, G, V, L, or I;
  X15 is M, T, V, L, or I;
  X16 is V, G, L, I, or A; and
    wherein CDR1, CDR2, and CDR3 comprise a CDR1, CDR2, and CDR3 combination in any one of rows (a)-(aa) in Table 1.

In another embodiment, the set of CDRs comprises a set of complementarity-determining regions (CDRs) selected from the group consisting of a CDR1, CDR2, and CDR3 combination in any one of rows (a), (i), (n), (u), and (x) in Table 1. In further embodiments, the antibodies comprise one or more functional domains, and/or are bound to a solid support.

In another embodiment, the disclosure provides fusion proteins, comprising:
  (a) a first recombinant antibody, comprising the set of complementarity determining regions (CDRs) of SEQ ID NO:1, 2, and 3;
  (b) a second recombinant antibody, comprising a set of complementarity determining regions (CDRs) selected from the group consisting of a CDR1, CDR2, and CDR3 combination in any one of rows (d)-(aa) in Table 1; and
  (c) a linker between the first antibody and the second antibody. In one embodiment, the second recombinant antibody comprises a set of complementarity determining regions (CDRs) selected from the group consisting of a CDR1, CDR2, and CDR3 combination in any one of rows (i), (n), (u), and (x) in Table 1. In another embodiment the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 82)
EVQLQASGGGFVQPGGSLRLSCAASG-(CDR1)-MGWFRQAPGKEREFVS

AIS-(CDR2)-YYADSVKGRFTISRDNSKNTVYLQMNSLRAEDTATYYC

A-(CDR3)-YWGQGTQVTVSS;

wherein for the second antibody CDR1, CDR2, and CDR3 comprise a CDR1, CDR2, and CDR3 combination in any one of rows (d)-(aa) in Table 1. In a further embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6PX7

KEREFVSAIS-(CDR2)-YYX8DX9VKGRFTISRDNX10KNTX11YLQM

X12SLX13X14EDTAX15YYCX16-(CDR3)-YWGQGTQVTVSS;

wherein
  X1 is K, Q, N, R, D, or E;
  X2 is D, G, E, A, V, L, or I;
  X3 is L, F, W, G, A, V, L, or I;
  X4 is K, R, D, E, N, or Q,
  X5 is V, P, G, A, L, I, or M;
  X6 is T, A, S, G, V, L, or I;
  X7 is E, G, D, A, V, L, or I;
  X8 is P, A, M, G, V, L, or I;
  X9 is T, or S;
  X10 is A, S, M, G, V, L, or I;
  X11 is L, V, G, A, or I;
  X12 is S, N, Q, or T;
  X13 is K, R, D, or E;
  X14 is S, A, T, G, V, L, or I;
  X15 is M, T, V, L, or I;
  X16 is V, G, L, I, or A; and
    wherein for the second antibody CDR1, CDR2, and CDR3 comprise a CDR1, CDR2, and CDR3 combination in any one of rows (d)-(aa) in Table 1.

In another embodiment, the disclosure provides kits, comprising:
  (a) a first recombinant antibody, comprising the set of complementarity determining regions (CDRs) of SEQ ID NO:1, 2, and 3;
  (b) a second recombinant antibody, comprising a set of complementarity determining regions (CDRs) selected from the group consisting of a CDR1, CDR2, and CDR3 combination in any one of rows (d)-(aa) in Table 1; and
  (c) cannabidiol, or a salt thereof. In one embodiment, the second recombinant antibody comprises a set of complementarity determining regions (CDRs) selected from the group consisting of a CDR1, CDR2, and CDR3 combination in any one of rows (i), (n), (u), and (x) in Table 1. In another embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 82)
EVQLQASGGGFVQPGGSLRLSCAASG-(CDR1)-MGWFRQAPGKEREFVS

AIS-(CDR2)-YYADSVKGRFTISRDNSKNTVYLQMNSLRAEDTATYYC

A-(CDR3)-YWGQGTQVTVSS wherein for the second antibody CDR1, CDR2, and CDR3 comprise a CDR1, CDR2, and CDR3 combination in any one of rows (d)-(aa) in Table 1. In a further embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6P

X7KEREFVSAIS-(CDR2)-YYX8DX9VKGRFTISRDNX10KNTX11Y

LQMX12SLX13X14EDTAX15YYCX16-(CDR3)-YWGQGTQVTVSS;

wherein
  X1 is K, Q, N, R, D, or E;
  X2 is D, G, E, A, V, L, or I;
  X3 is L, F, W, G, A, V, L, or I;
  X4 is K, R, D, E, N, or Q,
  X5 is V, P, G, A, L, I, or M;
  X6 is T, A, S, G, V, L, or I;
  X7 is E, G, D, A, V, L, or I;
  X8 is P, A, M, G, V, L, or I;
  X9 is T, or S;
  X10 is A, S, M, G, V, L, or I;
  X11 is L, V, G, A, or I;
  X12 is S, N, Q, or T;
  X13 is K, R, D, or E;
  X14 is S, A, T, G, V, L, or I;
  X15 is M, T, V, L, or I;
  X16 is V, G, L, I, or A; and
    wherein for the second antibody CDR1, CDR2, and CDR3 comprise a CDR1, CDR2, and CDR3 combination in any one of rows (d)-(aa) in Table 1.

In another embodiment, the disclosure provides dimers comprising
  (a) a first recombinant antibody, comprising the set of complementarity determining regions (CDRs) of SEQ ID NO:1, 2, and 3;
  (b) a second recombinant antibody, comprising a set of complementarity determining regions (CDRs) selected from the group consisting of a CDR1, CDR2, and CDR3 combination in any one of rows (d)-(aa) in Table 1; and
  (c) cannabidiol, or a salt thereof, wherein the first recombinant antibody and the second recombinant antibody dimerize in the presence of cannabidiol. In one embodiment, the second recombinant antibody comprises a set of complementarity determining regions (CDRs) selected from the group consisting of a CDR1, CDR2, and CDR3 combination in any one of rows (i), (n), (u), and (x) in Table 1. In another embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 82)
EVQLQASGGGFVQPGGSLRLSCAASG-(CDR1)-MGWFRQAPGKEREFVS

AIS-(CDR2)-YYADSVKGRFTISRDNSKNTVYLQMNSLRAEDTATYYC

A-(CDR3)-YWGQGTQVTVSS;

wherein for the second antibody CDR1, CDR2, and CDR3 comprise a CDR1, CDR2, and CDR3 combination in any one of rows (d)-(aa) in Table 1. In a further embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6PX7KEREFVSAIS-(CDR2)-YYX8DX9VKGRFTISRDNX10KNTX11YLQMX12SLX13X14EDTAX15YYCX16-(CDR3)-YWGQGTQVTVSS;

wherein
 X1 is K, Q, N, R, D, or E;
 X2 is D, G, E, A, V, L, or I;
 X3 is L, F, W, G, A, V, L, or I;
 X4 is K, R, D, E, N, or Q;
 X5 is V, P, G, A, L, I, or M;
 X6 is T, A, S, G, V, L, or I;
 X7 is E, G, D, A, V, L, or I;
 X8 is P, A, M, G, V, L, or I;
 X9 is T, or S;
 X10 is A, S, M, G, V, L, or I;
 X11 is L, V, G, A, or I;
 X12 is S, N, Q, or T;
 X13 is K, R, D, or E;
 X14 is S, A, T, G, V, L, or I;
 X15 is M, T, V, L, or I;
 X16 is V, G, L, I, or A; and
  wherein for the second antibody CDR1, CDR2, and CDR3 comprise a CDR1, CDR2, and CDR3 combination in any one of rows (d)-(aa) in Table 1.

In various other aspects, the disclosure provides nucleic acids encoding the recombinant antibodies or fusion protein of the disclosure, recombinant expression vectors comprising the nucleic acids of the disclosure operatively linked to a control sequence, recombinant host cell comprising the polypeptides, fusion proteins, dimers, nucleic acids and/or the recombinant expression vectors of the disclosure, and uses of the polypeptides, fusion proteins, kits, dimers, nucleic acids, expression vectors, or host cells of the disclosure for any suitable purpose, including but not limited to drug testing, point of care testing, fusion to detectable domains for easy detection, binding to a solid support for simpler visualization, fused to DNA binding proteins and/or transcription factors to control gene regulation, etc.

In another aspect, the disclosure provides selection methods for designing a CID system, comprising:
 (a) screening a synthetic combinatorial polypeptide library with a ligand of interest to identify ligand binding polypeptides;
 (b) screening a synthetic combinatorial polypeptide library with the ligand-bound polypeptide to identify dimerization polypeptides in the library that (i) bind to the ligand binding polypeptide bound to the ligand, and (ii) do not bind to the ligand binding polypeptide in the absence of the ligand.

In one embodiment, the polypeptide library comprises a synthetic combinatorial immunoglobulin, non-immunoglobulin, or computationally designed library, such as a single-domain antibody library. In another embodiment, the screening in step (a) is carried out 1, 2, 3, 4, 5, 6, or more times. In a further embodiment, the screening in step (b) is carried out 1, 2, 3, 4, 5, 6, or more times. In one embodiment, the ligand is 1000 Da, 950 Da, 900 Da, 850 Da, 800 Da, 750 Da, 700 Da, 650 Da, 600 Da, 550 Da, 500 Da, or less in weight. In another embodiment, the polypeptides, fusion proteins, dimers, or CID systems disclosed herein comprise biosensors that can measure the cellular concentration of specific ligands.

DETAILED DESCRIPTION

Figure 1:
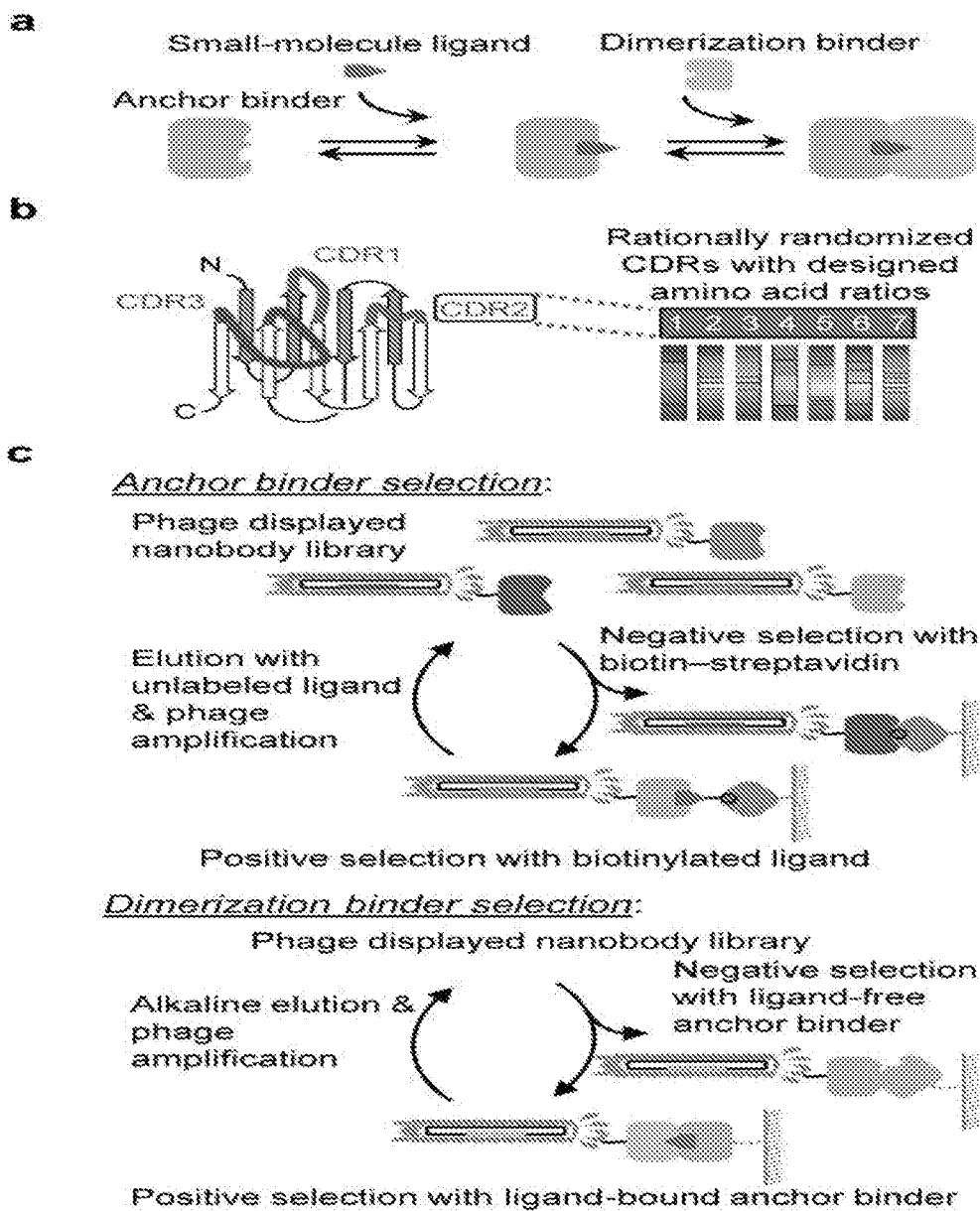
FIG. 1(a)-(c). (a) Ligand-induced dimerization of an anchor binder and a dimerization binder. (b) Schematic of the generation of a synthetic nanobody combinatorial library. (c) Overview of the combinatorial binder library-enabled selection; chemically induced dimerization (COMBINES-CID) method.

All references cited are herein incorporated by reference in their entirety. As used herein, the singular forms "a", "an" and "the" include plural referents unless the context clearly dictates otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In one aspect the disclosure provides recombinant antibodies, comprising a set of complementarity-determining regions (CDRs) selected from the group consisting of a CDR1, CDR2, and CDR3 combination in any one of rows (a)-(aa) in Table 1.

TABLE 1

CDR sequences of anchor and dimerization binder clones identified in the work. Clones selected for CID construction are highlighted in bold

| IDs | | CDR1 | CDR2 | CDR3 |
| --- | --- | --- | --- | --- |
| (a) | CA-14 | SRSRQYD (SEQ ID NO: 1) | SNQDQPP (SEQ ID NO: 2) | FKQHHANGA (SEQ ID NO: 3) |
| (b) | CA-17 | DTSEDYD (SEQ ID NO: 4) | FTSSNHT (SEQ ID NO: 5) | FKKHASFPP (SEQ ID NO: 6) |
| (c) | CA-60 | HTSNAYD (SEQ ID NO: 7) | SFPDAAV (SEQ ID NO: 8) | YKNHPYDPP (SEQ ID NO: 9) |
| (d) | DB-1 | DTYRLDT (SEQ ID NO: 10) | YRTDQDH (SEQ ID NO: 11) | GHSWWDLDE (SEQ ID NO: 12) |
| (e) | DB-2 | TGWEIES (SEQ ID NO: 13) | FRANRFE (SEQ ID NO: 14) | STFDSPSRR (SEQ ID NO: 15) |
| (f) | DB-3 | YTSFQYV (SEQ ID NO: 16) | WLNGQVH (SEQ ID NO: 17) | SMVFDHPQSGGGVET (SEQ ID NO: 18) |
| (g) | DB-4 | YGSDLDS (SEQ ID NO: 19) | YAQDDWV (SEQ ID NO: 20) | MSIWPEQHH (SEQ ID NO: 21) |
| (h) | DB-5 | DSSWWDG (SEQ ID NO: 22) | WAFDNWR (SEQ ID NO: 23) | YTNIDFQAYQSWFQNPPE (SEQ ID NO: 24) |
| (i) | DB-6 | RFSWGEE (SEQ ID NO: 25) | WAATPWQ (SEQ ID NO: 26) | DEWHIGHVS (SEQ ID NO: 27) |
| (j) | DB-7 | YTSDQDA (SEQ ID NO: 28) | SSQSEIA (SEQ ID NO: 29) | YRQSVHPQIASM (SEQ ID NO: 30) |
| (k) | DB-8 | FTFSQEE (SEQ ID NO: 31) | FEDGMGK (SEQ ID NO: 32) | WWYESHPQFQHQ (SEQ ID NO: 33) |

TABLE 1-continued

CDR sequences of anchor and dimerization binder clones identified in the work. Clones selected for CID construction are highlighted in bold

| IDs | | CDR1 | CDR2 | CDR3 |
|---|---|---|---|---|
| (l) | DB-9 | DTFDLSA (SEQ ID NO: 34) | WRDNPFR (SEQ ID NO: 35) | MLQLHHHDG (SEQ ID NO: 36) |
| (m) | DB-10 | DTYNWDV (SEQ ID NO: 37) | YEPSMYT (SEQ ID NO: 38) | MMSSLHTFWANFQSD (SEQ ID NO: 39) |
| (n) | DB-11 | TTSDNDT (SEQ ID NO: 40) | WNGGRDE (SEQ ID NO: 41) | YQDNRSWQE (SEQ ID NO: 42) |
| (o) | DB-12 | GSYSWDA (SEQ ID NO: 43) | YFGHNAY (SEQ ID NO: 44) | VHFWKLLNE (SEQ ID NO: 45) |
| (p) | DB-13 | STYEWYS (SEQ ID NO: 46) | WDEDNWN (SEQ ID NO: 47) | EPQDGWTGV (SEQ ID NO: 48) |
| (q) | DB-14 | YTSAGEI (SEQ ID NO: 49) | WWDGFAL (SEQ ID NO: 50) | AHPSSTKMS (SEQ ID NO: 51) |
| (r) | DB-15 | RFSWGEE (SEQ ID NO: 52) | WATAPWQ (SEQ ID NO: 53) | YEWHIGHVS (SEQ ID NO: 54) |
| (s) | DB-16 | DFSSWDA (SEQ ID NO: 55) | EGHSMTA (SEQ ID NO: 56) | DIEFDLSMNHMYLVQ (SEQ ID NO: 57) |
| (t) | DB-17 | TTSDWYD (SEQ ID NO: 58) | WWPTRAV (SEQ ID NO: 59) | DWSFGMMQQ (SEQ ID NO: 60) |
| (u) | DB-18 | GYSRADD (SEQ ID NO: 61) | FGETDSF (SEQ ID NO: 62) | YHNYTNMFE (SEQ ID NO: 63) |
| (v) | DB-19 | DFYKLYS (SEQ ID NO: 64) | WEAGMSH (SEQ ID NO: 65) | LQDWMREWE (SEQ ID NO: 66) |
| (w) | DB-20 | RFSWGEK (SEQ ID NO: 67) | WAAAPWQ (SEQ ID NO: 68) | DEWRIDHVS (SEQ ID NO: 69) |
| (x) | DB-21 | TTYGQTN (SEQ ID NO: 70) | GLQGRDL (SEQ ID NO: 71) | FHDFLRMWE (SEQ ID NO: 72) |
| (y) | DB-22 | DTSNAST (SEQ ID NO: 73) | WSSSPGN (SEQ ID NO: 74) | MDAFHPQAW (SEQ ID NO: 75) |
| (z) | DB-23 | YGSFLDS (SEQ ID NO: 76) | YAKDDGV (SEQ ID NO: 77) | MSIWAEQHH (SEQ ID NO: 78) |
| (aa) | DB-24 | DYSSTEI (SEQ ID NO: 79) | AQPGVQQ (SEQ ID NO: 80) | NVARFRHNHD (SEQ ID NO: 81) |

As described in the attached appendices, the polypeptides disclosed herein can be used, for example, as part of a chemically induced dimerization (CID) system, in which two recombinant antibodies dimerize only in the presence of cannabidiol.

As disclosed herein, "antibody" refers to immunoglobulin molecules and immunologically active portions of immunoglobulin molecules, i.e., molecules that contain the one of the listed CRD sets and binds to cannabidiol, as described in detail in the attached appendices. As such, the term antibody encompasses not only whole antibody molecules, but also antibody fragments as well as variants (including derivatives) of antibodies and antibody fragments. Such antibody or antibody fragments thereof may include, but are not limited to monoclonal antibodies, humanized antibodies, chimeric antibodies, Fab', F(ab')$_2$, Fab, Fv, rIgG, recombinant single chain Fv fragments (scFv), single-chain antibodies (nanobodies), bivalent or bispecific molecules, diabodies, triabodies, and tetrabodies. In one specific embodiment, the antibody comprises a single-chain antibody.

The recombinant antibodies may comprise a suitable scaffold sequence by which to present the 3 CDRs. Any scaffold sequence may be used, as deemed suitable for an intended use. In one embodiment, the antibody comprises a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

```
                                    (SEQ ID NO: 82)
EVQLQASGGGFVQPGGSLRLSCAASG-(CDR1)-MGWFRQAPGKEREFVS

AIS-(CDR2)-YYADSVKGRFTISRDNSKNTVYLQMNSLRAEDTATYYC

A-(CDR3)-YWGQGTQVTVSS
```

In another embodiment, the antibody comprises a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6P

X7KEREFVSAIS-(CDR2)-YYX8DX9VKGRFTISRDNX10KNTX11Y

LQMX12SLX13X14EDTAX15YYCX16-(CDR3)-YWGQGTQVTVSS;

wherein
X1 is K, Q, N, R, D, or E;
X2 is D, G, E, A, V, L, or I;
X3 is L, F, W, G, A, V, L, or I;
X4 is K, R, D, E, N, or Q;
X5 is V, P, G, A, L, I, or M;
X6 is T, A, S, G, V, L, or I;
X7 is E, G, D, A, V, L, or I;
X8 is P, A, M, G, V, L, or I;
X9 is T, or S;
X10 is A, S, M, G, V, L, or I;
X11 is L, V, G, A, or I;
X12 is S, N, Q, or T;
X13 is K, R, D, or E;
X14 is S, A, T, G, V, L, or I;
X15 is M, T, V, L, or I;
X16 is V, G, L, I, or A.

In each of these embodiments, the CDR1, CDR2, and CDR3 may be a set of any of those provided in Table 1 (i.e.: the combination CDR1+CDR2+CDR3 from any single row). The defined sequences comprise a camelid-based universal scaffold, with the three variable complementarity-determining regions (CDRs) interspersed (see FIG. 1b).

In one embodiment, the percent identity requirement is based only on the scaffold sequence (i.e.: not including identity with the CDR sequence). In another embodiment, the percent identity requirement is based on the scaffold sequence and a set of CDRs.

The polypeptides can tolerate significant substitutions, particularly in the scaffold residues. In some embodiments, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are known. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gin (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gin; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gin or into H is; Asp into Glu; Cys into Ser; Gln into Asn; Glu into Asp; Gly into Ala or into Pro; His into Asn or into Gin; Ile into Leu or into Val; Leu into Ile or into Val; Lys into Arg, into Gin or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In all of these embodiments, the percent identity requirement does not include any additional functional domain that may be incorporated in the polypeptide.

In one embodiment of any of the above embodiments, the set of CDRs comprises a set of complementarity-determining regions (CDRs) selected from the group consisting of a CDR1, CDR2, and CDR3 combination in any one of rows (a), (i), (n), (u), and (x) in Table 1. These specific embodiments are shown in Table 2.

TABLE 2

| IDs | | CDR1 | CDR2 | CDR3 |
|---|---|---|---|---|
| (a) | CA-14 | STSRQYD (SEQ ID NO: 1) | SNQDQPP (SEQ ID NO: 2) | FKQHHANGA (SEQ ID NO: 3) |
| (i) | DB-6 | RFSWGEE (SEQ ID NO: 25) | WAATPWQ (SEQ ID NO: 26) | DEWHIGHVS (SEQ ID NO: 27) |
| (n) | DB-11 | TTSDNDT (SEQ ID NO: 40) | WNGGRDE (SEQ ID NO: 41) | YQDNRSWQE (SEQ ID NO: 42) |
| (u) | DB-18 | GYSRADD (SEQ ID NO: 61) | FGETDSF (SEQ ID NO: 62) | YHNYTNMFE (SEQ ID NO: 63) |
| (x) | DB-21 | TTYGQTN (SEQ ID NO: 70) | GLQGRDL (SEQ ID NO: 71) | FHDFLRMWE (SEQ ID NO: 72) |

In another embodiment of any of the above embodiments, the antibodies further comprise one or more functional domains.

As used herein, a "functional domain" is any polypeptide of interest that might be fused or covalently bound to the polypeptides of the disclosure. In non-limiting embodiments, such functional domains may comprise one or more polypeptide antigens, polypeptide therapeutics, enzymes, detectable domains (ex: fluorescent proteins or fragments thereof), DNA binding proteins, transcription factors, etc. The one or more functional domains may be fused at any appropriate regions within the polypeptides of the disclosure, including but not limited to at the N-terminus or at the C-terminus of the polypeptide.

In a further embodiment, the recombinant antibodies are bound to a solid support. Any suitable solid support may be used, including but not limited to paper, nitrocellulose, beads, cell culture plates, nanoparticles, etc.

In another aspect, the disclosure provides fusion proteins, comprising:
 (a) a first recombinant antibody, comprising the set of complementarity determining regions (CDRs) of SEQ ID NO: 1, 2, and 3;

| IDs | | CDR1 | CDR2 | CDR3 |
|---|---|---|---|---|
| (a) | CA-14 | STSRQYD (SEQ ID NO: 1) | SNQDQPP (SEQ ID NO: 2) | FKQHHANGA (SEQ ID NO: 3) |

(b) a second recombinant antibody, comprising a set of complementarity determining regions (CDRs) selected from the group consisting of a CDR1, CDR2, and CDR3 combination in any one of rows (d)-(aa) in Table 1 (reproduced below in relevant part as Table 3):

TABLE 3

| | ID | CDR1 | CDR2 | CDR3 |
|---|---|---|---|---|
| (d) | DB-1 | DTYRLDT (SEQ ID NO: 10) | YRTDQDH (SEQ ID NO: 11) | GHSWWDLDE (SEQ ID NO: 12) |
| (e) | DB-2 | TGWEIES (SEQ ID NO: 13) | FRANRFE (SEQ ID NO: 14) | STFDSPSRR (SEQ ID NO: 15) |
| (f) | DB-3 | YTSFQYV (SEQ ID NO: 16) | WLNGQVH (SEQ ID NO: 17) | SMVFDHPQSGGGVET (SEQ ID NO: 18) |
| (g) | DB-4 | YGSDLDS (SEQ ID NO: 19) | YAQDDWV (SEQ ID NO: 20) | MSIWPEQHH (SEQ ID NO: 21) |
| (h) | DB-5 | DSSWWDG (SEQ ID NO: 22) | WAFDNWR (SEQ ID NO: 23) | YTNIDFQAYQSWFQNPPE (SEQ ID NO: 24) |
| (i) | DB-6 | RFSWGEE (SEQ ID NO: 25) | WAATPWQ (SEQ ID NO: 26) | DEWHIGHVS (SEQ ID NO: 27) |
| (j) | DB-7 | YTSDQDA (SEQ ID NO: 28) | SSQSEIA (SEQ ID NO: 29) | YRQSVHPQIASM (SEQ ID NO: 30) |
| (k) | DB-8 | FTFSQEE (SEQ ID NO: 31) | FEDGMKG (SEQ ID NO: 32) | WWYESHPQFQHQ (SEQ ID NO: 33) |
| (l) | DB-9 | DTFDLSA (SEQ ID NO: 34) | WRDNPFR (SEQ ID NO: 35) | MLQLHHHDG (SEQ ID NO: 36) |
| (m) | DB-10 | DTYNWDV (SEQ ID NO: 37) | YEPSMYT (SEQ ID NO: 38) | MMSSLHTFWANFQSD (SEQ ID NO: 39) |
| (n) | DB-11 | TTSDNDT (SEQ ID NO: 40) | WNGGRDE (SEQ ID NO: 41) | YQDNRSWQE (SEQ ID NO: 42) |
| (o) | DB-12 | GSYSWDA (SEQ ID NO: 43) | YFGHNAY (SEQ ID NO: 44) | VHFWKLLNE (SEQ ID NO: 45) |
| (p) | DB-13 | STYEWYS (SEQ ID NO: 46) | WDEDNWN (SEQ ID NO: 47) | EPQDGWTGV (SEQ ID NO: 48) |
| (q) | DB-14 | YTSAGEI (SEQ ID NO: 49) | WWDGFAL (SEQ ID NO: 50) | AHPSSTKMS (SEQ ID NO: 51) |
| (r) | DB-15 | RFSWGEE (SEQ ID NO: 52) | WATAPWQ (SEQ ID NO: 53) | YEWHIGHVS (SEQ ID NO: 54) |
| (s) | DB-16 | DFSSWDA (SEQ ID NO: 55) | EGHSMTA (SEQ ID NO: 56) | DIEFDLSMNHMYLVQ (SEQ ID NO: 57) |
| (t) | DB-17 | TTSDWYD (SEQ ID NO: 58) | WWPTRAV (SEQ ID NO: 59) | DWSFGMMQQ (SEQ ID NO: 60) |
| (u) | DB-18 | GYSRADD (SEQ ID NO: 61) | FGETDSF (SEQ ID NO: 62) | YHNYTNMFE (SEQ ID NO: 63) |
| (v) | DB-19 | DFYKLYS (SEQ ID NO: 64) | WEAGMSH (SEQ ID NO: 65) | LQDWMREWE (SEQ ID NO: 66) |
| (w) | DB-20 | RFSWGEK (SEQ ID NO: 67) | WAAAPWQ (SEQ ID NO: 68) | DEWRIDHVS (SEQ ID NO: 69) |
| (x) | DB-21 | TTYGQTN (SEQ ID NO: 70) | GLQGRDL (SEQ ID NO: 71) | FHDFLRMWE (SEQ ID NO: 72) |
| (y) | DB-22 | DTSNAST (SEQ ID NO: 73) | WSSSPGN (SEQ ID NO: 74) | MDAFHPQAW (SEQ ID NO: 75) |
| (z) | DB-23 | YGSFLDS (SEQ ID NO: 76) | YAKDDGV (SEQ ID NO: 77) | MSIWAEQHH (SEQ ID NO: 78) |
| (aa) | DB-24 | DYSSTEI (SEQ ID NO: 79) | AQPGVQQ (SEQ ID NO: 80) | NVAFRHNHD (SEQ ID NO: 81) | and (c) a linker between the first antibody and the second antibody.

In this embodiment, the fusion protein comprises a fused chemically-induced dimerization (CID) system, in which two recombinant antibodies dimerize only in the presence of cannabidiol.

The linker may be of any suitable length and amino acid composition. In various non-limiting embodiment, the linkers may be between 1-200, 2-200, 3-175, 3-150, 3-125, 3-100, 3-75, 3-50, 3-40, 3-30, 3-25, 3-20, 3-15, or 3-10 amino acids in length.

In one embodiment, the second recombinant antibody comprises a set of complementarity determining regions (CDRs) selected from the group consisting of a CDR1, CDR2, and CDR3 combination in any one of rows (i), (n), (u), and (x) in Table 1. These specific embodiments are shown in Table 4.

TABLE 4

| IDs | | CDR1 | CDR2 | CDR3 |
|---|---|---|---|---|
| (i) | DB-6 | RFSWGEE (SEQ ID NO: 25) | WAATPWQ (SEQ ID NO: 26) | DEWHIGHVS (SEQ ID NO: 27) |
| (n) | DB-11 | TTSDNDT (SEQ ID NO: 40) | WNGGRDE (SEQ ID NO: 41) | YQDNRSWQE (SEQ ID NO: 42) |
| (u) | DB-18 | GYSRADD (SEQ ID NO: 61) | FGETDSF (SEQ ID NO: 62) | YHNYTNMFE (SEQ ID NO: 63) |
| (x) | DB-21 | TTYGQTN (SEQ ID NO: 70) | GLQGRDL (SEQ ID NO: 71) | FHDFLRMWE (SEQ ID NO: 72) |

In one embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 82)
EVQLQASGGGFVQPGGSLRLSCAASG-(CDR1)-MGWFRQAPGKEREF

VSAIS-(CDR2)-YYADSVKGRFTISRDNSKNTVYLQMNSLRAEDTAT

YYCA-(CDR3)-YWGQGTQVTVSS wherein for the second antibody CDR1, CDR2, and CDR3 comprise a CDR1, CDR2, and CDR3 combination in any one of rows (d)-(aa) in Table 1.

In another embodiment, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6P

X7KEREFVSAIS-(CDR2)-YYX8DX9VKGRFTISRDNX10KNTX11Y

LQMX12SLX13X14EDTAX15YYCX16-(CDR3)-YWGQGTQVTVSS;

wherein
X1 is K, Q, N, R, D, or E;
X2 is D, G, E, A, V, L, or I;
X3 is L, F, W, G, A, V, L, or I;
X4 is K, R, D, E, N, or Q;
X5 is V, P, G, A, L, I, or M;
X6 is T, A, S, G, V, L, or I;
X7 is E, G, D, A, V, L, or I;
X8 is P, A, M, G, V, L, or I;
X9 is T, or S;
X10 is A, S, M, G, V, L, or I;
X11 is L, V, G, A, or I;
X12 is S, N, Q, or T;
X13 is K, R, D, or E;
X14 is S, A, T, G, V, L, or I;
X15 is M, T, V, L, or I;
X16 is V, G, L, I, or A.
  wherein for the second antibody CDR1, CDR2, and CDR3 comprise a CDR1, CDR2, and CDR3 combination in any one of rows (d)-(aa) in Table 1.

In each of these embodiments, the CDR1, CDR2, and CDR3 may be a set of any of those provided in Table 1, 2, 3, or 4 (i.e.: the combination CDR1+CDR2+CDR3 from any single row). The defined sequences comprise a camelid-based universal scaffold, with the three variable complementarity-determining regions (CDRs) interspersed (see FIG. 1b).

In one embodiment, the percent identity requirement is based only on the scaffold sequence (i.e.: not including identity with the CDR sequence). In another embodiment, the percent identity requirement is based on the scaffold sequence and a set of CDRs as recited.

In another aspect, the disclosure provides kit, comprising:
  (a) a first recombinant antibody, comprising the set of complementarity determining regions (CDRs) of SEQ ID NO:1, 2, and 3;

| IDs | CDR1 | CDR2 | CDR3 |
|---|---|---|---|
| (a) CA-14 | STSRQYD (SEQ ID NO: 1) | SNQDQPP (SEQ ID NO: 2) | FKQHHANGA (SEQ ID NO: 3) |

(b) a second recombinant antibody, comprising a set of complementarity determining regions (CDRs) selected from the group consisting of a CDR1, CDR2, and CDR3 combination in any one of rows (d)-(aa) in Table 1 (reproduced above in relevant part as Table 3); and
  (c) cannabidiol, or a salt thereof.

As described in the attached appendices, the kits disclosed herein can be used, for example, as a chemically induced dimerization (CID) system, in which two recombinant antibodies dimerize only in the presence of cannabidiol.

In one embodiment of the kits, the second recombinant antibody comprises a set of complementarity determining regions (CDRs) selected from the group consisting of a CDR1, CDR2, and CDR3 combination in any one of rows (i), (n), (u), and (x) in Table 1. These specific embodiments are shown in Table 4.

In one embodiment of the kits, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 82)
EVQLQASGGGFVQPGGSLRLSCAASG-(CDR1)-MGWFRQAPGKEREF

VSAIS-(CDR2)-YYADSVKGRFTISRDNSKNTVYLQMNSLRAEDTAT

YYCA-(CDR3)-YWGQGTQVTVSS wherein for the second antibody CDR1, CDR2, and CDR3 comprise a CDR1, CDR2, and CDR3 combination in any one of rows (d)-(aa) in Table 1. In another embodiment of the kits, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EVX1LQASGGX2X3VQPGGSLRLSX4AASG-(CDR1)-MGWX5RQX6P

X7KEREFVSAIS-(CDR2)-YYX8DX9VKGRFTISRDNX10KNTX11Y

LQMX12SLX13X14EDTAX15YYCX16-(CDR3)-YWGQGTQVTVSS;

wherein
X1 is K, Q, N, R, D, or E;
X2 is D, G, E, A, V, L, or I;
X3 is L, F, W, G, A, V, L, or I;
X4 is K, R, D, E, N, or Q;
X5 is V, P, G, A, L, I, or M;
X6 is T, A, S, G, V, L, or I;
X7 is E, G, D, A, V, L, or I;
X8 is P, A, M, G, V, L, or I;
X9 is T, or S;
X10 is A, S, M, G, V, L, or I;
X11 is L, V, G, A, or I;
X12 is S, N, Q, or T;
X13 is K, R, D, or E;
X14 is S, A, T, G, V, L, or I;
X15 is M, T, V, L, or I;
X16 is V, G, L, I, or A.
  wherein for the second antibody CDR1, CDR2, and CDR3 comprise a CDR1, CDR2, and CDR3 combination in any one of rows (d)-(aa) in Table 1. In each of these embodiments, the CDR1, CDR2, and CDR3 may be a set of any of those provided in Table 1, 2, 3, or 4 (i.e.: the combination CDR1+CDR2+CDR3 from any single row). The defined sequences comprise a camelid-based universal scaffold, with the three variable complementarity-determining regions (CDRs) interspersed (see FIG. 1b).

In one embodiment of the kits, the percent identity requirement is based only on the scaffold sequence (i.e.: not including identity with the CDR sequence). In another embodiment, the percent identity requirement is based on the scaffold sequence and a set of CDRs.

In another aspect, the disclosure provides dimers comprising:
(a) a first recombinant antibody, comprising the set of complementarity determining regions (CDRs) of SEQ ID NO:1, 2, and 3;

| IDs | CDR1 | CDR2 | CDR3 |
| --- | --- | --- | --- |
| (a) CA-14 | STSRQYD (SEQ ID NO: 1) | SNQDQPP (SEQ ID NO: 2) | FKQHHANGA (SEQ ID NO: 3) |

(b) a second recombinant antibody, comprising a set of complementarity determining regions (CDRs) selected from the group consisting of a CDR1, CDR2, and CDR3 combination in any one of rows (d)-(aa) in Table 1 (reproduced above in relevant part as Table 3); and
(c) cannabidiol, or a salt thereof, wherein the first recombinant antibody and the second recombinant antibody dimerize in the presence of cannabidiol.

In one embodiment of the dimers, the second recombinant antibody comprises a set of complementarity determining regions (CDRs) selected from the group consisting of a CDR1, CDR2, and CDR3 combination in any one of rows (i), (n), (u), and (x) in Table 1. These specific embodiments are shown in Table 4.

In one embodiment of the dimers, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 82)
EVQLQASGGGFVQPGGSLRLSCAASG-(CDR1)-MGWFRQAPGKEREF

VSAIS-(CDR2)-YYADSVKGRFTISRDNSKNTVYLQMNSLRAEDTAT

YYCA-(CDR3)-YWGQGTQVTVSS wherein for the second antibody CDR1, CDR2, and CDR3 comprise a CDR1, CDR2, and CDR3 combination in any one of rows (d)-(aa) in Table 1. In another embodiment of the dimer, the first antibody and/or the second antibody comprise a scaffold comprising an amino acid sequence at least 40%, 45%, 50%, 55%, 60%, 65%, 70%, 75%, 80%, 85%, 90%, 91%, 92%, 93%, 94%, 95%, 96%, 97%, 98%, 99%, or 100% identical along the length of the amino acid sequence:

(SEQ ID NO: 83)
EV$\underline{X1}$LQASGG$\underline{X2}$$\underline{X3}$VQPGGSLRLS$\underline{X4}$AASG-(CDR1)-MGW$\underline{X5}$RQ$\underline{X6}$P $\underline{X7}$KEREFVSAIS-(CDR2)-YY$\underline{X8}$D$\underline{X9}$VKGRFTISRDN$\underline{X10}$KNT$\underline{X11}$Y LQM$\underline{X12}$SL$\underline{X13}$$\underline{X14}$EDTA$\underline{X15}$YYC$\underline{X16}$-(CDR3)-YWGQGTQVTVSS;

wherein
$X1$ is K, Q, N, R, D, or E;
$X2$ is D, G, E, A, V, L, or I;
$X3$ is L, F, W, G, A, V, L, or I;
$X4$ is K, R, D, E, N, or Q,
$X5$ is V, P, G, A, L, I, or M;
$X6$ is T, A, S, G, V, L, or I;
$X7$ is E, G, D, A, V, L, or I;
$X8$ is P, A, M, G, V, L, or I;
$X9$ is T, or S;
$X10$ is A, S, M, G, V, L, or I;
$X11$ is L, V, G, A, or I;
$X12$ is S, N, Q, or T;
$X13$ is K, R, D, or E;
$X14$ is S, A, T, G, V, L, or I;
$X15$ is M, T, V, L, or I;
$X16$ is V, G, L, I, or A.

wherein for the second antibody CDR1, CDR2, and CDR3 comprise a CDR1, CDR2, and CDR3 combination in any one of rows (d)-(aa) in Table 1. In each of these embodiments, the CDR1, CDR2, and CDR3 may be a set of any of those provided in Table 1, 2, 3, or 4 (i.e.: the combination CDR1+CDR2+CDR3 from any single row). The defined sequences comprise a camelid-based universal scaffold, with the three variable complementarity-determining regions (CDRs) interspersed (see FIG. 1b).

In one embodiment of the dimers, the percent identity requirement is based only on the scaffold sequence (i.e.: not including identity with the CDR sequence). In another embodiment, the percent identity requirement is based on the scaffold sequence and a set of CDRs.

The polypeptides and antibodies of the disclosure may include additional residues at the N-terminus, C-terminus, internal to the polypeptide, or a combination thereof; these additional residues are not included in determining the percent identity of the polypeptides of the invention relative to the reference polypeptide. Such residues may be any residues suitable for an intended use, including but not limited to detectable proteins or fragments thereof (also referred to as "tags"). As used herein, "tags" include general detectable moieties (i.e.: fluorescent proteins, antibody epitope tags, etc.), therapeutic agents, purification tags (His tags, etc.), linkers, ligands suitable for purposes of purification, ligands to drive localization of the polypeptide, peptide domains that add functionality to the polypeptides, etc.

As used throughout the present application, the term "polypeptide", "peptide", and "protein" are used interchangeably in their broadest sense to refer to a sequence of subunit amino acids of any length, which can include genetically coded and non-genetically coded amino acids, chemically or biochemically modified or derivatized amino acids, and polypeptides having modified peptide backbones. The polypeptides of the invention may comprise L-amino acids+glycine, D-amino acids+glycine (which are resistant to L-amino acid-specific proteases in vivo), or a combination of D- and L-amino acids+glycine. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In another aspect, the disclosure provides nucleic acids encoding the recombinant antibody or fusion protein of any embodiment or combination of embodiments of the disclosure. The nucleic acid sequence may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In another aspect, the disclosure provides recombinant expression vector comprising the nucleic acid of the disclosure operatively linked to a control sequence. "Expression vector" includes vectors that operatively link a nucleic acid coding region or gene to any control sequences capable of effecting expression of the gene product. "Control sequences" operatively linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In a further aspect, the disclosure provides host cells that comprise the nucleic acids or expression vectors (i.e.: episomal or chromosomally integrated) disclosed herein, wherein the host cells can be either prokaryotic or eukaryotic. The cells can be transiently or stably engineered to incorporate the expression vector of the disclosure, using techniques including but not limited to bacterial transformations, calcium phosphate co-precipitation, electroporation, or liposome mediated-, DEAE dextran mediated-, polycationic mediated-, or viral mediated transfection.

In one aspect, the disclosure provides methods for use of the polypeptides, fusion proteins, kits, dimers, nucleic acid, expression vector, or host cell of any embodiment or combination of embodiments disclosed herein for any suitable purpose, including but not limited to drug testing, point of care testing, fusion to detectable domains for easy detection, binding to a solid support for simpler visualization, fused to DNA binding proteins and/or transcription factors to control gene regulation, etc. As shown in the examples that follow, the inventors have demonstrated that CID systems induced by cannabidiol with high ligand selectivity, and which have sensitivity (in a sandwich ELISA-like assay) of cannabidiol in body fluids with a detection limit of ~0.25 ng/mL. Thus, in one embodiment, the methods are used to detect cannabidiol in body fluids from a subject (such as a human subject).

In another aspect, the disclosure provides methods for making chemically induced dimerization (CID) systems, where two polypeptides only dimerize in the presence of a small-molecule ligand. The methods are described in detail in the examples which follow. Such CID systems may be constructed using two polypeptides selected from a vastly diverse synthetic combinatorial library. The combinatorial library may comprise DNA sequences chemically synthesized by a combinatorial method, such as a trinucleotide mutagenesis technology (PMID: 7838712), to obtain the diversity higher than $10^9$. The DNA sequences may encode polypeptides consisting of a consensus sequence, typically providing a structural scaffold, such as an immunoglobulin, non-immunoglobulin (PMID: 25931178), or computationally designed scaffold, and variable loop sequences, similar to complementarity determining regions (CDRs) of antibodies, which are structurally flexible and thus can be rationally randomized by incorporating a combination of amino acids under a given ratio into each loop sequence positions. Since both the polypeptides that form a CID system can be selected from a combinatorial library, this selection method may be applicable to generate CID systems for a wide range of small-molecule ligands. These methods are a significant improvement over prior methods which rely on the using existing polypeptide-ligand complexes as a target to search for a dimerization polypeptide, and thus have limited choices of ligands.

The dimerization specificity, i.e., the two polypeptides only form a dimer in the presence of a ligand, may be enhanced by using the flexible loops as the binding site, where the ligand binding triggers a conformational change recognized by a second polypeptide.

Without the conformation change, the second polypeptide cannot dimerize with the first polypeptide. In one embodiment, the methods comprise
  (a) screening a synthetic combinatorial polypeptide library with a ligand of interest to identify ligand binding polypeptides;
  (b) screening a synthetic combinatorial polypeptide library with the ligand-bound polypeptide to identify dimerization polypeptides in the library that (i) bind to the ligand binding polypeptide bound to the ligand, and (ii) do not bind to the ligand binding polypeptide in the absence of the ligand. In one embodiment, the polypeptide library may comprise a synthetic combinatorial immunoglobulin, non-immunoglobulin, or computationally designed library, such as a single-domain antibody library. In another embodiment, the screening in step (a) is carried out 1, 2, 3, 4, 5, 6, or more times. In a further embodiment, the screening in step (b) is carried out 1, 2, 3, 4, 5, 6, or more times. In one embodiment, the ligand is 1000 Da, 950 Da, 900 Da, 850 Da, 800 Da, 750 Da, 700 Da, 650 Da, 600 Da, 550 Da, 500 Da, or less in weight. The methods may further comprise any other suitable steps, including but not limited to any step or combination of steps disclosed in the examples that follow.

In one embodiment of the uses and/or CID systems disclosed herein, the polypeptides, fusion proteins, dimers, or CID systems comprise biosensors that can measure the cellular concentration of specific ligands.

EXAMPLES

Chemically induced dimerization (CID) systems, in which two proteins dimerize only in the presence of a small molecule ligand, offer versatile tools for small molecule sensing and actuation. However, only a handful of CID systems exist and creating one with the desired sensitivity and specificity for any given ligand is an unsolved problem. Here, we developed a combinatorial binders-enabled selection of CID (COMBINES-CID) method broadly applicable to different ligands. We demonstrated a proof-of-principle by generating a nanobody-based heterodimerization systems induced by cannabidiol with high ligand selectivity. We applied the CID system to a sensitive sandwich ELISA-like assay of cannabidiol in body fluids with a detection limit of ~0.25 ng/mL. COMBINES-CID provides an efficient, cost-effective solution for expanding the biosensor toolkit for small-molecule detection.

Creating CID systems for new ligands is an unsolved problem. Here we propose a COMBINES-CID method to select CID proteins for any given ligand—an 'anchor binder' that first binds to a ligand, and a 'dimerization binder' that only binds to the anchor binder—ligand complex not the unbound anchor binder (FIG. 1a). This method is based on the in vitro selection of vastly diverse protein binder libraries, such as combinatorial antibody libraries,[16] which can be selected against virtually any epitope. In this work, we focus on a single-domain antibody (or nanobody), a 12-15 kDa functional antibody fragment from camelid comprising a universal scaffold and three variable complementarity-determining regions (CDRs) (FIG. 1b). We reasoned that the three CDR loops might form a binding pocket with adaptable sizes for small-molecule epitopes. Of note, unlike a rigid binding site, the flexible CDR loops might undergo conformational changes upon the ligand binding, providing a basis for the selection of conformationally selective binders only recognizing ligand-bound anchor binders. A stepwise phage-display screening strategy was devised to first obtain anchor binders which were then used as baits to select dimerization binders (FIG. 1c).

As a proof-of-principle, cannabidiol (CBD), a non-psychoactive phytocannabinoid with many medical uses,[22] was chosen as the ligand. Unlike large, polar, or charged ligands that might be easier targets for binder selection, CBD is hydrophobic and smaller than most ligands in all existing CID systems. Thus, CBD provides a rigorous test of our method.

Figure 5:
FIG. 5(a)-(c). (a) Design of the nanobody library sequencing with an Illumina NextSeq™ 2×150 bp paired-end kit. Both ends of amplicons were barcoded by 8-bp unique molecular identifiers. (b) Distribution of unique clone counts in merged sequencing reads. (c) Length distribution of CDR3 in sequenced clones.
Figure 5:
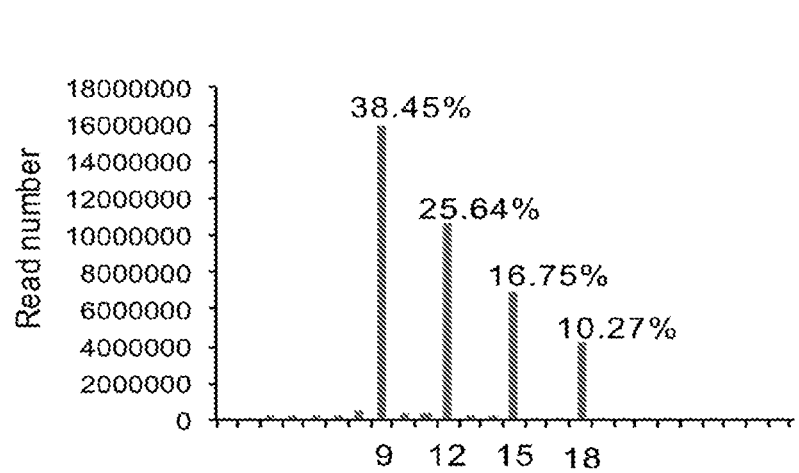

To enhance the success of selection, we prepared a high-quality nanobody library with high protein diversity and stability. A combinatorial gene library, designed with a thermally stable nanobody scaffold and three rationally randomized CDRs, was chemically synthesized by a trinucleotide mutagenesis technology,[25] similarly as previously described.[26] The synthetic DNA library of ~$10^{12}$ sequences was subcloned and transformed into *Escherichia coli* to produce phage-displayed nanobodies. The quality of the phage library was assessed by Sanger and deep sequencing. Approximately 74% of the clones were found within the designed sequences. 39,289,832 out of 41,458,478 merged 2×150 bp paired-end reads were found to be unique (FIG. 5) and the library diversity was estimated to be 1.23 to 7.14× $10^9$ by an empirical Bayesian statistical method.[27] The amino acid distributions of CDRs were close to the expected ratios (data not shown).

Figure 2:
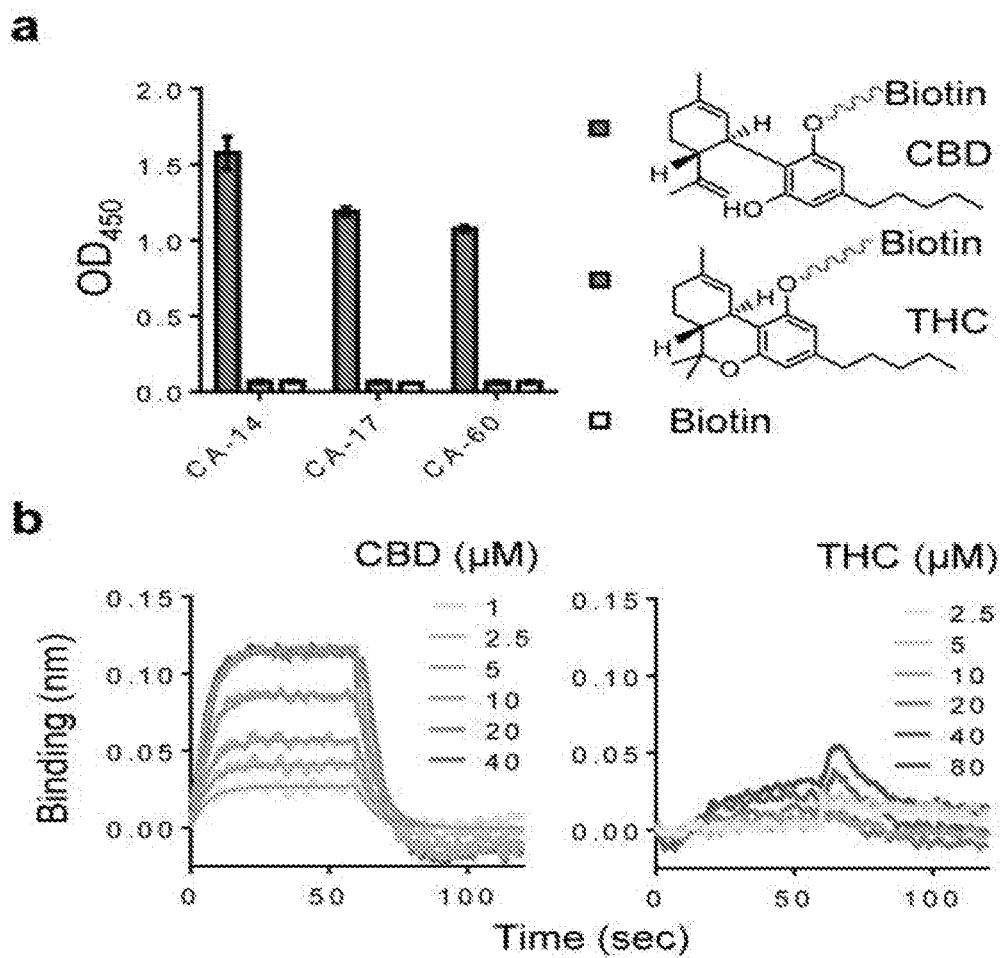
FIG. 2(a)-(b). Anchor binder analysis. (a) Enzyme-linked immunosorbent assay (ELISA) of three anchor binders against biotinylated cannabidiol (CBD) and tetrahydrocannabinol (THC) immobilized on streptavidin-coated plates. Biotin was used as a control. (b) BLI sensorgrams of CA-14 with unlabeled CBD or THC. CA-14 was immobilized on Super Streptavidin biosensors. CBD binding sensorgrams (curves) were modelled using a global fit (lines).
Figure 6:
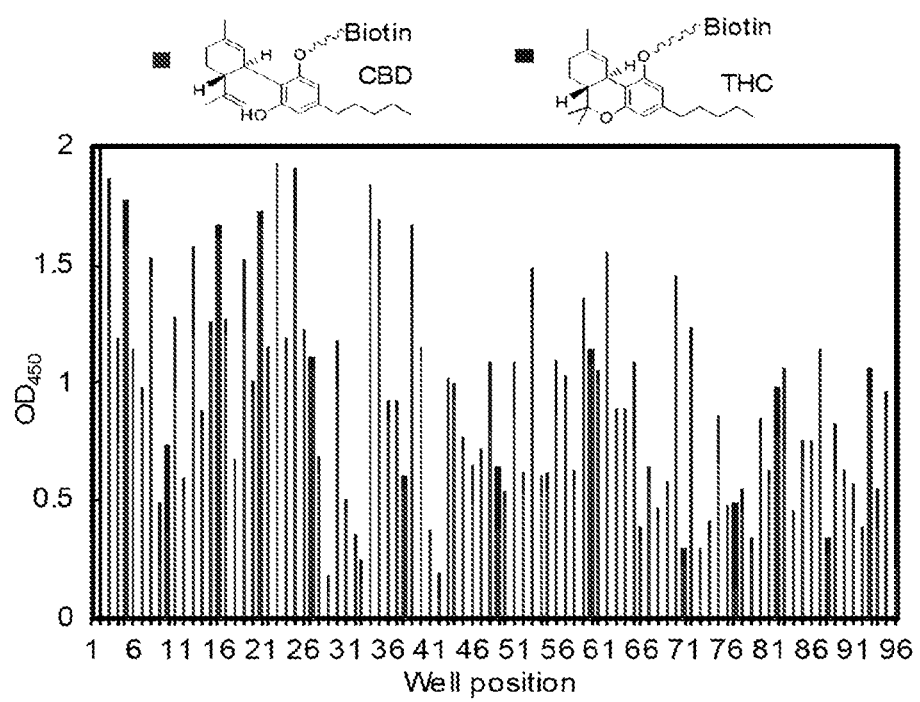
FIG. 6(a)-(b). (a) Enrichment of phage titers following each round of biopanning for the anchor binder selection. (b) ELISA of 96 randomly picked clones after the six rounds of the anchor binder selection.

To obtain CBD anchor binders (CA), the library was screened using biotinylated CBD as bait. Phage displayed nanobodies were captured by biotinylated CBD bound to streptavidin-coated magnetic beads and eluted by unlabeled CBD (FIG. 1c). After six rounds of selection, three unique clones were found from 96 randomly picked clones. Single-phage ELISA showed that all had specific binding to CBD—biotin—streptavidin but minimal binding to its structural analog, tetrahydrocannabinol (THC)—biotin—streptavidin (FIGS. 2a and 6). The binding selectivity suggests that the minor structural difference in CBD (i.e., the open ring with a phenolic hydroxyl group) is key to the molecular recognition. Interestingly, CDRs in the three nanobodies have little or no sequence similarity (Table 1).

Figure 7:
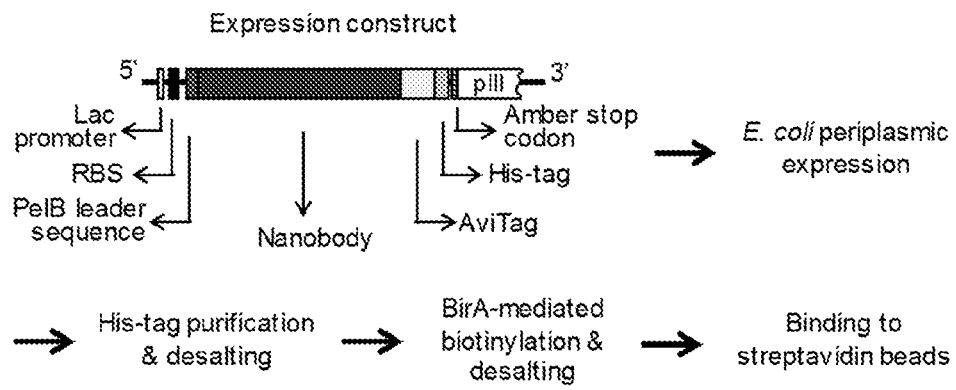
FIG. 7(a)-(c). (a) Schematic of nanobody expression, purification, and biotinylation. SDS-PAGE analysis of free and streptavidin bead-bound anchor (b) and dimerization (c) binders after BirA-mediated biotinylation. The biotinylation efficiency was analyzed by incubating biotinylated nanobodies with streptavidin beads and then comparing the ratio of free to bead-bound nanobodies. Bead-bound nanobodies were eluted by boiling beads in SDS sample loading buffer.
Figure 7:
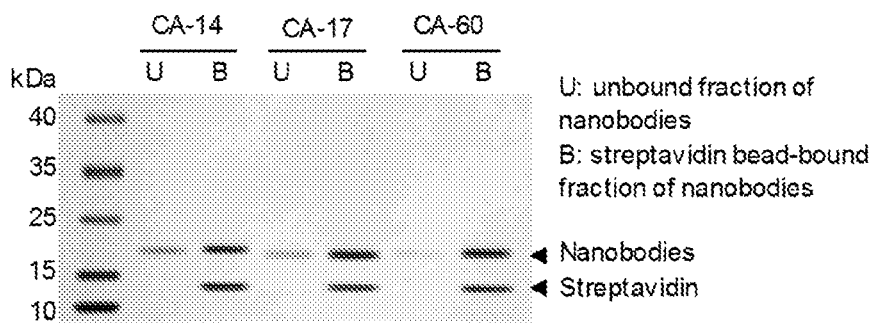
Figure 7:
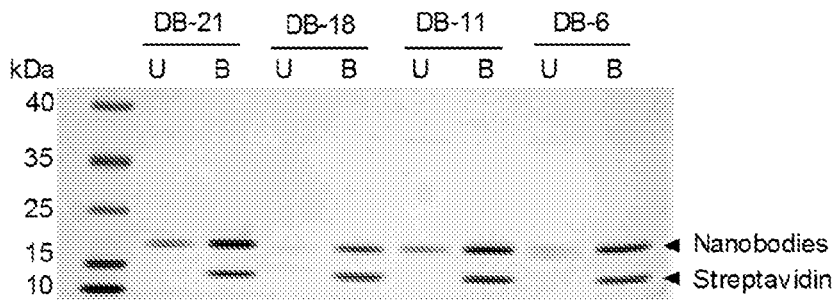

To confirm that the nanobody binding only requires CBD, and not the linker between CBD and biotin or the streptavidin, we measured the binding affinity using unlabeled CBD. Anchor-binder hits were expressed in *E. coli* periplasm and purified by nickel-affinity and size-exclusion chromatography (SEC). Purified nanobodies were enzymatically biotinylated (FIG. 7a-b) and immobilized on streptavidin biosensors to quantify binding affinities to CBD or THC by Bio-Layer Interferometry (BLI) (FIG. 8a). All hits showed high specificity to CBD and dissociation constants (KDs) were measured to be 6.0 (CA-14), 26.4 (CA-17), and 3.5 (CA-60) μM (FIGS. 2b and 8b and 8c).

To select specific ligand-induced dimerization, the library was subjected to negative and positive screening using CBD-free and bound CA-14 as baits, respectively (FIG. 1c). After four rounds of selection, 24 unique clones out of 384 were identified. All these DBs showed CBD concentration-dependent binding to CA-14 by titration ELISA (data not shown). They also showed minimal or no binding to CA-14 in the absence of CBD. Four clones with diverse CDR sequences (Table 1) and high protein expression yields (>2.5 mg per liter of culture) were purified for further characterization.

Figure 3:
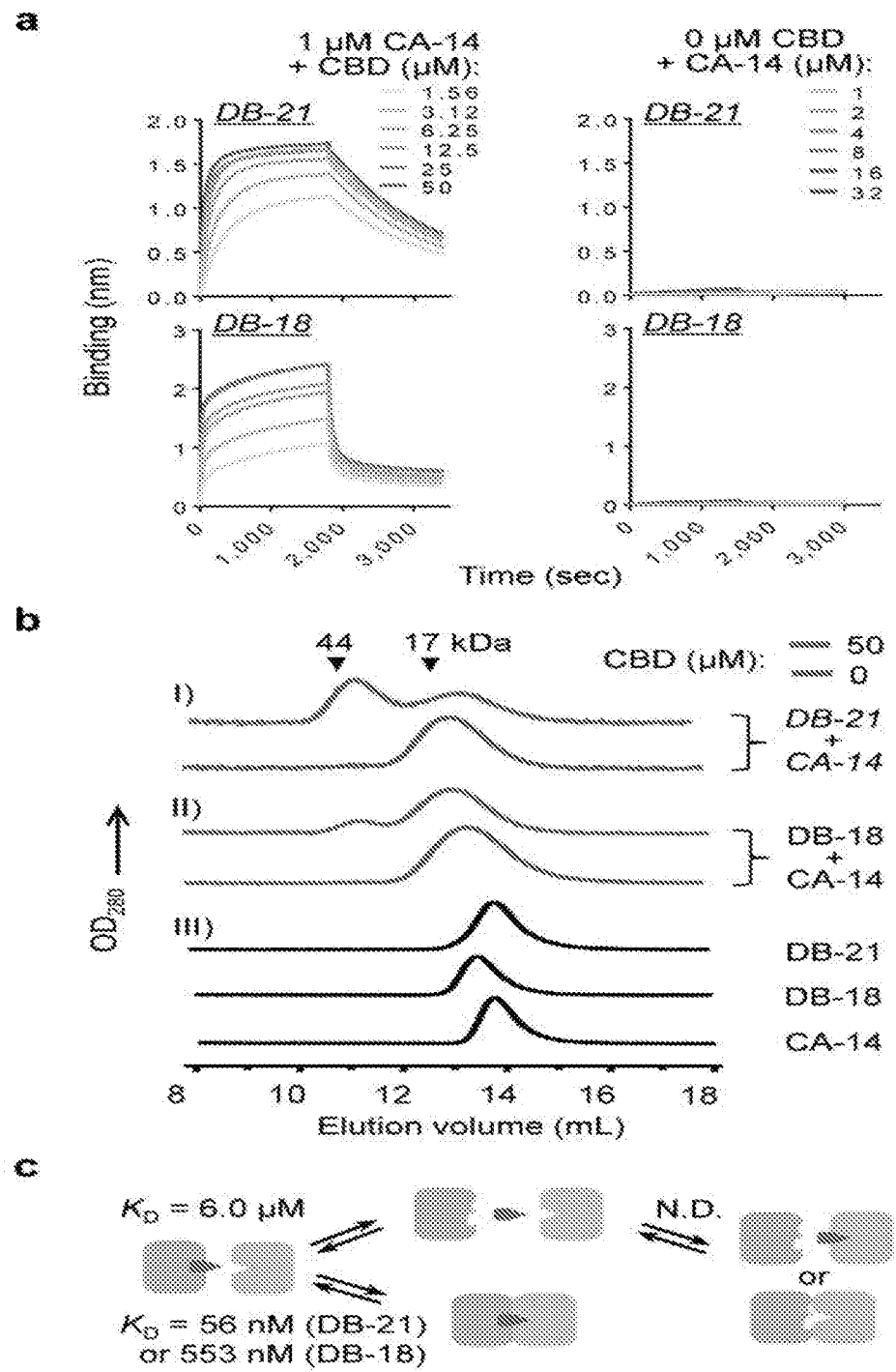
FIG. 3(a)-(c). CBD-induced nanobody dimerization. (a) BLI sensorgrams of DB-21 and DB-18 immobilized on streptavidin biosensors binding to CA-14 preequilibrated with different concentrations of CBD. (b) SEC analysis of CBD-induced heterodimerization. I) 5 µM (each) DB-21 and CA-14 and II) 10 µM (each) DB-18 and CA-14, in the presence or absence of CBD, were crosslinked by 50 µM bis-N-succinimidyl-(pentaethylene glycol) ester for 30 min at room temperature before SEC. III) 30 µM non-crosslinked DB-21, DB18, and CA-14 were separated analyzed. Elution volumes of protein standards are marked by triangles. Chromatograms in different groups are shown with different Y scales. (c) Measured $K_D$s of the ternary complex formation. N.D., not detectable or too weak to be determined.

With the purified DB nanobodies in hand, we first sought to determine their binding affinities to the CA-14-CBD. CBD might directly bind to selected dimerization binders, which can affect the affinity measurement. To rule out this possibility, the four nanobodies were biotinylated (FIG. 7c) and immobilized on streptavidin biosensors, and the interaction with CBD was detected by BLI. Only minimal binding between CBD and the dimerization binders was detected (data not shown). Moreover, the binding-dissociation dynamics of the CA-14-CBD complex can also affect the measurement of dimerization binder affinities. To address this, the affinity was measured by a BLI assay in which the biosensor-immobilized dimerization binders were interacted with CA-14 pre-equilibrated with varied concentrations of CBD (FIG. 9a). The concentrations of the CA-14-CBD complex in equilibrium were calculated based on input CA-14 and CBD concentrations. The CA-14-CBD complex concentration was approximated to be constant because only a minimal fraction of the complex bound to the biosensor tips during the BLI assay. It was confirmed that CA-14 only interacts with the dimerization binders in the presence of CBD (FIG. 3a). The KDs of the four dimerization binders varied from 56.4 nM to 19 μM (Table 5). CA-14 and DB-21 appear to form the most stable CID complex due to a relatively slow dissociation rate ($k_{off}$=6.17×$10^{-4}$/s; Table 5). All binders showed a high ligand specificity and the dimerization was not induced by THC (FIG. 9b).

TABLE 5

Dissociation constants of anchor and dimerization binders in the presence or absence of CBD.

| Dimerization binder ID | CBD | $K_D$ ($10^{-9}$ M) | $K_{on}$ ($10^5$ M$^{-1}$s$^{-1}$) | $K_{off}$ ($10^{-4}$ s$^{-1}$) |
|---|---|---|---|---|
| DB-21 | + | 56.4 | 0.11 | 6.17 |
|  | − | N.D. | N.D. | N.D. |

TABLE 5-continued

Dissociation constants of anchor and dimerization binders in the presence or absence of CBD.

| Dimerization binder ID | CBD | $K_D$ $(10^{-9} M)$ | $K_{on}$ $(10^5 M^{-1}s^{-1})$ | $K_{off}$ $(10^{-4} s^{-1})$ |
|---|---|---|---|---|
| DB-18 | + | 553 | 0.41 | 227 |
|  | − | N.D. | N.D. | N.D. |
| DB-11 | + | 1,380 | 0.61 | 840 |
|  | − | N.D. | N.D. | N.D. |
| DB-6 | + | 19,000 | 0.096 | 1,820 |
|  | − | N.D. | N.D. | N.D. |

Next, we confirmed the CBD-induced heterodimerization of the two most stable CID systems (CA-14-DB-21 and CA-14-DB-18) by analytical SEC. As expected, the anchor and dimerization binders by themselves were detected exclusively as monomers, but after adding CBD, SEC peaks corresponding to the heterodimers were observed (FIG. 3b). These results demonstrate a nanobody-based CID binding mechanism (FIG. 3c), which can be explained by a mathematic model of the three-component binding equilibrium (see below). Our model suggests that dimerization binders stabilize the anchor binder-ligand complex by cooperative binding. Furthermore, Rosetta™-based ligand docking calculations shed in-sight onto the nature of the anchor binder-ligand binding (see below).

Figure 4:
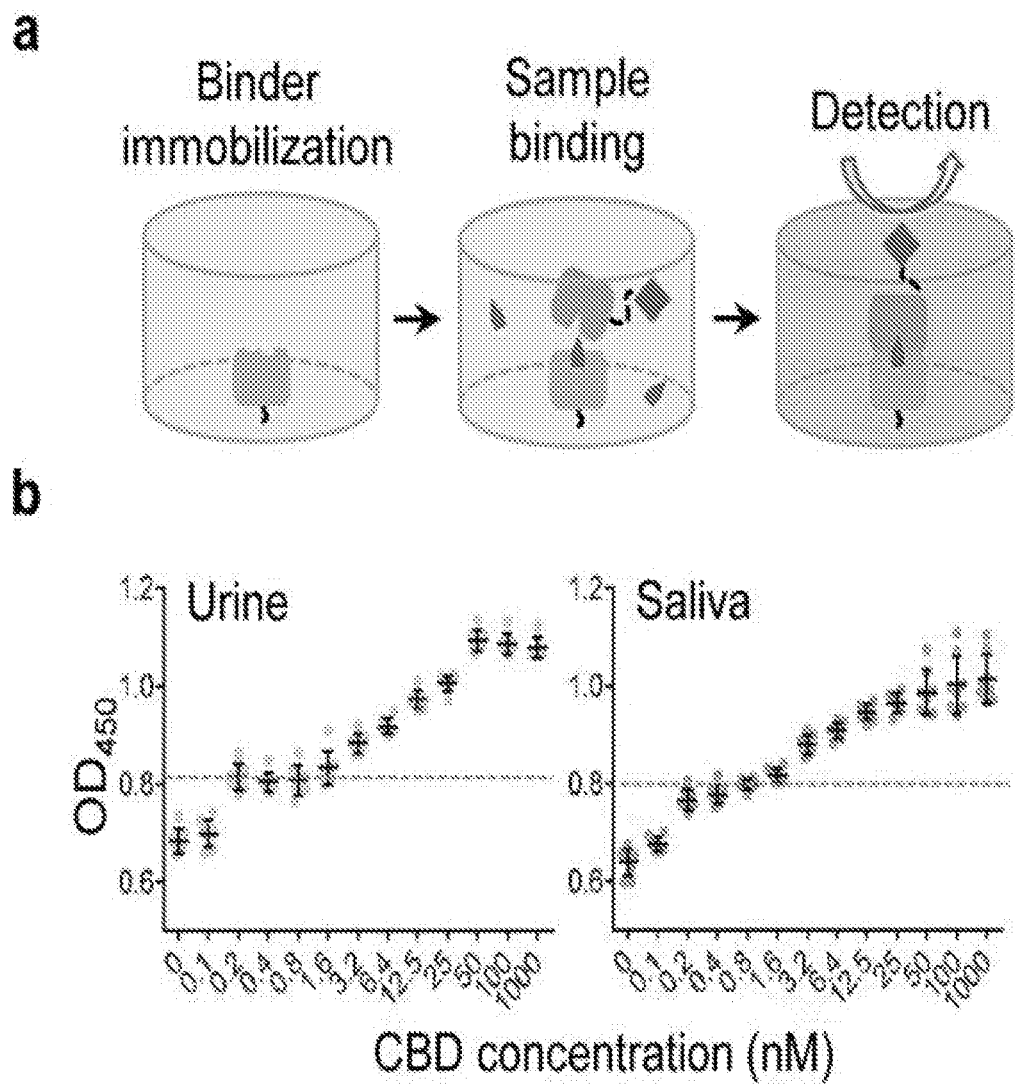
FIG. 4(a)-(b). Sandwich ELISA-like detection of CBD. (a) CA-14 was immobilized on a plate and the CBD-induced binding of DB-21 was detected by a horseradish peroxidase-conjugated antibody. (b) The detection of CBD spiked in urine and saliva samples. Limits of detection (LoDs=mean$_{blank}$+3×(standard deviation of the blank, n=8)) for urine and saliva samples were determined to be ~0.8 nM (~0.25 ng/mL).
Figure 10:
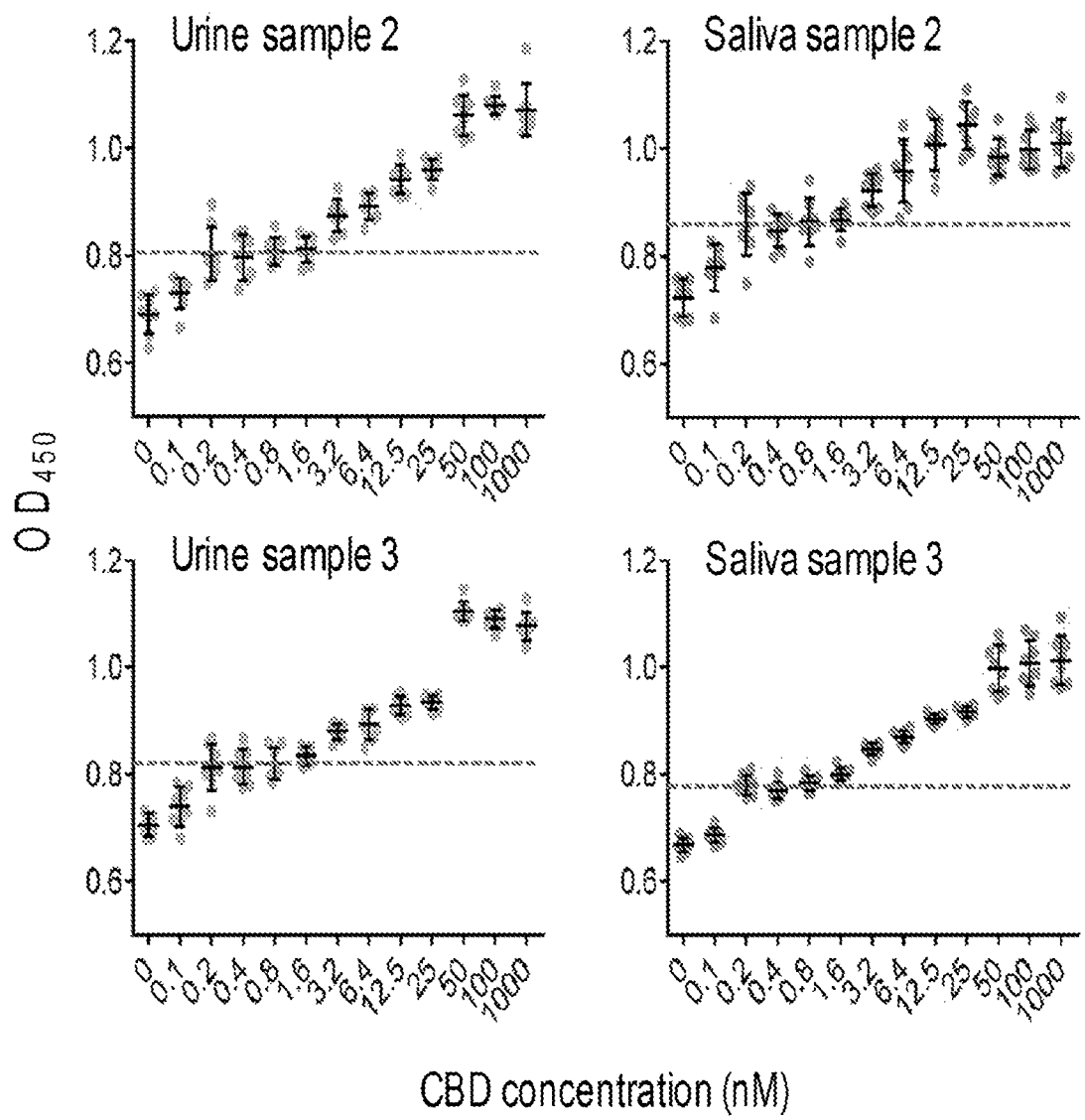
FIG. 10. The sandwich ELISA-like assay of CBD-spiked urine and saliva samples in addition to the samples shown in FIG. 4b. LoD (mean$_{blank}$+3×(standard deviation, SD$_{blank}$) for the urine and saliva samples are ~0.8 nM.

Lastly, to demonstrate the application in in vitro small molecule detection, we applied the CA-14-DB-21 dimerization system to a sandwich ELISA-like assay (FIG. 4a). Traditional ELISA-based small molecule detection relies on the use of ligand-binding antibodies, which are difficult to obtain by animal immunization because small molecules, by themselves, are non-immunogenic and can only elicit antibodies upon conjugation to protein carriers. Moreover, ELISA requires labeling of ligands—i.e., chemical linking of ligands or their competitive inhibitors to solid supports or reporter molecules—and thus, are not generally applicable because some modifications are difficult to chemically synthesize or can affect ligand-binding activity. However, the sandwich ELISA-like detection only requires the labeling of CID proteins. By analyzing CBD-spiked urine and saliva samples, the assay showed a broad detection range with Limit of Detection (LoD) of ~0.8 nM or ~0.25 ng/mL (FIGS. 4b and 10), which meets requirements for the diagnostic applications.[31]

In summary, COMBINES-CID enables the efficient search of a vast protein-protein interactome space for ligand-modulated interactions. We demonstrated for the first time that stable CID systems can be constructed with synthetic nanobodies. Our method is applicable to select protein binders with other immunoglobulin, non-immunoglobulin, or computationally designed scaffolds. The selection is cost-effective and fast since the same combinatorial library can be used for different ligands and high-quality binders were often obtained without in vitro affinity maturation. Together, our results show that this method can generate CID systems for a challenging ligand like CBD. This demonstrates that COMBINES-CID is a suitable method to address the unmet challenge of generating biosensors for highly demanding applications such as point-of-care testing and metabolic engineering.

REFERENCES (1) Spencer, D. M.; Wandless, T. J.; Schreiber, S. L.; Crabtree, G. R. *Science* 1993, 262, 1019.
(2) Rivera, V. M.; Clackson, T.; Natesan, S.; Pollock, R.; Amara, J. F.; Keenan, T.; Magari, S. R.; Phillips, T.; Courage, N. L.; Cerasoli, F.; Holt, D. A.; Gilman, M. *Nat. Med.* 1996, 2, 1028.
(3) Miyamoto, T.; DeRose, R.; Suarez, A.; Ueno, T.; Chen, M.; Sun, T. P.; Wolfgang, M. J.; Mukherjee, C.; Meyers, D. J.; Inoue, T. *Nat. Chem. Biol.* 2012, 8, 465.
(4) Ho, S. N.; Biggar, S. R.; Spencer, D. M.; Schreiber, S. L.; Crabtree, G. R. *Nature* 1996, 382, 822.
(5) Belshaw, P. J.; Ho, S. N.; Crabtree, G. R.; Schreiber, S. L. *Proc. Natl. Acad. Sci. U.S.A* 1996, 93, 4604.
(6) Fegan, A.; White, B.; Carlson, J. C. T.; Wagner, C. R. *Chem. Rev.* 2010, 110, 3315.
(7) DeRose, R.; Miyamoto, T.; Inoue, T. *Pflugers Arch.* 2013, 465, 409.
(8) Hunter, M. M.; Margolies, M. N.; Ju, A.; Haber, E. *J. Immunol.* 1982, 129, 1165.
(9) Bradbury, A. R. M.; Sidhu, S.; Dubel, S.; McCafferty, J. *Nat. Biotechnol.* 2011, 29, 245.
(10) Chen, G.; Hayhurst, A.; Thomas, J. G.; Harvey, B. R.; Iverson, B. L.; Georgiou, G. *Nat. Biotechnol.* 2001, 19, 537.
(11) Tinberg, C. E.; Khare, S. D.; Dou, J. Y.; Doyle, L.; Nelson, J. W.; Schena, A.; Jankowski, W.; Kalodimos, C. G.; Johnsson, K.; Stoddard, B. L.; Baker, D. *Nature* 2013, 501, 212.
(12) Farrar, M. A.; Alberolalla, J.; Perlmutter, R. M. *Nature* 1996, 383, 178.
(13) Erhart, D.; Zimmermann, M.; Jacques, O.; Wittwer, M. B.; Ernst, B.; Constable, E.; Zvelebil, M.; Beaufils, F.; Wymann, M. P. *Chemistry & Biology* 2013, 20, 549.
(14) Ballister, E. R.; Aonbangkhen, C.; Mayo, A. M.; Lampson, M. A.; Chenoweth, D. M. *Nat. Commun.* 2014, 5.
(15) Hill, Z. B.; Martinko, A. J.; Nguyen, D. P.; Wells, J. A. *Nat. Chem. Biol.* 2018, 14, 112.
(16) Lerner, R. A. *Nat. Rev. Immunol.* 2016, 16, 498.
(17) Muyldermans, S. *Annu. Rev. Biochem.* 2013, 82, 775.
(18) Fanning, S. W.; Horn, J. R. *Protein Sci.* 2011, 20, 1196.
(19) Zavrtanik, U.; Luken, J.; Loris, R.; Lah, J.; Hadzi, S. *J. Mol. Biol.* 2018, 430, 4369.
(20) Al Qaraghuli, M. M.; Ferro, V. A. *J. Mol. Recognit.* 2017, 30.
(21) McMahon, C.; Baier, A. S.; Pascolutti, R.; Wegrecki, M.; Zheng, S. D.; Ong, J. X.; Erlandson, S. C.; Hilger, D.; Rasmussen, S. G. F.; Ring, A. M.; Manglik, A.; Kruse, A. C. *Nat. Struct. Mol. Biol.* 2018, 25, 289.
(22) Izzo, A. A.; Borrelli, F.; Capasso, R.; Di Marzo, V.; Mechoulam, R. *Trends Pharmacol. Sci.* 2009, 30, 515.
(23) Wu, C. Y.; Roybal, K. T.; Puchner, E. M.; Onuffer, J.; Lim, W. A. *Science* 2015, 350.
(24) Di Stasi, A.; Tey, S. K.; Dotti, G.; Fujita, Y.; Kennedy-Nasser, A.; Martinez, C.; Straathof, K.; Liu, E.; Durett, A. G.; Grilley, B.; Liu, H.; Cruz, C. R.; Savoldo, B.; Gee, A. P.; Schindler, J.; Krance, R. A.; Heslop, H. E.; Spencer, D. M.; Rooney, C. M.; Brenner, M. K. *N. Engl. J. Med.* 2011, 365, 1673.
(25) Virnekas, B.; Ge, L. M.; Pluckthun, A.; Schneider, K. C.; Wellnhofer, G.; Moroney, S. E. *Nucleic Acids Res.* 1994, 22, 5600.
(26) Moutel, S.; Bery, N.; Bernard, V.; Keller, L.; Lemesre, E.; de Marco, A.; Ligat, L.; Rain, J. C.; Favre, G.; Olichon, A.; Perez, F. *eLife* 2016, 5.
(27) Daley, T.; Smith, A. D. *Nat. Methods* 2013, 10, 325.
(28) Banaszynski, L. A.; Liu, C. W.; Wandless, T. J. *J. Am. Chem. Soc.* 2005, 127, 4715.

(29) Gormley, N. A.; Orphanides, G.; Meyer, A.; Cullis, P. M.; Maxwell, A. *Biochemistry* 1996, 35, 5083.
(30) Douglass, E. F.; Miller, C. J.; Sparer, G.; Shapiro, H.; Spiegel, D. A. *J. Am. Chem. Soc.* 2013, 135, 6092.
(31) Schwope, D. M.; Milman, G.; Huestis, M. A. *Clin. Chem.* 2010, 56, 1007.
(32) Luo, X.; Reiter, M. A.; d'Espaux, L.; Wong, J.; Denby, C. M.; Lechner, A.; Zhang, Y.; Grzybowski, A. T.; Harth, S.; Lin, W.; Lee, H.; Yu, C.; Shin, J.; Deng, K.; Benites, V. T.; Wang, G.; Baidoo, E. E. K.; Chen, Y.; Dev, I.; Petzold, C. J.; Keasling, J. D. *Nature* 2019, 567, 123.

Supplemental Methods

1. Chemical Synthesis

Biotinylated tetrahydrocannabinol (THC) (8) and cannabidiol (CBD) (13) were provided by the Institute for Protein Design at the University of Washington and were synthesized by DermaXon LLC as described below.

All solvents were reagent grade and used without further purification. All procedures were carried out at room temperature (r.t.) unless otherwise stated. All glassware was oven-dried at 60° C. prior to use. Magnesium sulfate was used as the drying agent. Yields refer to chromatographically pure compounds as determined by TLC or HPLC analysis. The identities and purities of all final products were checked by HPLC-ESI-MS, $^1$H, and $^{13}$C (including APT and DEPT) experiments. NMR spectra were obtained on a Bruker Ascend TM-400 instrument. All spectra were baseline-corrected. All $^{13}$C NMR spectra were obtained with complete proton decoupling. The signals in the $^{13}$C NMR spectra were assigned by means of DEPT (Distortionless Enhancement by Polarization Transfer): these methods enable differentiation between the resonances of quaternary carbons (C) and the carbons of CH, CH$_2$ and CH$_3$ groups. NMR results of all target compounds were consistent with the assigned structures. High Resolution mass spectrometry (HRMS) analyses were performed on a Waters/Micromass LCT-TOF instrument.

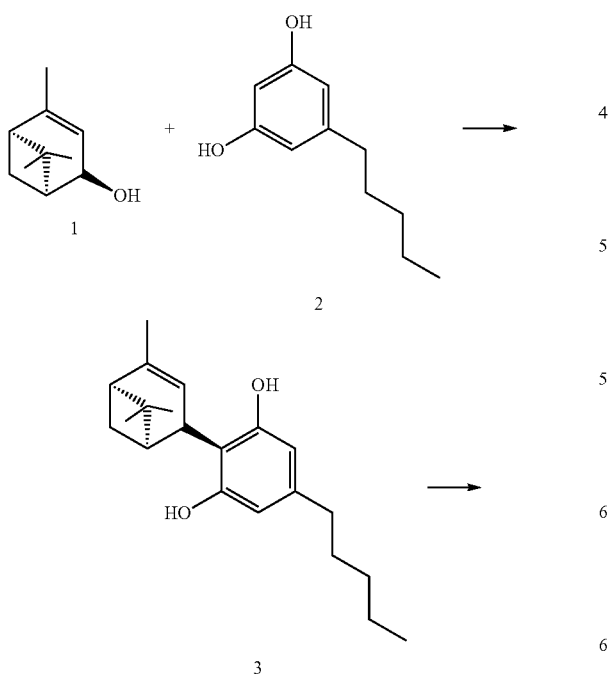

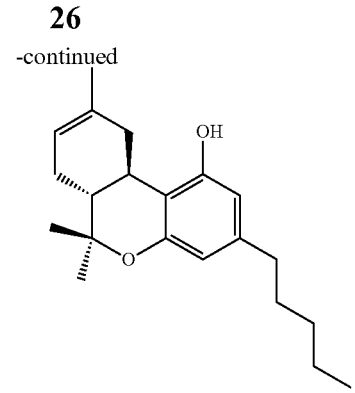

Protocols adapted for synthesis of compound 4 $\Delta^8$-THC from a previous report.[1]

5-pentyl-2-[(1R,5S)-4,6,6-trimethylbicyclo[3.1.1]hept-3-en-2-yl]benzene-1,3-diol (3). To a solution of olivetol 2 (1.98 g, 11 mmol) and p-toluenesulfonic acid (191 mg, 1.1 mmol) in CHCl$_3$ (65 mL) at r.t. under N$_2$ was added (s)-cis-verbenol 1 (1.7 g, 11 mmol) in CHCl$_3$ (30 mL). After being stirred at r.t. for 2.5 h, the reaction mixture was poured into saturated NaHCO$_3$ and extracted two times with CH$_2$Cl$_2$. The combined organic extracts were dried over MgSO$_4$ and evaporated. The residue was purified by chromatography on silica gel, eluting with EtOAc/hexane (1:9) to afford 3 as a yellow oil (1.34 g, 4.26 mmol, 39%). $^1$H NMR (400 MHz, CDCl$_3$): δ 6.20 (s, 1H), 5.70 (s, 1H), 3.92 (s, 1H), 2.48-2.39 (m, 1H), 2.29 (ddd, J=16.9, 11.5, 5.8 Hz, 1H), 2.18 (t, J=5.5 Hz, 1H), 1.85 (s, 2H), 1.61-1.52 (m, 3H), 1.43 (s, 5H), 1.32 (s, 5H), 0.96 (s, 2H), 0.89 (t, J=6.9 Hz, 3H). $^{13}$C NMR (100 MHz, CDCl$_3$):

$\Delta^8$-THC (4). To a solution of compound 3 (0.6 g, 1.9 mmol) in CH$_2$Cl$_2$ (35 mL) at 0° C. under N$_2$ was added BF$_3$/Et$_2$O (481 uL, 3.8 mmol), and the mixture was allowed to warm to r.t. After being stirred for 3 h, the mixture was poured into saturated NaHCO$_3$ and extracted two times with CH$_2$Cl$_2$. The combined organic extracts were dried over MgSO$_4$ and evaporated. The residue was purified by chromatography on silica gel, eluting with CH$_2$Cl$_2$/cyclohexane (5:5), to yield 4 as a yellow oil (280 mg, 0.89 mmol, 47%). $^1$H NMR (400 MHz, CDCl$_3$): δ 6.28 (s, 1H), 6.08 (d, J=1.4 Hz, 1H), 5.41 (d, J=4.1 Hz, 1H), 5.18 (d, J=4.9 Hz, 1H), 3.21 (dd, J=16.4, 4.0 Hz, 1H), 2.78-2.61 (m, 1H), 2.40 (dd, J=8.3, 5.8 Hz, 2H), 2.13 (dd, J=10.9, 4.9 Hz, 1H), 1.93-1.73 (m, 3H), 1.68 (s, 3H), 1.61-1.45 (m, 2H), 1.39-1.34 (m, 3H), 1.33-1.19 (m, 4H), 1.09 (s, 3H), 0.87 (t, J=6.9 Hz, 3H).

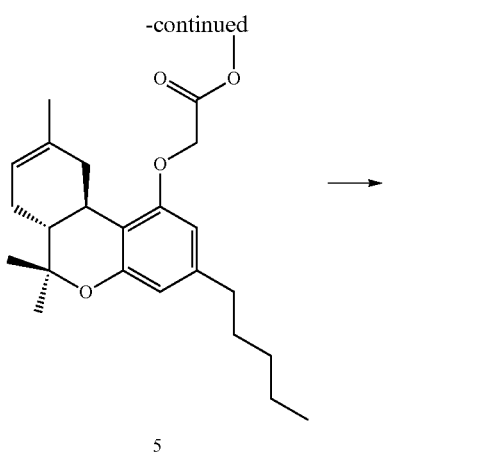

5

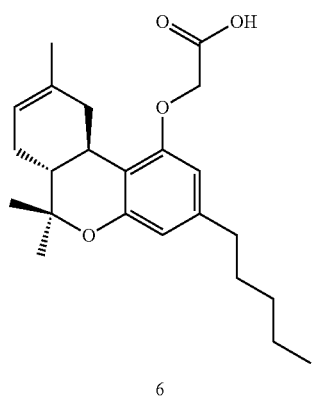

6

Methyl 2-{[(6aR,10aR)-6,6,9-trimethyl-3-pentyl-6H,6aH,7H,10H,10aH-benzo[c]isochromen-1-yl]oxy}acetate (5). To a solution of compound 4 (280 mg, 0.89 mmol) and potassium carbonate (123 mg, 8.9 mmol) in MEK (10 mL) at r.t. under $N_2$ was added methyl bromoacetate (163 mg, 1.07 mmol). After being stirred at 80° C. for 18 h, an additional 30 μL of methyl bromoacetate were added since the conversion of the starting material was only approximately 60%. The reaction was stirred at 80° C. for 8 h. 87 mg of cesium carbonate were added and the reaction was stirred at 80° C. overnight. The reaction mixture was poured into saturated $NH_4Cl$ and extracted two times with AcOEt. The combined organic extracts were washed with water, dried over $MgSO_4$ and evaporated to afford 5 as a yellow oil (344 mg, 0.89 mmol, quantitative yield). $^1$H NMR (400 MHz, $CDCl_3$): δ 6.35 (d, J=1.1 Hz, 1H), 6.11 (d, J=1.1 Hz, 1H), 5.42 (d, J=4.3 Hz, 1H), 4.62 (s, 2H), 3.92-3.75 (m, 3H), 3.34 (dd, J=16.4, 4.5 Hz, 1H), 2.74 (td, J=11.0, 5.0 Hz, 1H), 2.48 (td, J=7.3, 2.1 Hz, 2H), 2.23-2.07 (m, 1H), 1.92-1.75 (m, 3H), 1.71 (s, 3H), 1.64-1.49 (m, 2H), 1.37 (s, 3H), 1.34-1.23 (m, 2H), 1.10 (s, 3H), 0.88 (t, J=6.9 Hz, 4H). $^{13}$C NMR (100 MHz, $CDCl_3$): δ 169.46, 157.07, 154.66, 142.53, 135.09, 119.07, 112.53, 111.32, 103.78, 65.51, 52.13, 44.95, 36.08, 35.88, 31.75, 31.56, 30.70, 27.94, 27.57, 26.92, 23.59, 22.55, 18.47, 14.03.

2-{[(6aR,10aR)-6,6,9-trimethyl-3-pentyl-6H,6aH,7H,10H,10aH-benzo[c]isochromen-1-yl]oxy}acetic acid (6). A solution of compound 5 (269 mg, 0.73 mmol) and lithium hydroxide monohydrate (135 mg, 3.2 mmol) in a mixture of THF (15 mL) and water (250 μL) under $N_2$ was stirred at 50° C. for 18 h. 250 μL of water were added since the conversion of the starting material was not achieved. The reaction was stirred at 65° C. for 8 h and at r.t. overnight. The reaction mixture was poured into 1 N HCl, and extracted two times with AcOEt. The combined organic extracts were washed with water, dried over $MgSO_4$ and evaporated. The residue was purified by chromatography on silica gel, eluting with a gradient of $CH_2Cl_2$/MeOH (2% to 20% of MeOH), to yield 6 as a yellow oil (185 mg, 0.5 mmol, 68%). $^1$H NMR (400 MHz, $CDCl_3$): δ 6.37 (d, J=1.1 Hz, 1H), 6.14 (d, J=1.1 Hz, 1H), 5.42 (d, J=3.6 Hz, 1H), 4.67 (s, 2H), 3.28 (d, J=16.6 Hz, 1H), 2.74 (td, J=11.0, 4.9 Hz, 1H), 2.57-2.42 (m, 2H), 2.22-2.08 (m, 1H), 1.89-1.76 (m, 3H), 1.69 (s, 3H), 1.63-1.52 (m, 2H), 1.38 (s, 3H), 1.35-1.27 (m, 4H), 1.09 (s, 3H), 0.88 (t, J=6.9 Hz, 3H). $^{13}$C NMR (101 MHz, $CDCl_3$) δ 156.78, 154.76, 142.67, 135.02, 119.15, 112.58, 111.64, 103.88, 77.35, 77.24, 77.04, 76.72, 65.04, 44.95, 36.15, 35.89, 31.76, 31.58, 30.72, 27.95, 27.57, 23.55, 22.56, 18.48, 14.04.

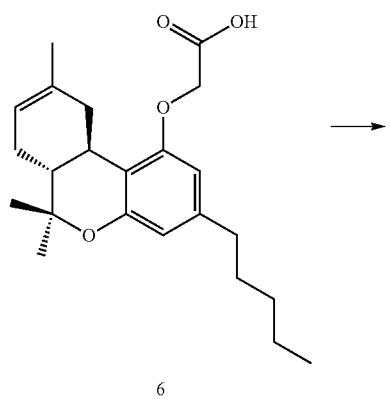

6

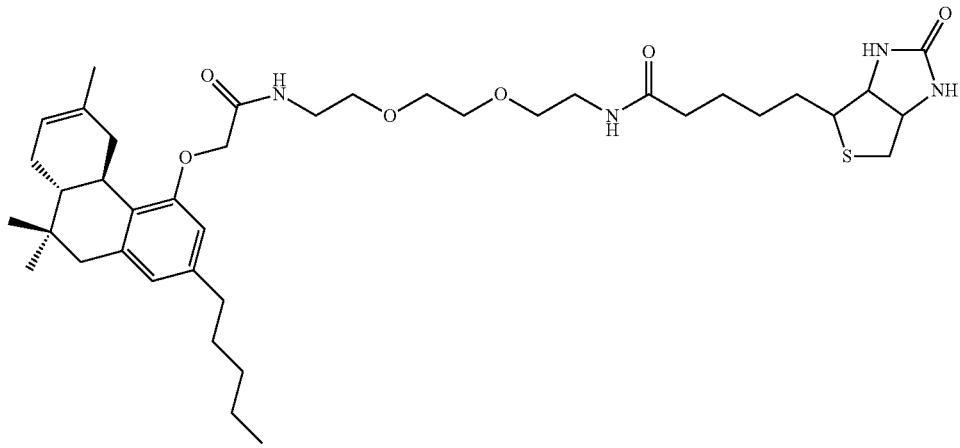

7

N-(2-{2-[2-(2-{[(6aR,10aR)-6,6,9-trimethyl-3-pentyl-6H,6aH,7H,10H,10aH-benzo[c]isochromen-1-yl]oxy}acetamido)ethoxy]ethoxy}ethyl)-5-{2-oxo-hexahydro-1H-thieno[3,4-d]imidazolidin-4-yl}pentanamide (7). A mixture of O-(7-Azabenzotriazol-1-yl)-N,N,N',N'-tetramethyluronium hexafluorophosphate HATU (53 mg, 0.14 mmol), DIPEA (28 mg, 0.215 mmol, 0.31 mL) and compound 6 (40 mg, 0.107 mmol) in DCM (2 mL) and DMF (2 mL) was stirred under $N_2$ at r.t. for 1 h. Biotin-(PEO)$_4$ amine (50 mg, 0.118 mmol) diluted in a mixture of DCM (2 mL) and DMF (2 mL) was added to the reaction mixture. The reaction mixture was stirred at r.t. for 46 h. The reaction medium was concentrated. Column chromatography (silica gel, gradient MeOH/DCM 2 to 30%) afforded the title compound as a white solid (12 mg, 16%). $^1$H NMR (400 MHz, CDCl$_3$) δ 6.86 (br s, 1H), 6.41 (t, J=5.4 Hz, 1H), 6.37 (s, 1H), 6.25 (br s 1H), 6.19 (s, 1H), 5.44 (d, J=4.1 Hz, 1H), 5.34 (s, 1H), 4.58-4.44 (m, 3H), 4.34-4.27 (m, 1H), 3.64-3.49 (m, 10H), 3.45-3.37 (m, 2H), 3.18-3.10 (m, 1H), 3.07-2.98 (m, 1H), 2.90 (dd, J=12.8, 4.90 Hz, 1H), 2.77-2.66 (m, 2H), 2.47 (dd, J=8.7, 6.4 Hz, 2H), 2.26-2.12 (m, 3H), 1.92-1.60 (m, 10H), 1.62-1.51 (m, 2H), 1.44 (dd, J=15.4, 7.8 Hz, 2H), 1.38 (s, 3H), 1.36-1.24 (m, 4H), 1.10 (s, 3H), 0.88 (t, J=6.84 Hz, 3H). $^{13}$C NMR (100 MHz, CDCl$_3$): δ 14.03, 18.44, 22.54, 23.64, 25.53, 27.53, 27.94, 28.09, 28.15, 30.74, 31.55, 31.83, 35.85, 35.92, 36.70, 38.84, 39.12, 40.51, 45.09, 53.43, 55.46, 60.17, 61.81, 67.89, 69.68, 69.97, 70.17, 70.20, 104.59, 111.75, 112.17, 119.70, 134.36, 143.03, 154.68, 156.63, 163.70, 168.92, 173.19, 192.65. HRMS (positive mode) for C39H61N4O7S$^+$[M+1]$^+$ calc 729.4261, found 729.4268.

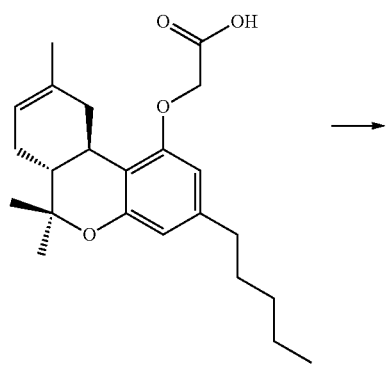

6

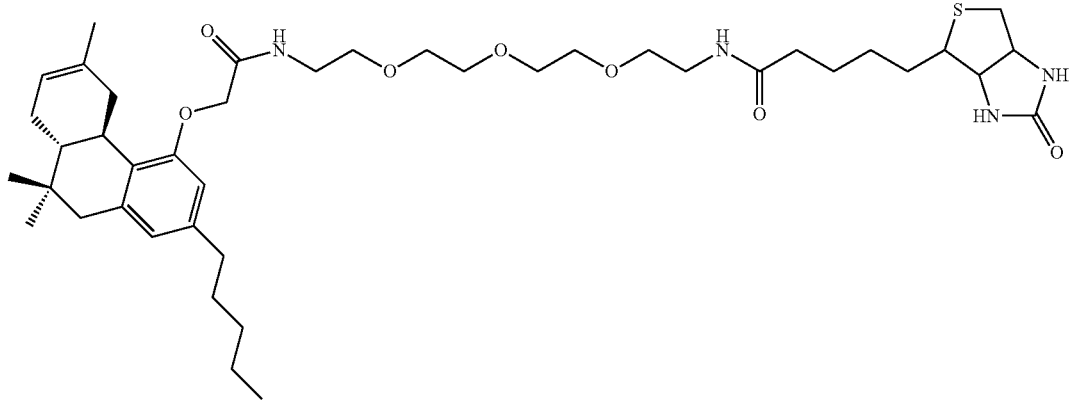

8

N-[2-(2-{2-[2-(2-{[(6aR,10aR)-6,6,9-trimethyl-3-pentyl-6H,6aH,7H,10H,10aH-benzo[c]isochromen-1-yl]oxy}acetamido)ethoxy]ethoxy}ethoxy)ethyl]-5-{2-oxo-hexahydro-1H-thieno[3,4-d]imidazolidin-4-yl}pentanamide (8). A mixture of O-(7-Azabenzotriazol-1-yl)-N,N,N',N'-tetramethyluronium hexafluorophosphate HATU (53 mg, 0.14 mmol), DIPEA (28 mg, 0.215 mmol, 0.31 mL) and compound 6 (40 mg, 0.107 mmol) in DCM (4 mL) and DMF (2 mL) was stirred under $N_2$ at r.t. for 1 h. Biotin-(PEO)$_4$ amine (50 mg, 0.118 mmol) was added. The reaction mixture was stirred at r.t. for 46 h. The reaction medium was concentrated. Column chromatography (silica gel, gradient MeOH/DCM 2 to 30%) afforded the title compound as a white solid (12 mg, 16%). $^1$H NMR (400 MHz, CDCl$_3$) δ 6.89 (br s, 1H), 6.51 (t, J=5.4 Hz, 1H), 6.37 (d, J=1.3 Hz, 1H), 6.19 (d, J=1.3 Hz, 1H), 6.09 (s, 1H), 5.44 (d, J=4.4 Hz, 1H), 5.16 (s, 1H), 4.65-4.41 (m, 3H), 4.42-4.24 (m, 1H), 3.69-3.49 (m, 13H), 3.42 (dd, J=9.9, 5.1 Hz, 2H), 3.15 (dt, J=11.9, 6.0 Hz, 1H), 3.09-2.95 (m, 1H), 2.90 (dd, J=12.8, 5.0 Hz, 1H), 2.71 (dd, J=17.8, 8.5 Hz, 2H), 2.47 (dd, J=8.7, 6.4 Hz, 2H), 2.34-2.06 (m, 3H), 1.96-1.60 (m, 11H), 1.60-1.49 (m, 2H), 1.45 (dd, J=15.4, 7.8 Hz, 2H), 1.38 (s, 2H), 1.34-1.25 (m, 4H), 1.10 (s, 3H), 0.89 (t, J=6.8 Hz, 3H). $^{13}$C NMR (101 MHz, CDCl3) δ 173.10, 168.84, 163.48, 156.66, 154.66, 143.01, 134.44, 119.64, 112.18, 111.71, 104.60, 70.48, 70.44, 70.32, 70.09, 69.95, 69.71, 67.90, 61.76, 60.13, 55.37, 45.09, 40.52, 39.15, 38.85, 36.69, 35.85, 31.82, 31.55, 30.75, 28.09, 27.95, 27.54, 25.49, 23.64, 22.54, 18.45, 14.04. HRMS (positive mode) for C41H65N4O8S$^+$[M+1]$^+$ calc 773.4523 found 773.4554.

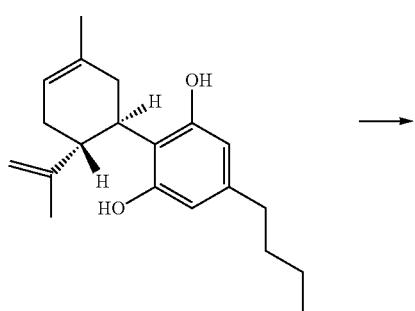

9

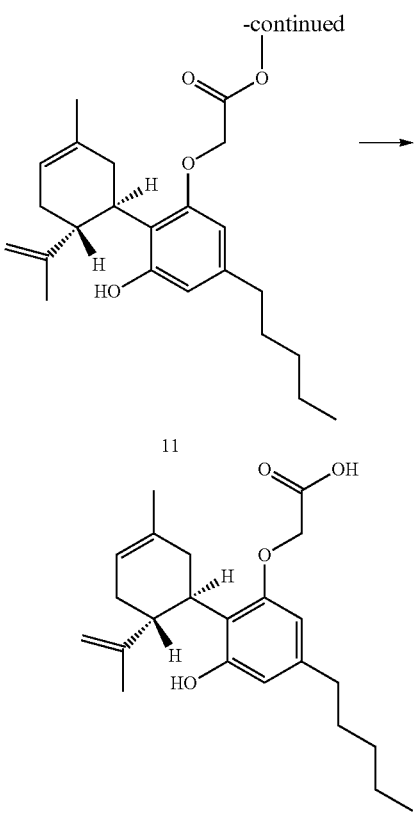

10

11

11

Methyl 2-{3-hydroxy-2-[(1R,6R)-3-methyl-6-(prop-1-en-2-yl)cyclohex-3-en-1-yl]-5-pentylphenoxy}acetate (10). A solution of CBD, compound 9 (50 mg, 0.16 mmol) and cesium carbonate (52 mg, 0.16 mmol) in MEK (2 mL) under $N_2$ was heated at 80° C. After being stirred at 80° C. for 1 h, methyl bromoacetate (15 μL, 0.16 mmol) was added. The reaction was stirred at 80° C. for 8 h. The reaction mixture was concentrated. Two batches of the reaction were combined and were purified by chromatography on silica gel, eluting with a gradient of cyclohexane/ethyl acetate (95/5) to (65/35). A mixture of CBD and the expected product (50/50, according to HPLC quantification) was obtained (140 mg overall).

2-{3-hydroxy-2-[(1R,6R)-3-methyl-6-(prop-1-en-2-yl)cyclohex-3-en-1-yl]-5-pentylphenoxy}acetic acid (11). A solution of mixture 10 previously obtained (140 mg) and lithium hydroxide monohydrate (65 mg, 1.5 mmol) in a mixture of THF (5 mL) and water (125 µL) under N$_2$ was stirred at room temperature overnight. The residue was purified by chromatography on silica gel, eluting with a gradient of CH$_2$Cl$_2$/MeOH (100/0 to 90/10), to yield 11 as a yellow oil (45 mg, 25% over the two steps). $^1$H NMR (400 MHz, CDCl$_3$): δ ppm 6.38 (s, 1H), 6.13 (br. s., 2H), 5.57 (br. s., 1H), 4.62-4.48 (m, 3H), 4.36 (br. s., 1H), 4.08-3.98 (m, 1H), 2.53-2.33 (m, 3H), 2.30-2.16 (m, 1H), 2.14-2.06 (m, 1H), 1.85-1.72 (m, 5H), 1.64 (s, 3H), 1.56 (dt, J=15.00, 7.56 Hz, 2H), 1.37-1.22 (m, 4H), 0.88 (t, J=6.96 Hz, 3H).

was stirred under N$_2$ at r.t. for 1 h. Biotin-(PEO)$_3$ amine (13 mg, 0.035 mmol) diluted in DMF (1 mL) was added to the reaction mixture. The reaction mixture was stirred at r.t. for 46 h and concentrated. Column chromatography (silica gel, gradient MeOH/DCM 0 to 15%) afforded the title compound as a white solid (9 mg, 35%). $^1$H NMR (400 MHz, CDCl 3) δ 6.83 (br s, 11H), 6.45-6.34 (m, 1H), 6.25 (m, 11H), 6.13 (br s, 11H), 6.05 (br s, 11H), 5.57 (br s, 1H), 5.31 (br s, 1H), 4.64 (br s, 1H), 4.50-4.56 (m, 1H), 4.50-4.37 (m, 3H), 4.36-4.29 (m, 1H), 3.98-3.89 (m, 1H), 3.64-3.46 (m, 10H), 3.46-3.37 (m, 2H), 3.19-3.12 (m, 1H), 2.92 (dd, J=12.92, 4.89 Hz, 1H), 2.73 (d, J=12.80 Hz, 2H), 2.56-2.35 (m, 3H), 2.22 (t, J=7.22 Hz, 3H), 2.13-2.03 (m, 1H), 1.87-1.60 (m,

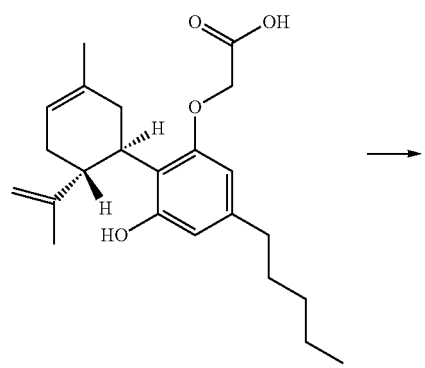

11

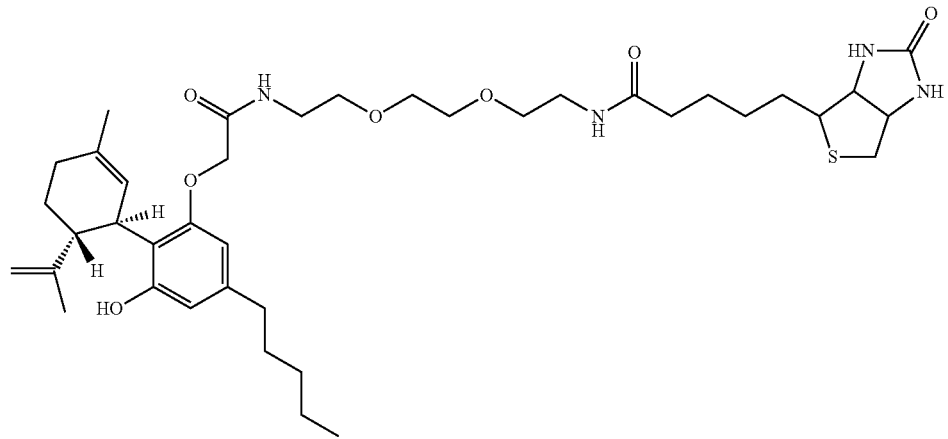

12

N-(2-{2-[2-(2-{3-hydroxy-2-[(1R,6R)-3-methyl-6-(prop-1-en-2-yl)cyclohex-2-en-1-yl]-5-pentylphenoxy}acetamido)ethoxy]ethoxy}ethyl)-5-{2-oxo-hexahydro-1H-thieno[3,4-d]imidazolidin-4-yl}pentanamide (12). A mixture of O-(7-Azabenzotriazol-1-yl)-N,N,N',N'-tetramethyluronium hexafluorophosphate HATU (32 mg, 0.084 mmol), DIPEA (20 µL, 0.128 mmol) and compound 11 (24 mg, 0.064 mmol) in DCM (1 mL) and DMF (1 mL) 11H), 1.54 (dt, J=14.87, 7.50 Hz, 3H), 1.49-1.41 (m, 2H), 1.35-1.21 (m, 4H), 0.87 (t, J=6.90 Hz, 3H). $^{13}$C NMR (101 MHz, CDCl$_3$) δ ppm 14.06, 20.00, 22.54, 25.47, 28.02, 29.87, 30.84, 31.48, 35.89, 38.84, 39.18, 40.40, 40.51, 53.58, 55.35, 60.28, 61.92, 69.89, 70.17, 104.13, 110.85, 111.13, 120.30, 123.55, 129.39, 163.51, 169.35, 173.40. HRMS (positive mode) for C39H61N407S$^+$[M+1]$^+$ calc 729.4261, found 729.4260.

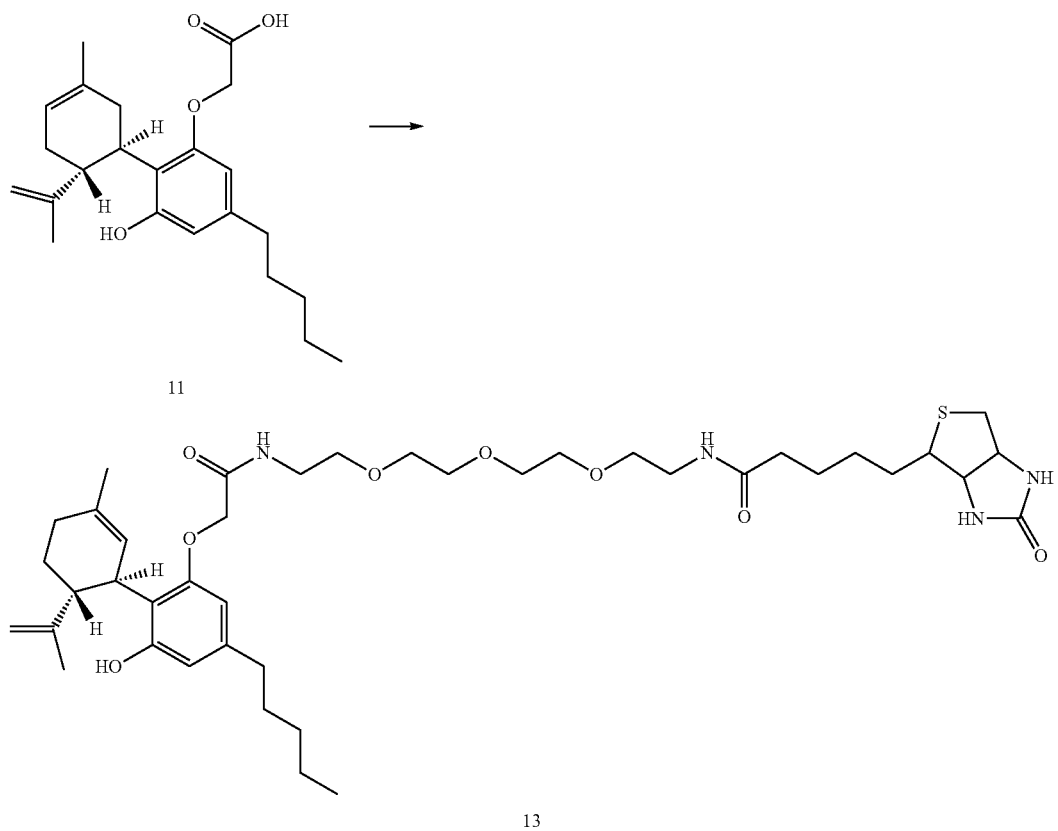

N-[2-(2-{2-[2-(2-{3-hydroxy-2-[(1R,6R)-3-methyl-6-(prop-1-en-2-yl)cyclohex-2-en-1-yl]-5-pentylphenoxy}acetamido)ethoxy]ethoxy}ethoxy)ethyl]-5-{2-oxo-hexahydro-1H-thieno[3,4-d]imidazolidin-4-yl}pentanamide (13). A mixture of O-(7-Azabenzotriazol-1-yl)-N,N,N',N'-tetramethyluronium hexafluorophosphate HATU (30 mg, 0.077 mmol), DIPEA (20 μL, 0.118 mmol) and compound 11 (22 mg, 0.059 mmol) in DCM (1 mL) and DMF (1 mL) was stirred under $N_2$ at r.t. for 1 h. Biotin-(PEO)$_4$ amine (27 mg, 0.065 mmol) diluted in DCM (1 mL) was added. The reaction mixture was stirred at r.t. for 46 h. The reaction medium was concentrated. Column chromatography (silica gel, gradient MeOH/DCM 2 to 15%) afforded the title compound as a white solid (20 mg, 45%). $^1$H NMR (400 MHz, CDCl$_3$) δ 6.83 (br s, 1H), 6.66-6.47 (m, 1H), 6.37 (m, 1H), 6.31-6.17 (m, 1H), 6.12 (br s, 1H), 5.58 (br s, 1H), 5.35 (br s, 1H), 4.63 (br s, 1H), 4.56-4.46 (m, 2H), 4.46-4.38 (m, 2H), 4.38-4.26 (m, 1H), 3.98-3.89 (m, 1H), 3.66-3.46 (m, 14H), 3.46-3.37 (m, 2H), 3.19-3.11 (m, 1H), 2.91 (dd, J=12.92, 4.89 Hz, 1H), 2.74 (d, J=12.80 Hz, 2H), 2.56-2.34 (m, 3H), 2.15-2.31 (m, 3H), 2.13-2.01 (m, 111), 1.86-1.60 (m, 1111), 1.54 (dt, J=14.96, 7.51 Hz, 3H), 1.48-1.39 (m, 2H), 1.35-1.21 (m, 4H), 0.88 (t, J=6.96 Hz, 3H). $^{13}$C NMR (101 MHz, CDCl$_3$) δ ppm 14.05, 19.92, 22.52, 23.73, 25.47, 27.56, 28.04, 28.06, 29.95, 30.83, 31.47, 35.83, 35.87, 36.40, 38.83, 39.18, 46.03, 53.43, 55.37, 60.23, 61.83, 69.90, 69.98, 70.06, 70.31, 70.36, 70.39, 104.15, 10.92, 110.94, 110.97, 111.04, 111.08, 120.22, 123.76, 123.77, 123.84, 129.16, 163.77 169.17, 173.32. HRMS (positive mode) for $C_{41}H_{65}N_4O_8S^+[M+1]^+$ calc 773.4523, found 773.4562.

2. Nanobody Library Construction and Validation

Library construction: The DNA library was designed with a universal nanobody scaffold and randomized CDR sequences similarly to a reported method.[2] The combinatorial DNA library was chemically synthesized by a trinucleotide mutagenesis technology (Thermo Fisher Scientific). To subclone the library into a phagemid vector, ~300 ng of the synthetic DNA library was used as template to set up 30×50 μL PCR reactions, each with 1 μL of Platinum SuperFi DNA polymerase (Thermo Fisher Scientific) and 0.5 μM (each) primers. The PCR protocol included an initial denaturation step at 98° C. for 30 s followed by 20 cycles of 98° C. for 10 s, 70° C. for 10 s, and 72° C. for 10 s, and a final step extension at 72° C. for 5 min. ~40 μg purified PCR products and ~60 μg of a pADL-23c phagemid vector (Antibody Design Labs) were digested for 1 h at 37° C. with BglI (Thermo Fisher Scientific) and purified before the ligation. ~8.5 μg digested vector and ~3.9 μg inserts were ligated with 260 units of T4 DNA ligase (Thermo Fisher Scientific) in a 2,600 μL reaction at 4° C. for overnight. Ligated products were purified by a Purelink™ PCR quick purification kit (Invitrogen) to obtain a final volume of 50 μL (~278.9 ng/μL) and then transformed to E. coli electrocompetent TG1 cells (Lucigen) in 30 electroporation cuvettes, each containing 1.4 μL ligated products and 50 μL cells, by following the manufacturer's instruction (1,800 V, 10 μF, 600 Ω). Electroporated cells were resuspended with a warm recovery medium (Lucigen) and incubated by shaking (250 rpm) at 37° C. for 1 h and then mixed with ~470 mL 2×YT, 2% glucose. Cells were plated on 500 2×YT-ampicillin-glucose agar plates (140 mm), grown overnight at 30° C., and scraped with 2×TY. The library was aliquoted and stored in 25% glycerol at −80° C.

Next generation sequencing library validation: To sequence the phage-displayed nanobody library, phagemid DNAs were isolated from purified phage particles using a QIAprep Spin M13 kit (Qiagen). DNA concentration was measured by a Nanodrop™ 2000 spectrophotometer (Thermo Fisher Scientific). A two-step low-cycle-number PCR was performed to introduce the Illumina adaptors and 8-bp unique molecular identifiers (UMIs) to the 3' and 5' ends of amplicons with specific primers. The library was sequenced by an Illumina NextSeq™ platform using a 2×150 bp high-output kit. The sequencing data were first processed to trim UMI sequences using Flexbar™.[3] Low-quality reads were filtered with a minimum quality score of 20. To accommodate errors within UMIs while retrieving CDR sequences, undetermined bases in UMIs or shorter barcodes were allowed. Clean reads were then aligned to CDR-adjacent scaffold sequences to extract designed CDR sequences at a 0.1 mismatch rate. Three CDR sequences were obtained by merging paired-end reads. To retain correct sequences, CDR sequences were required to be in the same reading frame without any undetermined base or stop codon.

A custom Perl script, shown below, was used to analyze translated protein sequences. CDR protein sequence logos were generated with WebLogo3.6.[4]

```
#! /usr /bin /perl -w
use strict ;
my $fastqL = $ARGV [0] ;
my $fastqR = $ARGV [1] ;
my %processedReads ;
my %phagereads ;
open (FQL, "$fastqL") | | die;
while (my $ln = <FQL> ) {
  if ($. % 4 !=1) (next ;)
  chomp $ln;
  my @code = split(/\_/, $ln) ;
  my $coord = $code [0] ;
  my $tagcodeL = $code [1] ;
  my $cdr1_rna = $code [2] ;
  my $cdr2_rna = $code [3] ;
  #remove the peptides containing undertermined nul
  if ($cdr1_rna=~ /N/ or $cdr2_rna =~ /N/ ) {
    next;
  }
  # filter for fixed peptide length
  if (length ($cdr1_rna) % 3==0 and length ($cdr2_rna) %3==0) {
    $phagereads{$coord} =$tagcodeL.' | '.$cdr1_rna. ' | '.$cdr2_rna ;
  }
}
close (FQL) ;
open (FQR, "$fastqR") | | die;
my $headertag;
while (my $ln=<FQR> ) {
  chomp $ln;
  if {$.%4==1){
    $headertag = $ln;
    next ;
  }
  if {$. %4==2){
    my @code = split(/\_/, $headertag) ;
    my $coord = $code [0] ;
    $coord=~s/ 2\:N\ :0 \ : / 1 \ : N\ :0\ : / ;
    my $tagcodeR = $code [1] ;
    my $cdr3_rna = $ ln;
    # remove the peptides containing undertermined nul
    if ($cdr3_rna=~ /N/ ) {
      next;
    }
    # filter forframe shift
    if (length ($cdr3_rna) % 3==0 and exists $phagereads {$ coord}) {
      $processedReads {$coord} =$phagereads {$coord}. ' | '.$cdr3_rna.' | '.$tagcodeR;
    }
  }
}
close (FQR) ;
open ( PRO, ">$ARGV [2] ") | | die;
my %countPeptide;
foreach my $key (keys %processedReads) {
  my @data = split{/ \ | / , $processedReads{$key}) ;
  my$c1 = translate ($data [1] ) ;
  my$c2 = translate ($data [2] ) ;
  my$c3 = translate ($data [3]) ;
  print PRO
$key,"\t", $data [0] , "\t", $data [4] , "\t", $data [1] ,"\t", $data [2] ,"\t", $data [3] , "\t", $c1, "\t", $c2, "\t", $c3, "\n";
  $countPeptide {$data [0] , '_' . $data [4] ) {$c1. '_' . $c2.'_' . $c3} ++;
}
close(PRO);
```

```
foreach my $key (keys %countPeptide) {
   foreach my $sky (keys % {$countPeptide { $key } } ) {
      print '>' , $key, '-' , $countPeptide { $key }{ $sky }, "\n";
      print $sky, "\n" ;
   }
}
sub reverse_complement {
   my $dna = shift;
   # reverse the DNA sequence
   my $revcomp = reverse ($dna) ;
   # complement the reversed DNA sequence
   $revcomp =~ tr/ATCGN/TAGCN/ ;
   return $revcomp ;
}
sub translate {
   my (%genetic_code) = {
      'TCA' => 'S', # Serine
      'TCC' => 'S', # Serine
      'TCG' => 'S', # Serine
      'TCT' => 'S', # Serine
      'TTC' => 'F', # Phenylalanine
      'TTT' => 'F', #P henylalanine
      'TTA' => 'L', # Leucine
      'TTG' => 'L', # Leucine
      'TAC' => 'Y', # Tyrosine
      'TAT' => 'Y', # Tyrosine
      'TAA' => '4', # Stop
      'TAG' => '4', # Stop
      'TGC' => 'C', # Cysteine
      'TGT' => 'C', # Cysteine
      'TGA' => '4', # Stop
      'TGG' => 'W', # Tryptophan
      'CTA' => 'L', # Leucine
      'CTC' => 'L', # Leucine
      'CTG' => 'L', # Leucine
      'CTT' => 'L', # Leucine
      'CCA' => 'P', # Proline
      'CAT' => 'H', # Histidine
      'CAA' => 'Q', # Glutamine
      'CAG' => 'Q', # Glutamine
      'CGA' => 'R', # Arginine
      'CGC' => 'R', # Arginine
      'CGG' => 'R', # Arginine
      'CGT' => 'R', # Arginine
      'ATA' => 'I', # Isoleucine
      'ATC' => 'I', # Isoleucine
      'ATT' => 'I', # Isoleucine
      'ATG' => 'M', # Methionine
      'ACA' => 'T', # Threonine
      'ACC' => 'T', # Threonine
      'ACG' => 'T', # Threonine
      'ACT' => 'T', # Threonine
      'AAC' => 'N', # Asparagine
      'AAT' => 'N', # Asparagine
      'AAA' => 'K', # Lysine
      'AAG' => 'K', # Lysine
      'AGC' => 'S', # Serine
      'AGT' => 'S', # Serine
      'AGA' => 'R', # Arginine
      'AGG' => 'R', # Arginine
      'CCC' => 'P', # Proline
      'CCG' => 'P', # Proline
      'CCT' => 'P', # Proline
      'CAC' => 'H', # Histidine
      'GTA' => 'V', # Valine
      'GTC' => 'V', # Valine
      'GTG' => 'V', # Valine
      'GTT' => 'V', # Valine
      'GCA' => 'A', # Alanine
      'GCC' => 'A', # Alanine
      'GCG' => 'A', # Alanine
      'GCT' => 'A', # Alanine
      'GAC' => 'D', # Aspartic Acid
      'GAT' => 'D', # Aspartic Acid
      'GAA' => 'E', # Glutamic Acid
      'GAG' => 'E', # Glutamic Acid
      'GGA' => 'G', # Glycine
      'GGC' => 'G', # Glycine
      'GGG' => 'G', # Glycine
```

```
        'GGT' => 'G' # Glycine
    };
    my $rna = shift;
    # if (length ($rna) %3! =0) {
    # return (0);
    # }
    my $protein = " " ;
    for (my $i =0; $i <lenght ($rna)-2; $ i+=3) {
        my $codon =substr ($rna, $i, 3):
        if (not exists $genetic_code {$codon }) {
            $protein . = 6;
        } else {
            $protein .= $genetic_code {$codon};
        }
    }
    return ($protein);
}
```

3. Phage Display Selection

To prepare a phage library, the phagemid-containing TG1 bacterial stock from the "Library construction" was diluted with 2×YT media with 2% glucose and 100 μg/mL ampicillin to OD600 of ~0.1 and cultured at 37° C. to OD600 of ~0.4 to 0.5. Cells were superinfected by adding a helper phage CM13 at 5×10$^9$ pfu/mL for 1 h, pelleted to remove the glucose, resuspended with fresh 2×YT media containing 100 μg/mL ampicillin and 50 μg/mL kanamycin, and incubated at 25° C. for overnight. To purify phage particles, cells were removed by centrifugation at 5,000×g, 4° C. for 30 min and phage particles in the supernatant were precipitated with polyethylene glycol (PEG). The supernatant was added with ⅕ volume PEG/NaCl solution (20% (w/v) polyethylene glycol 6,000 and 2.5 M NaCl), placed on ice for 1 h, and centrifuged at 12,000×g, 4° C. for 30 min. Phage pellets were resuspended in 1×PBS and stored at 4° C. for short-term use or with 25% glycerol at −80° C. for long-term storage.

Anchor binder selection was performed using biotin- and biotinylated-CBD-bound streptavidin magnetic beads for negative and positive selections, respectively, in each selection round. Briefly, 300 μL 10 μM biotin or biotinylated CBD were captured by 300 μL streptavidin-coated magnetic beads (Dynabeads™ M-280 Streptavidin, Thermo Fisher Scientific) and blocked with 1% casein and 1% BSA in 1×PBS pH 7.4 at r.t. for 1 h. In each round, the phage-displayed nanobody library was incubated with the biotin-bound beads for 1 h at r.t. to remove off-target binders and the supernatant was incubated with biotinylated CBD-bound beads for 1 h. Beads were washed with 10×0.05% PBST (1×PBS with 0.05% v/v Tween 20) and phage particles were competitively eluted with 50, 10 and 1 μM CBD in the first, second, and third selection rounds, respectively, and 100 nM CBD in the fourth to sixth rounds. After six rounds of biopanning, single colonies were picked and validated by phage ELISA followed by DNA sequencing.

Dimerization binders were selected using CBD-free and bound CA-14 for the negative and positive selections, respectively. Briefly, to prepare the bait for each selection round, 600 μL 1 μM biotinylated CA-14 were captured by 600 μL streptavidin beads and blocked with 1% casein and 1% BSA in 1×PBS pH 7.4 for 1 h at r.t. The beads were divided by a 2:1 ratio for the negative and positive selections, respectively. For the positive selection, the CA-14 bound beads were incubated with 50, 10, 1, and 1 μM CBD to generate the CBD-CA-14 complex as the bait from the rounds 1 to 4, respectively. Biopanning was performed as described above except that bound phages were eluted with 100 mM triethylamine. Four rounds of biopanning were performed before single colony picking and validation.

4. Phage ELISA

To prepare single-phage ELISA, individual colonies were randomly picked, inoculated into 250 μL media (2×TY, 2% glucose, 100 μg/mL ampicillin) per well in sterile deep-well plates (Thermo Fisher Scientific), and grown at 37° C. for overnight. 10 μL cultures were inoculated into 500 μL fresh media and cells were grown to OD600 of ~0.5 and infected by CM13 helper phage with the multiplicity of infection (MOI) of ~18. The cultures were incubated at 37° C. for 1 h, added with kanamycin of 50 μg/mL final concentration, and grown at 25° C. for overnight. Plates were centrifuged for 10 min at 3,000×g and phage-containing supernatants were transferred to fresh plates for the ELISA assays.

For anchor-binder phage ELISA, ELISA plates (Nunc MaxiSorp™, Thermo Fisher Scientific) were coated with 100 μL 5 g/mL streptavidin in coating buffer (100 mM carbonate buffer, pH 8.6) at 4° C. for overnight. After washing with 3×0.05% PBST (1×PBS with 0.05% v/v Tween 20), each well was added with 100 μL 1 μM biotinylated CBD and incubated at r.t. for 1 h. Wells were washed with 5×0.05% PBST, blocked with 1% casein in 1×PBS, and then added with 100 μL phage supernatants. Phage particles were incubated with CBD in plates at r.t. for 1 h. Wells were washed with 10×0.05% PBST, added with 100 μL HRP-M13 major coat protein antibody (RL-ph1, Santa Cruz Biotechnology; 1:2000 dilution with 1×PBS with 1% casein), and incubated at r.t. for 1 h. A colorimetric detection was performed using a 1-Step Ultra TMB ELISA substrate solution (Thermo Fisher Scientific) and OD450 was measured with a SpectraMax™ Plus 384 microplate reader (Molecular Devices).

The dimerization-binder phage ELISA used the plate-immobilized anchor binder as the bait. ~100 nM biotinylated anchor binder, CA-14, was bound to a streptavidin-coated plate prepared as above described. The immobilized CA-14 was bound to different concentrations of CBD in 1×PBS, pH 7.4, to form the anchor binder-CBD complex before binding to phage-displayed dimerization binders. Other steps were performed similarly to the anchor-binder phage ELISA.

5. Protein Expression and Purification

All nanobodies were expressed as a C-terminal Avi-Tagged and His-tagged form in *E. coli* and purified by Ni-affinity and size-exclusion chromatography. In brief, *E. coli* strain WK6 was transformed with the expression constructs and grown in TB medium at 37° C. to an OD600 of ~0.7 before induction with 1 mM isopropyl-β-D-galactopyranoside (IPTG) at 28° C. for overnight. Harvested cell pellets from 1-liter cultures were resuspended in 15 mL ice-cold TES buffer (0.2 M Tris-HCL pH 8.0, 0.5 mM EDTA, 0.5 M sucrose) and incubated with gently shaking on ice for 1 h. To release proteins from the periplasm by osmotic shock, the resuspended pellets were added with 30 mL of TES/4 buffer (1:4 dilution of the TES buffer in ddH$_2$O) and gently shaken on ice for 45 min. Cell debris was removed by centrifugation at 15,000×g, 4° C. for 30 mins. The supernatant was loaded onto a 5 mL HisTrap™ column (GE Healthcare) pre-equilibrated with the lysis buffer (50 mM sodium phosphate, pH 8.0, 300 mM NaCl, 10 mM imidazole, 10% glycerol). The column was washed with a washing buffer (50 mM sodium phosphate, pH 8.0, 300 mM NaCl, 20 mM imidazole, 10% glycerol) and then His-tagged proteins were eluted with an elution buffer (50 mM sodium phosphate, pH 8.0, 300 mM NaCl, 250 mM imidazole, 10% glycerol). Eluates were concentrated with an Amicon™ Ultra-15 centrifugal filter unit (3 kDa cutoff, Millipore). Concentrated proteins were loaded onto a HiLoad™ 16/600 Superdex 200 pg column (GE Healthcare) pre-equilibrated with a storage buffer (1×PBS, 5% glycerol). Eluted proteins were concentrated, examined by SDS-PAGE, and quantified by a Bradford assay (BioRad), then flash frozen in 100 μL aliquots by liquid N$_2$ and stored at −80° C.

6. Protein Biotinylation

Nanobodies bearing AviTag were biotinylated by BirA using a BirA-500 kit (Avidity).[5] Typically, 90 μL BiomixA (10× concentration: 0.5 M bicine buffer, pH 8.3), 90 μL BiomixB (10× concentration: 100 mM ATP, 100 mM Mg(OAc)$_2$, 500 μM d-biotin), 4 μL 1 mg/mL BirA, and 216 μL ddH$_2$O were added to 500 μL~1 mg/mL AviTagged nanobodies to a final volume of 900 μL. The biotinylation mixture was incubated at r.t. for 1 h and then loaded onto a HiPrep 26/10 desalting column (GE Healthcare) pre-equilibrated with a storage buffer (1×PBS, 5% glycerol). Eluted proteins were concentrated, examined by SDS-PAGE, and quantified by the Bradford assay, flash frozen in 100 μL aliquots by liquid N$_2$, and stored at −80° C.

7. BioLayer Interferometry

The nanobody binding kinetics was analyzed using an Octet™ RED96 system (ForteBio) and Streptavidin (SA) or Super Streptavidin (SSA) biosensors. For the anchor-binder analysis, 200 nM biotinylated anchor binders were immobilized on SSA biosensors with a binding assay buffer (1×PBS, pH 7.4, 0.05% Tween 20, 0.2% BSA, 3% methanol; Note: because CBD and THC were dissolved in methanol to make stock solutions, 3% methanol was added to the buffer to fairly compare samples and controls). Serial dilutions of CBD and THC were used for the anchor binder assays. Dissociation constants (K$_D$s) of anchor binder-ligand interactions were calculated based on a steady-state analysis using Octet™ RED96 data analysis software. For the dimerization-binder analysis, 200 nM biotinylated dimerization binders were immobilized on SA biosensors with the binding assay buffer and then assayed with 1 μM CA-14 pre-equilibrated with serial dilutions of CBD or THC. K$_D$s, k$_{on}$s, and k$_{off}$s of the interactions between anchor binder-ligand complexes and dimerization binders were calculated based on a heterogeneous ligand model global fit (2:1) of the data and simulated binding equilibria of the anchor binder and CBD described in Supplementary Notes.

8. Analytical SEC

Anchor and dimerization nanobodies were analyzed by SEC with a Superdex™ 75 increase 10/300 GL column (GE Healthcare). For non-crosslinked samples, 500 μL~30 μM nanobodies were injected into the column equilibrated with 1×PBS and eluted at a flow rate of 0.75 mL/min at 4° C. The column was calibrated with molecular weight standards (Sigma-Aldrich). Crosslinked samples were prepared by incubating 5 or 10 μM proteins in the presence or absence of CBD in 1×PBS with 0.1 mM BS(PEG)$_5$ at r.t. for 30 mins. 500 μL crosslinked samples were injected to the column.

9. ELISA-Like Assay to Determine CBD Detection Sensitivity

Urine and saliva samples were collected from three healthy volunteers (two males and one female). The urine and saliva samples were spun for 3 minutes at 14,000×g and the supernatants were diluted by ⅕ with 1×PBS, pH 7.4, and spiked with CBD. Serial dilutions (0 to 1,000 nM CBD) of samples were used for the dimerization binder ELISA similarly to that described above. Each dilution was repeated 8 times and Limit of Detection (LoD) was calculated by mean$_{blank}$+3×SD$_{blank}$.

Supplemental Notes

1. Binding Model Expectations Based on Previous CID Systems and Ligand Docking

Figure 11:
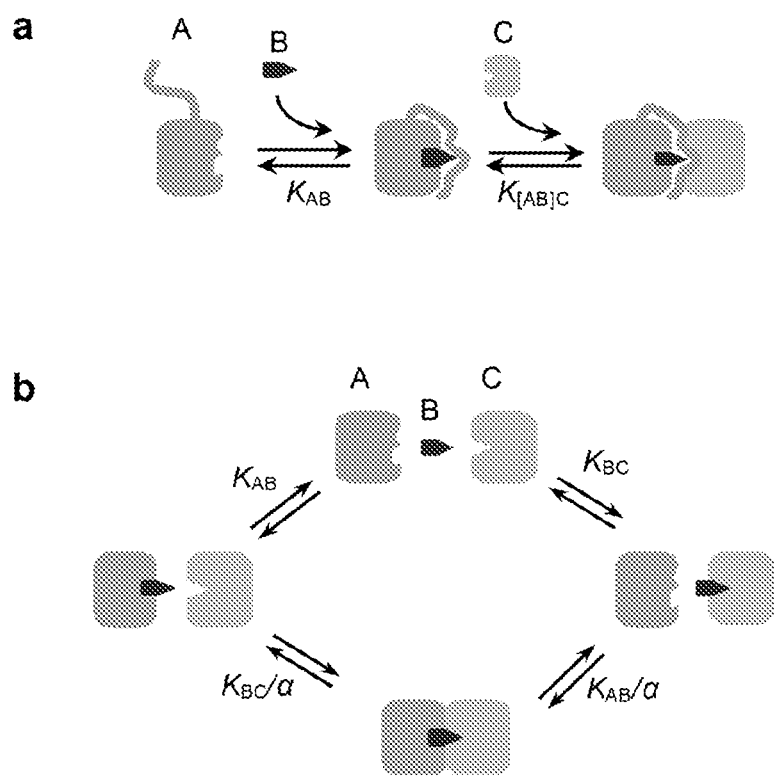
FIG. 11(a)-(b). Two mechanisms explaining CID. (a) Conformational change induced binding typical of the gibberellin CID system. (b) Three-body binding equilibrium typical of the rapamycin CID system FIG. 12. Example of a cooperative binding model. Approximating the binding behavior of a BLI experiment where the concentration of immobilized ligand (in this case DB-21) is much smaller than the analyte (in this case CA-14): [L]>>[A]. α was set to 1,000 and K$_{AB}$ and K$_{BC}$ was set using BLI data from the CA-14, DB-21 and the dimerization.

Two mechanisms can explain the currently existing CID systems[6] (FIG. 11): a) the chemical inducer works as a bridge between the two proteins dimerizing, and b) the chemical induces a large structural change upon binding one of the proteins, this structural change then allows for dimerization to the other protein.

The gibberellin CID system is an example of protein dimerization which depends on a necessary conformational change in one of the dimerizing proteins. In the gibberellin CID system, the GID1A domain contains an N-terminal extension that, upon binding to gibberellin, forms a stable interaction surface for the DELLA domain.[7] In this system gibberellin is completely buried in a deep binding pocket and only the conformationally changed GID1A domain is free to bind the DELLA domain. Such system is kinetically simple with only two dissociation constants defining the system (FIG. 11a).

The rapamycin CID system is an example of the "bridge molecule" mechanism. In this system the protein FKBP binds to one part of the rapamycin molecule, while the protein FRB binds to the other end.[8,9] In such systems, because both proteins can bind independently to the small molecule, the kinetics are more complex defined by two dissociation constants and a parameter, α, quantifying "binding cooperation" (FIG. 11b). When α>0, this is termed positive cooperation and represents a binding enhancement upon ternary complex formation. When α<0, this is termed negative cooperation and represents a binding diminishment upon ternary complex formation. Others have studied the three-body binding equilibrium in great detail.[10] Using established affinities,[8] the rapamycin CID system has positive corporation of ~2,000.

Figure 13:
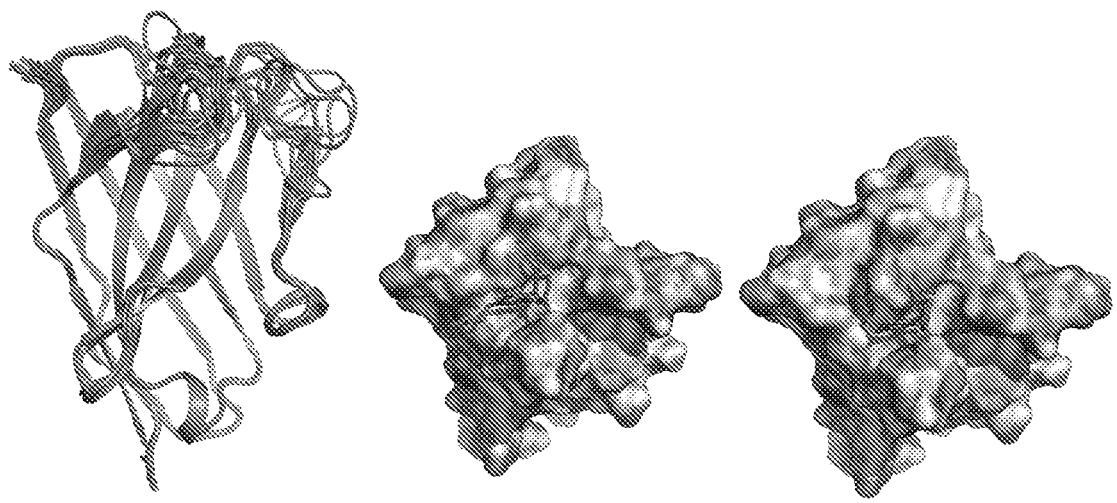
FIG. 13. Docking results. (left) The 16 low-energy models of the CA-14 construct. (middle,right) The two putative binding models of CBD suggested from the docking simulation.

We hypothesize that our CBD CID system works by either of the two above described binding mechanisms. We primarily tested CBD anchor 14 (CA-14) which has relatively short CDR sequences (Table 1). With short CDRs it is unlikely that CBD binding induces a gibberellin-like conformational change through CDR loop stabilization. This also makes it unlikely that CBD is completely buried with no exposed parts, although, we cannot rule out this possibility. Indeed, our docking study suggests that CBD is still exposed after binding to CA-14 (FIG. 13). This leads us to believe that CBD induced dimerization is governed by the "bridge molecule" mechanism similar to the rapamycin CID. The distinction between these binding models is important because binding through a bridge molecule leads to a system with possible auto-inhibition,[10] also known as the hook effect or the prozone effect. Auto-inhibition negatively affects dimerization at high concentrations of the bridge molecule because it competes against dimerization. The effect is described in detail in.[10]

Bio Layer Interferometry to determine binding kinetics

In order to determine the binding kinetics of our nanobody CID system we performed a series of bio layer interferometry (BLI) experiments. In all experiments we used an Octet RED96 system (ForteBio) and Streptavidin Biosensors (ForteBio). 200 nM biotinylated protein (FIGS. 7b & 4C) were immobilized on biosensors (Super Streptavidin, SSA used for anchor binder; Streptavidin, SA used for dimerization binder) with a binding assay buffer (1×PBS, pH 7.4, 0.05% Tween 20, 0.2% BSA, 3% methanol; Note: because CBD and THC were dissolved in methanol to make stock solutions, 3% methanol was added to the buffer to fairly compare samples and controls). Ligand loading was followed by a quenching step using free biotin. All experiments were performed using four measurements to control for sensor drift and unspecific binding:

No ligand, no analyte
With ligand, no analyte
No ligand, with analyte
With ligand, with analyte The ligand is defined as the protein loaded to the SSA sensor and the analyte is either protein or small molecule in solution. The final sensorgrams were derived from: (d-c)-(b-a)

Figure 8:
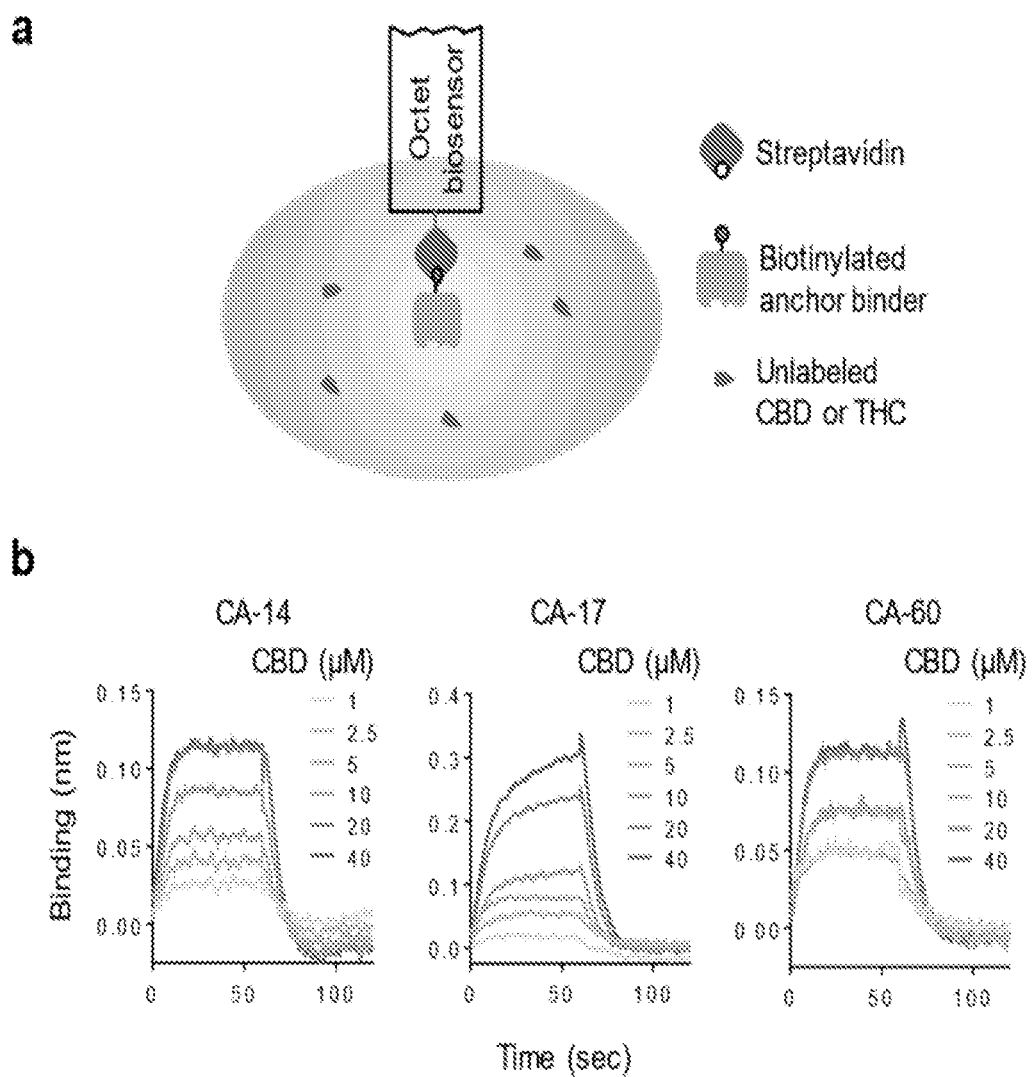
FIG. 8(a)-(c). (a) BLI setup for the anchor binder-ligand interaction analysis. (b) BLI sensorgrams showing CBD binding to a panel of anchor binders. CA-14 was done with one sensor per condition, while others are using a single sensor for all conditions. (c) Steady-state binding curve fitting.
Figure 8:
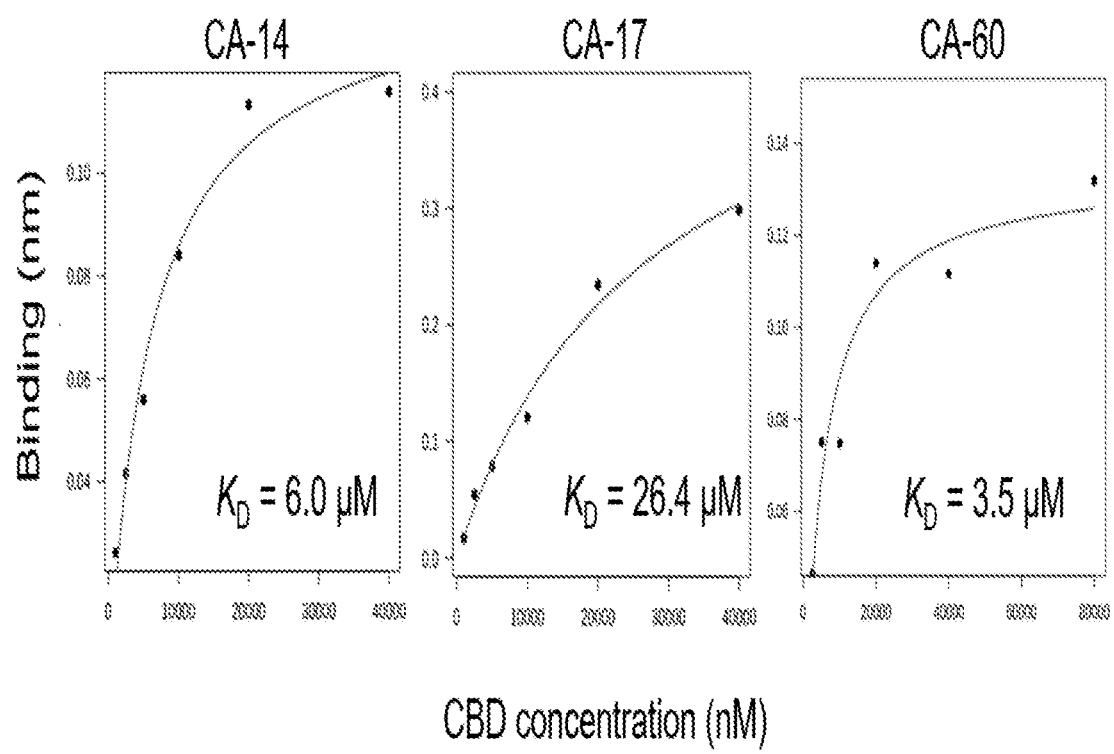

We first determined the binding affinity between the CBD anchor 14 (CA-14) and CBD via steady-state analysis (FIG. 8). For this experiment, BLI sensorgrams were collected using one SSA sensor per CBD concentration over six concentrations. Data analysis were performed in ForteBio DataAnalysis v9 using a global 1:1 model (standard Langmuir isotherm). The global model requires binding parameters for all six concentrations to be the same, except the ligand loading amount, $R_{max}$, which was unlinked to allow for differences in ligand loading caused by sensor variance. Steady-state analysis was then performed using the steady-state values estimated by this global model. We performed a similar experiment, using a single sensor for multiple concentrations, on the dimerization binders (DB). We observed minimal binding between DBs and CBD, but the KDs are too weak to be determined (data not shown).

Figure 9:
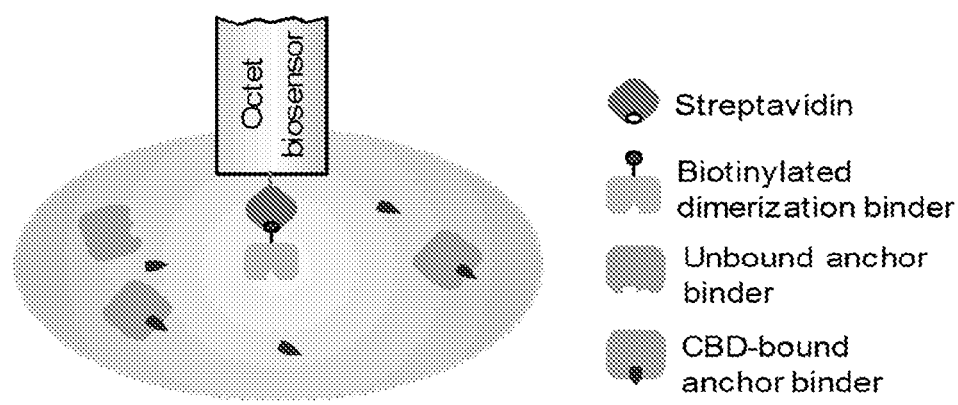
FIG. 9(a)-(b). (a) BLI setup for the anchor binder-dimerization binder interaction analysis. (b) BLI sensorgrams showing the anchor binder-dimerization binder interactions in the presence of CBD or THC.
Figure 9:
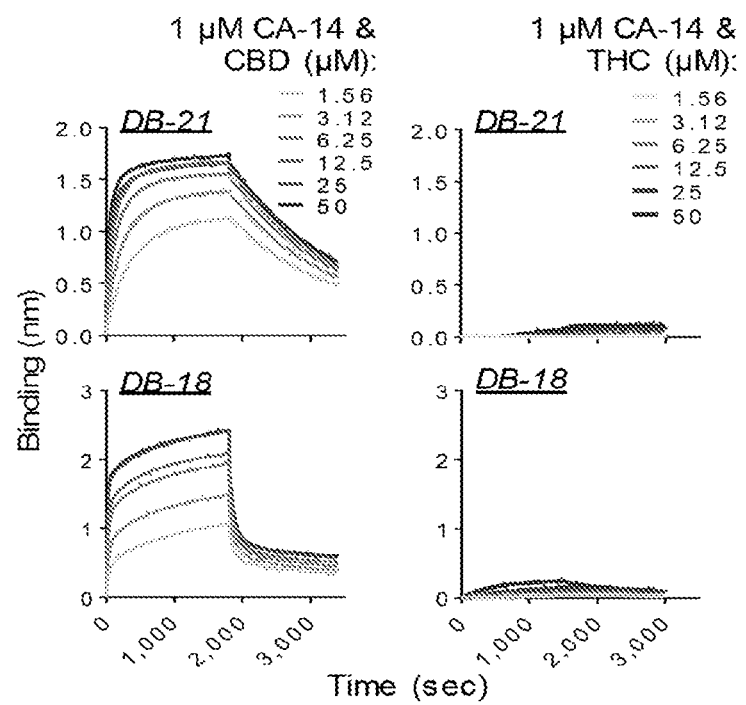

Next, we wanted to determine the binding affinity between CA-14 bound to CBD (referred to as CA-14*) and a panel of DBs. We observed no detectable binding between CA-14 and any of the DBs (FIG. 3a). We also rely on the observation that the DBs have weak binding to CBD, and therefore we can assume that only CA-14* binds the DB loaded to the sensor. We control the CA-14* concentration by using a fixed concentration of 1 µM CA-14 pre-incubated to equilibrium with six different concentrations of CBD. These CA-14* concentrations were then allowed to bind to DB loaded SA sensors and binding was measured (FIG. 9). One sensor was used per CBD concentration. The sensorgrams initially showed a fast binding phase which was followed by a phase with slow binding. Such biphasic binding is an indication of a heterogeneous surface.[11] Attempts to optimize the binding behavior was unsuccessful so we turned towards fitting methods that take into account multiple binding phases. One such method is implemented as a publicly available software called EVILFIT.[12] EVILFIT integrates over a grid of possible affinities and assigns probabilities to each. Using CA-14's affinity to CBD, we calculated the CA-14* concentration at equilibrium for the different CBD concentrations and used this as the analyte concentrations to EVILFIT. At the two largest CBD concentrations we observed CBD based auto-inhibition of dimerization (discussed below) and therefore these were removed. When restricting our analysis to the four smallest CBD concentrations, EVILFIT showed good agreement between the data and the fit (data not shown). Using these fits, we located the affinity distribution for the first binding phase and integrated over this to derive a point estimate of the affinities between CA-14 and the DBs (Table 5).

Suggested Binding Model for CA-14 Dimerizing DB-21

CA-14 and DB-21 is our most well characterized binding pair. BLI analysis established the binding affinity between CA-14 and CBD to be 6.0 µM (FIG. 8). Docking studies suggested that CBD bound CA-14 in a way that exposes smaller parts of CBD (FIG. 13) potentially acting as a bridge to DB-21. This hypothesis is supported by the characteristic auto-inhibition we observed in our ELISA titration data (data not shown), indicating that CBD at high concentrations is competing with dimerization. We observe a similar kind of auto-inhibition at the two highest CBD concentrations in our BLI assay (FIG. 9).

If CBD is acting as a bridging molecule it must also bind DB-21. However, another BLI analysis showed that DB-21 only binds CBD very weakly (data not shown), and therefore bridging cannot by itself explain the strong dimerization we observe (FIG. 9). The observations can, however, be explained by positive cooperation, which enhances dimerization, and has before been shown to cause ~2,000 enhancement in rapamycin inducible dimerization.[8]

Figure 12:
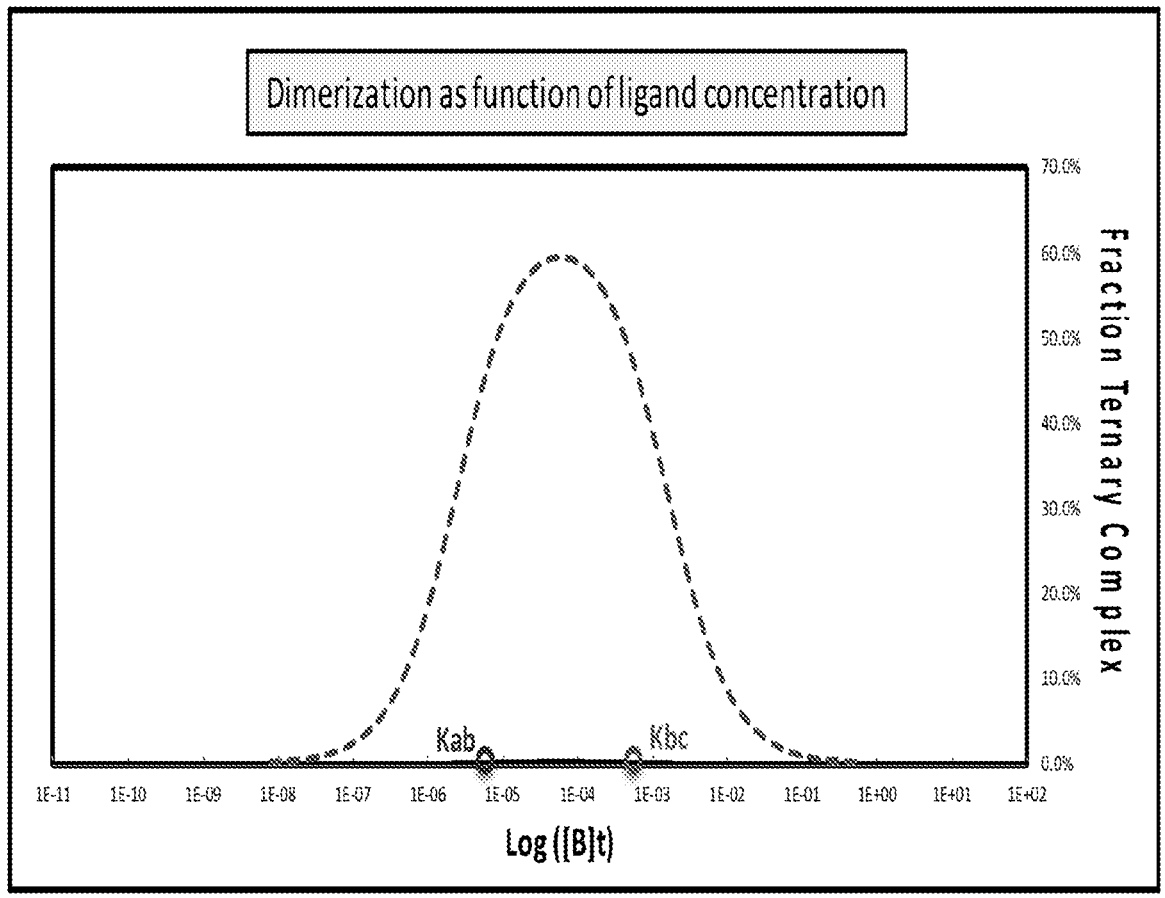

Douglass et al.[10] derives the equilibrium solution to such three-body binding systems with cooperation. Unfortunately, we cannot reliably measure DB-21's affinity to CBD ($K_{BC}$ in FIG. 11b) due to its weak affinity and the limited solubility of CBD. However, we have been able to determine CBD's affinity to CA-14 and CA-14*'s affinity to DB-21 ($K_{AB}$ and $K_{BC}/\alpha$ in FIG. 11b). As for the cooperation parameter, $\alpha$, it must be so large that $K_{BC}$ turns form undetectable by BLI to 56 nM ($K_{BC}/\alpha$). $\alpha=1,000$ is a reasonable guess, also within the limit of what has been observed in the rapamycin CID, making $K_{BC}$ equal to 56 µM. Plugging this into the three-body binding model from Douglass et al. (FIG. 12), we get an explanation for the auto-inhibition we observe in ELISA titrations, as well as a reason why the two highest CBD concentrations in our BLI sensorgrams of dimerization (FIG. 9) does not follow a standard steady-state curve.

2. Docking Studies of CBD Binding CA-14

Rosetta™-based protein modelling and protein/ligand docking was carried out with the anchor binder CA-14 and CBD. First, models of the nanobody CA-14 were constructed with RosettaCM™.[13] Modelling used four template structures (pdb ids: 1mqk, 1t2j, 1uac, and 6cnw). The command used to run RosettaCM™ follows:

```
$ROSETTA/source/bin/rosetta_scripts.default.linuxgccrelease \
   -in:file:fasta CA14.fasta \
   -parser: :protocol hybrid.xml \
   -relax: :dualspace \
   -relax:default_repeats 5 \
   -default_max_cycles 200 \
   -score: weights beta_cart \
   -beta
```

The command above was provided the following XML script:

```
<ROSETTASCRIPTS>
  <SCOREFXNS>
    <ScoreFunction name="stage1" weights="score3">
      <Reweight scoretype="atom_pair_constraint" weight="0.1" />
    </ ScoreFunction>
    <ScoreFunction name ="stage2" weights="score4_smooth_cart">
      <Reweight scoretype="atom_pair_constraint" weight="0.1" />
    </ ScoreFunction>
    <ScoreFunction name ="fullatom" weights ="beta_cart">
      <Reweight scoretype="atom_pair_constraint" weight="0.1" />
    </ ScoreFunction>
  </ SCOREFXNS>
  <MOVERS>
    <Hybridize name ="hybridize" stage1_scorefxn="stage1"
        stage2_scorefxn="stage2" fa_scorefxn="fullatom" batch="1">
      <Template pdb="1mqkH_201.pdb" weight="1.0" cst_file="AUTO" / >
      <Template pdb="1t2jA_202.pdb" weight="1.0" cst_file="AUTO" / >
      <Template pdb="6cnwA_203.pdb" weight="1.0" cst_file="AUTO" / >
      <Template pdb="1uacH_204.pdb" weight="1.0" cst_file="AUTO" / >
    </ Hybridize>
  </ MOVERS>
  <PROTOCOLS>
    <Add mover="hybridize" / >
  </ PROTOCOLS>
  <OUTPUT scorefxn="fullatom" / >
</ ROSETTASCRIPTS>
```

RosettaCM™ was run in parallel, generating a total of 400 initial models. The 16 lowest energy models (FIG. 13) were then used as receptor structures in ligand docking.

Ligand docking used an unpublished docking protocol in Rosetta, with a recently developed generalized energy function using prior methodology[14] for energy function fitting.

A CBD ligand conformation was generated using OpenBabel™.[15] This model was then minimized using AM1 and AM1-BCC partial charges were generated with antechamber.[16] Finally, the refined small molecule was converted to a Rosetta parameter file with the following command:

```
python $ROSETTA/source/scripts/python/public/generic_potential/
    mol2genparams.py -amide_chi -s LG1.mol2
```

Docking in Rosetta™ was carried out running the following command:

```
$ROSETTA/source/bin/rosetta_scripts.linuxgccrelease \
    -database ~/Rosetta_efunc/database \
    -s input.pdb \
    -parser:protocol dock.xml \
    -beta_cart \
    -extra_res_fa CBD.params \
    -no_autogen_cart_improper
```

The input XML, dock.xml:

```
$ROSETTA/source/bin/rosetta_scripts.linuxgccrelease \
  -database ~ /Rosetta_efunc/database \
  -s input.pdb \
  -parser:protocol dock.xml \
  -beta_cart \
  -extra_res_fa CBD.params \
  -no_autogen_cart_improper
The input XML, dock.xml:
<ROSETTASCRIPTS>
<SCOREFXNS>
  <ScoreFunction name="dockscore" weights="beta">
    <Reweight scoretype="fa_rep" weight="0.2" / >
    <Reweight scoretype="coordinate_constraint" weight="0.1" / >
  </ ScoreFunction>
  <ScoreFunction name ="relaxscore" weights="beta_cart" / >
</ SCOREFXNS>
<MOVERS>
  <GALigandDock name ="dock" runmode ="dockflex" scorefxn="dockscore"
      scorefxn_relax="relaxscore" sidechains ="auto">
    <Stage repeats ="10 " npool="100" pmut="0.2" smoothing="0.375"
        rmsdthreshold="2.0" maxiter="50" pack_cycles="100 "
        ramp_schedule="0.1, 1.0"/>
  </ GALigandDock>
</ MOVERS>
<PROTOCOLS>
  <Add mover="dock" / >
</ PROTOCOLS>
<OUTPUT scorefxn="relaxscore" / >
<ROSETTASCRIPTS>
```

The input files from this run were the ten lowest-energy receptor structures from stage 1. Initially, input ligands were placed in a random orientation such that the ligand center of mass was coincident with the C-beta of residue 33, the residue closest to the center of mass of the variable loops in the nanobody.

The previous XML samples an ensemble of 100 structures in a single trajectory. We ran a total of 160 such trajectories, ten trajectories for each of the 16 initial models, generating a total of 16,000 models. Visual inspection of the lowest-energy 20 docked conformations yielded two unique configurations, illustrated in FIG. 13.

REFERENCES (1) Qi, L. W.; Yamamoto, N.; Meijler, M. M.; Altobell, L. J.; Koob, G. F.; Wirsching, P.; Janda, K. D. *J. Med. Chem.* 2005, 48, 7389.

(2) Moutel, S.; Bery, N.; Bernard, V.; Keller, L.; Lemesre, E.; de Marco, A.; Ligat, L.; Rain, J. C.; Favre, G.; Olichon, A.; Perez, F. *eLife* 2016, 5.
(3) Roehr, J. T.; Dieterich, C.; Reinert, K. *Bioinformatics* 2017, 33, 2941.
(4) Crooks, G. E.; Hon, G.; Chandonia, J. M.; Brenner, S. E. *Genome Res.* 2004, 14, 1188.
(5) Beckett, D.; Kovaleva, E.; Schatz, P. J. *Protein Sci.* 1999, 8, 921.
(6) Stanton, B. Z.; Chory, E. J.; Crabtree, G. R. *Science* 2018, 359.
(7) Murase, K.; Hirano, Y.; Sun, T. P.; Hakoshima, T. *Nature* 2008, 456, 459.
(8) Banaszynski, L. A.; Liu, C. W.; Wandless, T. J. *J. Am. Chem. Soc.* 2005, 127, 4715.
(9) Liang, J.; Choi, J.; Clardy, J. *Acta Crystallogr D Biol. Crystallogr* 1999, 55, 736.
(10) Douglass, E. F.; Miller, C. J.; Sparer, G.; Shapiro, H.; Spiegel, D. A. *J. Am. Chem. Soc.* 2013, 135, 6092.
(11) Schuck, P.; H., Z. *Methods. Mol. Biol.* 2010, 627, 15.
(12) Zhao, H. Y.; Gorshkova, II; Fu, G. L.; Schuck, P. *Methods* 2013, 59, 328.
(13) Song, Y. F.; DiMaio, F.; Wang, R. Y. R.; Kim, D.; Miles, C.; Brunette, T. J.; Thompson, J.; Baker, D. *Structure* 2013, 21, 1735.
(14) Park, H.; Bradley, P.; Greisen, P.; Liu, Y.; Mulligan, V. K.; Kim, D. E.; Baker, D.; DiMaio, F. *J. Chem. Theory. Comput.* 2016, 12, 6201.
(15) O'Boyle, N. M.; Banck, M.; James, C. A.; Morley, C.; Vandermeersch, T.; Hutchison, G. R. *J. Cheminform.* 2011, 3.
(16) Wang, J. M.; Wang, W.; Kollman, P. A.; Case, D. A. *J. Mol. Graph. Model.* 2006, 25, 247.

We claim:

1. A single-chain antibody, comprising a set of complementarity-determining regions (CDRs) selected from the group consisting of a CDR1, CDR2, and CDR3 combination comprising the amino acid sequences:
   (a) SEQ ID NO:1, SEQ ID NO:2, and SEQ ID NO:3;
   (b) SEQ ID NO:4, SEQ ID NO:5, and SEQ ID NO: 6;
   (c) SEQ ID NO:7, SEQ ID NO:8, and SEQ ID NO: 9;
   (d) SEQ ID NO:10, SEQ ID NO:11, and SEQ ID NO: 12;
   (e) SEQ ID NO:13, SEQ ID NO:14, and SEQ ID NO: 15;
   (f) SEQ ID NO:16, SEQ ID NO:17, and SEQ ID NO: 18;
   (g) SEQ ID NO:19, SEQ ID NO:20, and SEQ ID NO:21;
   (h) SEQ ID NO:22, SEQ ID NO:23, and SEQ ID NO:24;
   (i) SEQ ID NO:25, SEQ ID NO:26, and SEQ ID NO:27;
   (j) SEQ ID NO:28, SEQ ID NO:29, and SEQ ID NO:30;
   (k) SEQ ID NO:31, SEQ ID NO:32, and SEQ ID NO:33
   (l) SEQ ID NO:34, SEQ ID NO:35, and SEQ ID NO:36;
   (m) SEQ ID NO:37, SEQ ID NO:38, and SEQ ID NO:39;
   (n) SEQ ID NO:40, SEQ ID NO:41, and SEQ ID NO:42;
   (o) SEQ ID NO:43, SEQ ID NO:44, and SEQ ID NO:45;
   (p) SEQ ID NO:46, SEQ ID NO:47, and SEQ ID NO:48;
   (q) SEQ ID NO:49, SEQ ID NO:50, and SEQ ID NO:51;
   (r) SEQ ID NO:52, SEQ ID NO:53, and SEQ ID NO:54;
   (s) SEQ ID NO:55, SEQ ID NO:56, and SEQ ID NO:57;
   (t) SEQ ID NO:58, SEQ ID NO:59, and SEQ ID NO: 60;
   (u) SEQ ID NO:61, SEQ ID NO:62, and SEQ ID NO: 63;
   (v) SEQ ID NO:64, SEQ ID NO:65, and SEQ ID NO:66;
   (w) SEQ ID NO:67, SEQ ID NO:68, and SEQ ID NO:69;
   (x) SEQ ID NO:70, SEQ ID NO:71, and SEQ ID NO: 72;
   (y) SEQ ID NO:73, SEQ ID NO:74, and SEQ ID NO:75;
   (z) SEQ ID NO:76, SEQ ID NO:77, and SEQ ID NO:78; or
   (aa) SEQ ID NO:79, SEQ ID NO:80, and SEQ ID NO:81.

2. The single-chain antibody of claim 1, wherein the single-chain antibody comprises a scaffold comprising an amino acid sequence at least 50% identical to the amino acid sequence of SEQ ID NO:82

```
                                        (SEQ ID NO: 82)
EVQLQASGGGFVQPGGSLRLSCAASG-(CDR1)-MGWFRQAPGKEREFV

SAIS-(CDR2)-YYADSVKGRFTISRDNSKNTVYLQMNSLRAEDTATYY

CA-(CDR3)-YWGQGTQVTVSS,
``` wherein CDR1, CDR2, and CDR3 comprise a CDR1, CDR2, and CDR3 combination according to any one of options (a)-(aa) in claim 1.

3. The single-chain antibody of claim 1, wherein the single-chain antibody comprises a scaffold comprising an amino acid sequence at least 50% identical to the amino acid sequence:

```
                                                  (SEQ ID NO: 83)
EVX1LQASGGX2X3VQPGGSLRLSX4AASG-(CDR1)-MGWX5RQX6P

X7KEREFVSAIS-(CDR2)-YYX8DX9VKGRFTISRDNX10KNTX11YL

QMX12SLX13X14EDTAX15YYCX16-(CDR3)-YWGQGTQVTVSS;
```
wherein
X1 is K, Q, N, R, D, or E;
X2 is D, G, E, A, V, L, or I;
X3 is L, F, W, G, A, V, L, or I;
X4 is K, R, D, E, N, or Q,
X5 is V, P, G, A, L, I, or M;
X6 is T, A, S, G, V, L, or I;
X7 is E, G, D, A, V, L, or I;
X8 is P, A, M, G, V, L, or I;
X9 is T, or S;
X10 is A, S, M, G, V, L, or I;
X11 is L, V, G, A, or I;
X12 is S, N, Q, or T;
X13 is K, R, D, or E;
X14 is S, A, T, G, V, L, or I;
X15 is M, T, V, L, or I;
X16 is V, G, L, I, or A; and
   wherein CDR1, CDR2, and CDR3 comprise a CDR1, CDR2, and CDR3 combination according to any one of options (a)-(aa) in claim 1.

4. The single-chain antibody of claim 1, wherein CDR1 comprises the amino acid sequence of SEQ ID NO:1, CDR2 comprises the amino acid sequence of SEQ ID NO:2, and CDR3 comprises the amino acid sequence of SEQ ID NO:3.

5. The single-chain antibody of claim 1, further comprising one or more functional domains.

6. The single-chain antibody of claim 1, wherein the single-chain antibody is bound to a solid support.

7. A fusion protein, comprising:
   (a) a first single-chain antibody, comprising the set of complementarity determining regions (CDRs) of SEQ ID NO:1, 2, and 3;
   (b) a second single-chain antibody, comprising a set of complementarity determining regions (CDRs) selected from the group consisting of a CDR1, CDR2, and CDR3 combination according to any one of options (d)-(aa) in claim 1; and
   (c) a linker between the first single-chain antibody and the second single-chain antibody.

8. The fusion protein of claim 7, wherein the second single-chain antibody comprises a set of complementarity determining regions (CDRs) selected from the group consisting of a CDR1, CDR2, and CDR3 combination comprising the amino acid sequences:
   (i) SEQ ID NO:70, SEQ ID NO:71, and SEQ ID NO:72;
   (ii) SEQ ID NO:25, SEQ ID NO:26, and SEQ ID NO:27;
   (iii) SEQ ID NO:40, SEQ ID NO:41, and SEQ ID NO:42; or
   (iv) SEQ ID NO:61, SEQ ID NO:62 and SEQ ID NO: 63.

9. A kit, comprising:
   (a) a first single-chain antibody, comprising the set of complementarity determining regions (CDRs) of SEQ ID NO:1, 2, and 3;
   (b) a second single-chain antibody, comprising a set of complementarity determining regions (CDRs) selected from the group consisting of a CDR1, CDR2, and CDR3 combination according to any one of options (d)-(aa) in claim 1; and
   (c) cannabidiol, or a salt thereof.

10. The kit of claim 9, wherein the second single-chain antibody comprises a set of complementarity determining regions (CDRs) selected from the group consisting of a CDR1, CDR2, and CDR3 comprising the amino acid sequences:
   (i) SEQ ID NO:70, SEQ ID NO:71, and SEQ ID NO: 72;
   (ii) SEQ ID NO:25, SEQ ID NO:26, and SEQ ID NO:27;
   (iii) SEQ ID NO:40, SEQ ID NO:41, and SEQ ID NO:42; or
   (iv) SEQ ID NO:61, SEQ ID NO:62 and SEQ ID NO: 63.

11. The kit of claim 9, wherein the first single-chain antibody comprises a scaffold comprising an amino acid sequence at least 50% identical to the amino acid sequence:

```
                                                  (SEQ ID NO: 82)
EVQLQASGGGFVQPGGSLRLSCAASG-(CDR1)-MGWFRQAPGKEREFV

SAIS-(CDR2)-YYADSVKGRFTISRDNSKNTVYLQMNSLRAEDTATYY

CA-(CDR3)-YWGQGTQVTVSS
``` wherein CDR1 comprises the amino acid sequence of SEQ ID NO:1, CDR2 comprises the amino acid sequence of SEQ ID NO:2, and CDR3 comprising the amino acid sequence of SEQ ID NO:3.

12. The kit of claim 11, wherein the second single-chain antibody comprises a scaffold comprising an amino acid sequence at least 50% identical to the amino acid sequence:

```
                                                  (SEQ ID NO: 82)
EVQLQASGGGFVQPGGSLRLSCAASG-(CDR1)-MGWFRQAPGKEREFV

SAIS-(CDR2)-YYADSVKGRFTISRDNSKNTVYLQMNSLRAEDTATYY

CA-(CDR3)-YWGQGTQVTVSS;
``` wherein CDR1, CDR2, and CDR3 comprise the amino acid sequences:
   (i) SEQ ID NO:70, SEQ ID NO:71, and SEQ ID NO: 72;
   (ii) SEQ ID NO:25, SEQ ID NO:26, and SEQ ID NO:27;
   (iii) SEQ ID NO:40, SEQ ID NO:41, and SEQ ID NO:42; or
   (iv) SEQ ID NO:61, SEQ ID NO:62, and SEQ ID NO: 63.

13. The kit of claim 11, wherein the second single-chain antibody comprises a scaffold comprising an amino acid sequence at least 50% identical to the amino acid sequence:

```
                                                  (SEQ ID NO: 82)
EVQLQASGGGFVQPGGSLRLSCAASG-(CDR1)-MGWFRQAPGKEREFV

SAIS-(CDR2)-YYADSVKGRFTISRDNSKNTVYLQMNSLRAEDTATYY

CA-(CDR3)-YWGQGTQVTVSS;
``` wherein CDR1 comprises the amino acid sequence of SEQ ID NO:70, CDR2 comprises and amino acid sequence of SEQ ID NO:71, and CDR3 comprises the amino acid sequence of SEQ ID NO:72.

14. The kit of claim 9, wherein the first single-chain antibody comprises a scaffold comprising an amino acid sequence at least 50% identical to the amino acid sequence:

(SEQ ID NO: 83)
EVX1LQASGGX2X3VQPGGSLRLSX4AASG-(CDR1)-MGWX5RQX6PX7KEREFVSAIS-(CDR2)-YYX8DX9VKGRFTISRDNX10KNTX11YLQMX12SLX13X14EDTAX15YYCX16-(CDR3)-YWGQGTQVTVSS;

wherein
   X1 is K, Q, N, R, D, or E;
   X2 is D, G, E, A, V, L, or I;
   X3 is L, F, W, G, A, V, L, or I;
   X4 is K, R, D, E, N, or Q;
   X5 is V, P, G, A, L, I, or M;
   X6 is T, A, S, G, V, L, or I;
   X7 is E, G, D, A, V, L, or I;
   X8 is P, A, M, G, V, L, or I;
   X9 is T, or S;
   X10 is A, S, M, G, V, L, or I;
   X11 is L, V, G, A, or I;
   X12 is S, N, Q, or T;
   X13 is K, R, D, or E;
   X14 is S, A, T, G, V, L, or I;
   X15 is M, T, V, L, or I;
   X16 is V, G, L, I, or A; and
     wherein CDR1 comprises the amino acid sequence of SEQ ID NO:1, CDR2 comprises the amino acid sequence of SEQ ID NO:2, and CDR3 comprising the amino acid sequence of SEQ ID NO:3.

15. The kit of claim 14, wherein the second single-chain antibody comprises a scaffold comprising an amino acid sequence at least 50% identical to the amino acid sequence:

(SEQ ID NO: 83)
EVX1LQASGGX2X3VQPGGSLRLSX4AASG-(CDR1)-MGWX5RQX6PX7KEREFVSAIS-(CDR2)-YYX8DX9VKGRFTISRDNX10KNTX11YLQMX12SLX13X14EDTAX15YYCX16-(CDR3)-YWGQGTQVTVSS;

wherein
   X1 is K, Q, N, R, D, or E;
   X2 is D, G, E, A, V, L, or I;
   X3 is L, F, W, G, A, V, L, or I;
   X4 is K, R, D, E, N, or Q;
   X5 is V, P, G, A, L, I, or M;
   X6 is T, A, S, G, V, L, or I;
   X7 is E, G, D, A, V, L, or I;
   X8 is P, A, M, G, V, L, or I;
   X9 is T, or S;
   X10 is A, S, M, G, V, L, or I;
   X11 is L, V, G, A, or I;
   X12 is S, N, Q, or T;
   X13 is K, R, D, or E;
   X14 is S, A, T, G, V, L, or I;
   X15 is M, T, V, L, or I;
   X16 is V, G, L, I, or A; and
     wherein CDR1, CDR2, and CDR3 comprise the amino acid sequences:
      (i) SEQ ID NO:70, SEQ ID NO:71, and SEQ ID NO:72;
      (ii) SEQ ID NO:25, SEQ ID NO:26, and SEQ ID NO:27;
      (iii) SEQ ID NO:40, SEQ ID NO:41, and SEQ ID NO:42; or
      (iv) SEQ ID NO:61, SEQ ID NO:62, and SEQ ID NO: 63.

16. The kit of claim 14, wherein the second single-chain antibody comprises a scaffold comprising an amino acid sequence at least 50% identical of to the amino acid sequence:

(SEQ ID NO: 83)
EVX1LQASGGX2X3VQPGGSLRLSX4AASG-(CDR1)-MGWX5RQX6PX7KEREFVSAIS-(CDR2)-YYX8DX9VKGRFTISRDNX10KNTX11YLQMX12SLX13X14EDTAX15YYCX16-(CDR3)-YWGQGTQVTVSS;

wherein
   X1 is K, Q, N, R, D, or E;
   X2 is D, G, E, A, V, L, or I;
   X3 is L, F, W, G, A, V, L, or I;
   X4 is K, R, D, E, N, or Q;
   X5 is V, P, G, A, L, I, or M;
   X6 is T, A, S, G, V, L, or I;
   X7 is E, G, D, A, V, L, or I;
   X8 is P, A, M, G, V, L, or I;
   X9 is T, or S;
   X10 is A, S, M, G, V, L, or I;
   X11 is L, V, G, A, or I;
   X12 is S, N, Q, or T;
   X13 is K, R, D, or E;
   X14 is S, A, T, G, V, L, or I;
   X15 is M, T, V, L, or I;
   X16 is V, G, L, I, or A; and
     wherein CDR1 comprises the amino acid sequence of SEQ ID NO:70, CDR2 comprises and amino acid sequence of SEQ ID NO:71, and CDR3 comprises the amino acid sequence of SEQ ID NO:72.

17. The kit of claim 9, wherein the first single-chain antibody and the second single-chain antibody dimerize in the presence of cannabidiol.

18. A method for detecting cannabidiol, comprising contacting a sample suspected of containing cannabidiol with the first single-chain antibody and the second single-chain antibody of the kit of claim 17, and detecting a dimer of the first single-chain antibody and the second single-chain antibody, thereby detecting cannabidiol in the sample.

* * * * *

```
                     SEQUENCE LISTING

<160> NUMBER OF SEQ ID NOS: 83

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 1

Ser Thr Ser Arg Gln Tyr Asp
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Ser Asn Gln Asp Gln Pro Pro
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Phe Lys Gln His His Ala Asn Gly Ala
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 4

Asp Thr Ser Glu Asp Tyr Asp
1               5

<210> SEQ ID NO 5
<211> LENGTH: 7
```

```
<212> TYPE: PRT
<213> ORGANISM: Artificial Sequence
<220> FEATURE:
<223> OTHER INFORMATION: Synthetic polypeptide

<400> SEQUENCE: 5

Phe Thr Ser Ser Asn His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Phe Lys Lys His Ala Ser Phe Pro Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

His Thr Ser Asn Ala Tyr Asp
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Ser Phe Pro Asp Ala Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Tyr Lys Asn His Pro Tyr Asp Pro Pro
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 10

Asp Thr Tyr Arg Leu Asp Thr
1               5

<210> SEQ ID NO 11
<211> LENGTH: 7
<212> TYPE: PRT
```

```
<213> ORGANISM: Artificial Sequence
<220> FEATURE:
<223> OTHER INFORMATION: Synthetic polypeptide

<400> SEQUENCE: 11

Tyr Arg Thr Asp Gln Asp His
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Gly His Ser Trp Trp Asp Leu Asp Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 13

Thr Gly Trp Glu Ile Glu Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Phe Arg Ala Asn Arg Phe Glu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 15

Ser Thr Phe Asp Ser Pro Ser Arg Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 16

Tyr Thr Ser Phe Gln Tyr Val
1               5

<210> SEQ ID NO 17
<211> LENGTH: 7
<212> TYPE: PRT
<213> ORGANISM: Artificial Sequence
```

```
<220> FEATURE:
<223> OTHER INFORMATION: Synthetic polypeptide

<400> SEQUENCE: 17

Trp Leu Asn Gly Gln Val His
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 18

Ser Met Val Phe Asp His Pro Gln Ser Gly Gly Gly Val Glu Thr
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 19

Tyr Gly Ser Asp Leu Asp Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 20

Tyr Ala Gln Asp Asp Trp Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 21

Met Ser Ile Trp Pro Glu Gln His His
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 22

Asp Ser Ser Trp Trp Asp Gly
1               5

<210> SEQ ID NO 23
<211> LENGTH: 7
<212> TYPE: PRT
<213> ORGANISM: Artificial Sequence
<220> FEATURE:
```

<223> OTHER INFORMATION: Synthetic polypeptide

<400> SEQUENCE: 23

Trp Ala Phe Asp Asn Trp Arg
1               5

<210> SEQ ID NO 24
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 24

Tyr Thr Asn Ile Asp Phe Gln Ala Tyr Gln Ser Trp Phe Gln Asn Pro
1               5                   10                  15

Pro Glu

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 25

Arg Phe Ser Trp Gly Glu Glu
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 26

Trp Ala Ala Thr Pro Trp Gln
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 27

Asp Glu Trp His Ile Gly His Val Ser
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 28

Tyr Thr Ser Asp Gln Asp Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 29

Ser Ser Gln Ser Glu Ile Ala
1               5

<210> SEQ ID NO 30
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 30

Tyr Arg Gln Ser Val His Pro Gln Ile Ala Ser Met
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 31

Phe Thr Phe Ser Gln Glu Glu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 32

Phe Glu Asp Gly Met Lys Gly
1               5

<210> SEQ ID NO 33
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 33

Trp Trp Tyr Glu Ser His Pro Gln Phe Gln His Gln
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 34

Asp Thr Phe Asp Leu Ser Ala
1               5

<210> SEQ ID NO 35
<211> LENGTH: 7
<212> TYPE: PRT
<213> ORGANISM: Artificial Sequence
<220> FEATURE:

<223> OTHER INFORMATION: Synthetic polypeptide

<400> SEQUENCE: 35

Trp Arg Asp Asn Pro Phe Arg
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 36

Met Leu Gln Leu His His His Asp Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 37

Asp Thr Tyr Asn Trp Asp Val
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 38

Tyr Glu Pro Ser Met Tyr Thr
1               5

<210> SEQ ID NO 39
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 39

Met Met Ser Ser Leu His Thr Phe Trp Ala Asn Phe Gln Ser Asp
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 40

Thr Thr Ser Asp Asn Asp Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 41

Trp Asn Gly Gly Arg Asp Glu
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 42

Tyr Gln Asp Asn Arg Ser Trp Gln Glu
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 43

Gly Ser Tyr Ser Trp Asp Ala
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 44

Tyr Phe Gly His Asn Ala Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 45

Val His Phe Trp Lys Leu Leu Asn Glu
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 46

Ser Thr Tyr Glu Trp Tyr Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic polypeptide

```
<400> SEQUENCE: 47

Trp Asp Glu Asp Asn Trp Asn
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 48

Glu Pro Gln Asp Gly Trp Thr Gly Val
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 49

Tyr Thr Ser Ala Gly Glu Ile
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 50

Trp Trp Asp Gly Phe Ala Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 51

Ala His Pro Ser Ser Thr Lys Met Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 52

Arg Phe Ser Trp Gly Glu Glu
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 53

Trp Ala Thr Ala Pro Trp Gln
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 54

Tyr Glu Trp His Ile Gly His Val Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 55

Asp Phe Ser Ser Trp Asp Ala
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 56

Glu Gly His Ser Met Thr Ala
1               5

<210> SEQ ID NO 57
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 57

Asp Ile Glu Phe Asp Leu Ser Met Asn His Met Tyr Leu Val Gln
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 58

Thr Thr Ser Asp Trp Tyr Asp
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 59

Trp Trp Pro Thr Arg Ala Val
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 60

Asp Trp Ser Phe Gly Met Met Gln Gln
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 61

Gly Tyr Ser Arg Ala Asp Asp
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 62

Phe Gly Glu Thr Asp Ser Phe
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 63

Tyr His Asn Tyr Thr Asn Met Phe Glu
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 64

Asp Phe Tyr Lys Leu Tyr Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 65

Trp Glu Ala Gly Met Ser His
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 66

Leu Gln Asp Trp Met Arg Glu Trp Glu
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 67

Arg Phe Ser Trp Gly Glu Lys
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 68

Trp Ala Ala Ala Pro Trp Gln
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 69

Asp Glu Trp Arg Ile Asp His Val Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 70

Thr Thr Tyr Gly Gln Thr Asn
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic polypeptide
```

```
<400> SEQUENCE: 71

Gly Leu Gln Gly Arg Asp Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 72

Phe His Asp Phe Leu Arg Met Trp Glu
1               5

<210> SEQ ID NO 73
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 73

Asp Thr Ser Asn Ala Ser Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 74

Trp Ser Ser Ser Pro Gly Asn
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 75

Met Asp Ala Phe His Pro Gln Ala Trp
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 76

Tyr Gly Ser Phe Leu Asp Ser
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic polypeptide
```

<400> SEQUENCE: 77

Tyr Ala Lys Asp Asp Gly Val
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 78

Met Ser Ile Trp Ala Glu Gln His His
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 79

Asp Tyr Ser Ser Thr Glu Ile
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 80

Ala Gln Pro Gly Val Gln Gln
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 81

Asn Val Ala Phe Arg His Asn His Asp
1               5

<210> SEQ ID NO 82
<211> LENGTH: 96
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (26)..(27)
<223> OTHER INFORMATION: CDR1 domain is between residues 26 and 27
<220> FEATURE:
<221> NAME/KEY: MISC_FEATURE
<222> LOCATION: (45)..(46)
<223> OTHER INFORMATION: CDR2 domain is between residues 45 and 46
<220> FEATURE:
<221> NAME/KEY: MISC_FEATURE
<222> LOCATION: (84)..(85)
<223> OTHER INFORMATION: CDR3 domain is between residues 84 and 85

<400> SEQUENCE: 82

Glu Val Gln Leu Gln Ala Ser Gly Gly Gly Phe Val Gln Pro Gly Gly
1               5                   10                  15

Ser Leu Arg Leu Ser Cys Ala Ala Ser Gly Met Gly Trp Phe Arg Gln
            20                  25                  30

Ala Pro Gly Lys Glu Arg Glu Phe Val Ser Ala Ile Ser Tyr Tyr Ala
        35                  40                  45

Asp Ser Val Lys Gly Arg Phe Thr Ile Ser Arg Asp Asn Ser Lys Asn
    50                  55                  60

Thr Val Tyr Leu Gln Met Asn Ser Leu Arg Ala Glu Asp Thr Ala Thr
65                  70                  75                  80

Tyr Tyr Cys Ala Tyr Trp Gly Gln Gly Thr Gln Val Thr Val Ser Ser
                85                  90                  95

```
<210> SEQ ID NO 83
<211> LENGTH: 96
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa can be K, Q, N, R, D, or E
<220> FEATURE:
<221> NAME/KEY: MISC_FEATURE
<222> LOCATION: (10)..(10)
<223> OTHER INFORMATION: Xaa can be D, G, E, A, V, L, or I
<220> FEATURE:
<221> NAME/KEY: MISC_FEATURE
<222> LOCATION: (11)..(11)
<223> OTHER INFORMATION: Xaa can be L, F, W, G, A, V, L, or I
<220> FEATURE:
<221> NAME/KEY: MISC_FEATURE
<222> LOCATION: (22)..(22)
<223> OTHER INFORMATION: Xaa can be K, R, D, E, N, or Q
<220> FEATURE:
<221> NAME/KEY: MISC_FEATURE
<222> LOCATION: (26)..(27)
<223> OTHER INFORMATION: CDR1 domain is between residues 26 and 27
<220> FEATURE:
<221> NAME/KEY: MISC_FEATURE
<222> LOCATION: (30)..(30)
<223> OTHER INFORMATION: Xaa can be V, P, G, A, L, I, or M
<220> FEATURE:
<221> NAME/KEY: MISC_FEATURE
<222> LOCATION: (33)..(33)
<223> OTHER INFORMATION: Xaa can be T, A, S, G, V, L, or I
<220> FEATURE:
<221> NAME/KEY: MISC_FEATURE
<222> LOCATION: (35)..(35)
<223> OTHER INFORMATION: Xaa can be E, G, D, A, V, L, or I
<220> FEATURE:
<221> NAME/KEY: MISC_FEATURE
<222> LOCATION: (45)..(46)
<223> OTHER INFORMATION: CDR2 domain is between residues 45 and 46
<220> FEATURE:
<221> NAME/KEY: MISC_FEATURE
<222> LOCATION: (48)..(48)
<223> OTHER INFORMATION: Xaa can be P, A, M, G, V, L, or I
<220> FEATURE:
<221> NAME/KEY: MISC_FEATURE
<222> LOCATION: (50)..(50)
<223> OTHER INFORMATION: Xaa can be T, or S
<220> FEATURE:
<221> NAME/KEY: MISC_FEATURE
<222> LOCATION: (62)..(62)
<223> OTHER INFORMATION: Xaa can be A, S, M, G, V, L, or I
<220> FEATURE:
<221> NAME/KEY: MISC_FEATURE
<222> LOCATION: (66)..(66)
```

```
<223>  OTHER INFORMATION:  Xaa can be L, V, G, A, or I
<220>  FEATURE:
<221>  NAME/KEY: MISC_FEATURE
<222>  LOCATION: (71)..(71)
<223>  OTHER INFORMATION:  Xaa can be S, N, Q, or T
<220>  FEATURE:
<221>  NAME/KEY: MISC_FEATURE
<222>  LOCATION: (74)..(74)
<223>  OTHER INFORMATION:  Xaa can be K, R, D, or E
<220>  FEATURE:
<221>  NAME/KEY: MISC_FEATURE
<222>  LOCATION: (75)..(75)
<223>  OTHER INFORMATION:  Xaa can be S, A, T, G, V, L, or I
<220>  FEATURE:
<221>  NAME/KEY: MISC_FEATURE
<222>  LOCATION: (80)..(80)
<223>  OTHER INFORMATION:  Xaa can be M, T, V, L, or I
<220>  FEATURE:
<221>  NAME/KEY: MISC_FEATURE
<222>  LOCATION: (84)..(85)
<223>  OTHER INFORMATION:  CDR3 domain is between residues 84 and 85
<220>  FEATURE:
<221>  NAME/KEY: MISC_FEATURE
<222>  LOCATION: (84)..(84)
<223>  OTHER INFORMATION:  Xaa can be V, G, L, I, or A

<400>  SEQUENCE: 83

Glu Val Xaa Leu Gln Ala Ser Gly Gly Xaa Xaa Val Gln Pro Gly Gly
1               5                   10                  15

Ser Leu Arg Leu Ser Xaa Ala Ala Ser Gly Met Gly Trp Xaa Arg Gln
            20                  25                  30

Xaa Pro Xaa Lys Glu Arg Glu Phe Val Ser Ala Ile Ser Tyr Tyr Xaa
        35                  40                  45

Asp Xaa Val Lys Gly Arg Phe Thr Ile Ser Arg Asp Asn Xaa Lys Asn
    50                  55                  60

Thr Xaa Tyr Leu Gln Met Xaa Ser Leu Xaa Xaa Glu Asp Thr Ala Xaa
65              70                  75                  80

Tyr Tyr Cys Xaa Tyr Trp Gly Gln Gly Thr Gln Val Thr Val Ser Ser
                85                  90                  95
```